United States Patent
Jordan et al.

(10) Patent No.: US 7,993,884 B2
(45) Date of Patent: Aug. 9, 2011

(54) BETA-XYLOSIDASE FOR CONVERSION OF PLANT CELL WALL CARBOHYDRATES TO SIMPLE SUGARS

(75) Inventors: Douglas B. Jordan, Peoria, IL (US); Xin Liang Li, Morton, IL (US); Christopher A. Dunlap, Dunlap, IL (US); Terence R. Whitehead, Peoria, IL (US); Michael A. Cotta, Edelstein, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 669 days.

(21) Appl. No.: 11/904,577

(22) Filed: Sep. 27, 2007

(65) Prior Publication Data

US 2009/0280541 A1 Nov. 12, 2009

Related U.S. Application Data

(60) Provisional application No. 60/850,668, filed on Oct. 10, 2006.

(51) Int. Cl.
*C12P 19/02* (2006.01)
*C12N 9/00* (2006.01)
*C12N 9/26* (2006.01)
*C07H 21/04* (2006.01)

(52) U.S. Cl. ........ 435/105; 435/183; 435/201; 536/23.2

(58) Field of Classification Search ........................ None
See application file for complete search history.

(56) References Cited

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession O52575. Jun. 1, 1998.*
Saha. J Ind Microbiol Biotechnol. May 2003;30(5):279-91. Epub Apr. 16, 2003.*

* cited by examiner

*Primary Examiner* — Christian Fronda
(74) *Attorney, Agent, or Firm* — Randall E. Deck; John Fado; Lesley Shaw

(57) ABSTRACT

Xylose-containing plant material may be hydrolyzed to xylose using a β-D-xylosidase which exhibits unexpectedly high activity. The enzyme has a $k_{cat}$ value for catalysis of approximately 185 sec$^{-1}$ for 1,4-β-D-xylobiose (X2) when measured at a pH of 5.3 and a temperature of 25° C.; this is at least 10-fold greater than reported for other xylosidases at 25° C. and their optimal pH. The enzyme also has an isoelectric point of approximately 4.4. When reacted at a pH between about 4.5 and about 7.7, the β-D-xylosidase exhibits surprisingly high activity for hydrolyzing xylose-containing plant materials to xylose. The xylose released from plant materials may then be converted to other secondary products such as ethanol by fermentation or other reaction. This β-D-xylosidase may be used alone or in combination with other hydrolytic or xylanolytic enzymes for treatment of lignocellulosic or hemicellulosic plant materials or plant material hydrolysates or xylooligosaccharides.

13 Claims, 39 Drawing Sheets

1 gatcattacc gaactggaac aacgtcacca gcaggaaaag cattacacag atgacagtca 61 gctggctgcc agcaccttgt aaaaacgtgt ttaaattgga gacttcaaga tgaacattca 121 aaatcccgta ttaaaaggct ttaaccccga ccccagcatt gtccgggcag gcgatgacta 181 ctatattgcc acctccacct tcgagtggtt cccgggtgtg cagattcatc attccaaaga 241 tttagtacat tggcacctcg ttgcccatcc cctttccacc acggaatttc tggatatgaa 301 aggcaatccg gattccggcg gcatctgggc acctgacctt tcctatgccg atggcaagtt 361 ctggctcatt tacaccgatg taaaggtcgt agacggcatg tggaaggatt gtcataacta 421 cctgaccacc gccgaagaca taaaaggccc ctggtcaaaa ccgatactcc tgaacggtgc 481 tggctttgat gcctccctgt tccatgaccc cagcggcaaa aaatatctgg tcaatatgta 541 ctgggatcag cgcgtctacc atcataattt ctacggcatt gccctgcagg aatattccgt 601 agccgaagaa aaactcatcg gcaagccgga aatcatctat aagggtaccg atattgccta 661 taccgaaggt ccccacctt actatatcaa cgatatgtat tacctcatga cagctgaagg 721 cggcacgacg tatcagcatt ctgagaccat cgcccgcagc aagactatcc acgggcccta 781 tgaaatacag ccggactatc ccctgctgtc ggcatggaag gaagtccata accccctgca 841 gaatgcggc catgcatcat tagtcgaaac gcaaaacggc cagtggtact tagcccatct 901 gactggcaga cccctgcctg ccccgccgg cttcccccagc cgcgaacgcg aacagcatgc 961 cttctgtccg ctgggcagag aaaccgccat ccaaaaaatc gaatggcagg acggctggcc 1021 cgtagtcgtt ggcggtcagc agggttcctt agaagtcgaa gcacctgacc tgccccagca 1081 ggaatgggca ccgacttacg aagaacgcga tgacttcgat aaggacacct taaacatcaa 1141 cttccagacc ctgcgtatcc ccttcagtga gcatttgggc agtctcaccg cccgtcccgg 1201 cttcctgcgc ctgtacggcc gcgaatccct gcagtccaaa tttacccagg cccatattgc 1261 ccgccgctgg cagtccttca atttcgatgc tggaaccagc gtggaatttt ctccgaactc 1321 cttccagcag atggccggtc ttacctgcta ctacaatacg gaaaactggt ccagcatcca 1381 tgtgacctgg aacgaagaaa aaggccgtat catcgatttg gtcaccgccg acaacggcac 1441 cttctccatg ccgcttgccg gagcagaaat ccccattccc gatgaagtaa agaccgtcca 1501 cttcaaggta tccgtgcgcg gcagaatcta ccaatacgct tattccttcg atggcgaaac 1561 cttccacacc ctgcccatag aactgcccag ctggaaactc tccgatgact atgtgcgcgg 1621 cggcggattc ttcactggtg ctttcgtcgg cataaacgcc attgatatta ccggcacagc 1681 gcttcccgct gactttgatt atttcactta caaggaactg gactgaattc acgttacttg 1741 ttaaaataat agataaaaga gctaactgga ggtacaggca tggttacgat gaaaagtatt 1801 gcggaaatat gcggtgtttc ccgaggcaca gtagaccgcg cattaaatgg ccgcggccgg 1861 gtaaactcag aaaccgctga caaaatccgt caaatcgcca aggaattagg ctatacccccc 1921 aaccctgccg gcaaagcact ttcagcccga aaaaaaagac cagtcatcgg cattgtaatc 1981 ccctctgaga caaccccctt ctttgacgat gtactaaagg gcatggaaga agcagctgcc 2041 caatatcaaa tctatggtgt ccaaataaaa taccatacga tgaaggttga tgacccggcc 2101 aaacagttag caaccctgca aaaaatcgaa gaccaggtac aggcgctcat catcaacccc 2161 attgatgacc cagctattgt cagccaaatc aatcgcatga ttgacaaagg cgtcttcgtg 2221 gtaaccgtca acaacgatat tgaaggtaca aagcgccatt gctatgtggg cagtgactac 2281 tacaacggcg gcataacatc ctgtgcactg atggaagcgc tcgtgggcaa aacagccaat 2341 ctggccatta tcctcggcag cctgaaactg cgcggtcatc gcctccgtct ggaaggtttc 2401 aaatcccgca tgcagcgatt gccggatttt cagctggcaa ccgtgctgga aacaatgat 2461 gatgacattt acgcctacga aaaaaccaag gagcttttaa ccgctcatcc ggaaatcaat 2521 gccatcagca ttttggccgc cggtgtctac ggcacctgcc gtgccgtcat gcagttgccg 2581 gaagaaaaac ggcccttgat c

FIGURE 1

```
1    mniqnpvlkg fnpdpsivra gddyyiatst fewfpgvqih hskdlvhwhl vahplsttef
61   ldmkgnpdsg giwapdlsya dgkfwliytd vkvvdgmwkd chnylttaed ikgpwskpil
121  lngagfdasl fhdpsgkkyl vnmywdqrvy hhnfygialq eysvaeekli gkpeiiykgt
181  diaytegphl yyindmyylm taeggttyqh setiarskti hgpyeiqpdy pllsawkevh
241  nplqkcghas lvetqngqwy lahltgrplp apagfpsrer eqhafcplgr etaiqkiewq
301  dgwpvvvggq qgsleveapd lpqqewapty eerddfdkdt lninfqtlri pfsehlgslt
361  arpgflrlyg reslqskftq ahiarrwqsf nfdagtsvef spnsfqqmag ltcyyntenw
421  ssihvtwnee kgriidlvta dngtfsmpla gaeipipdev ktvhfkvsvr griyqyaysf
481  dgetfhtlpi elpswklsdd yvrgggfftg afvginaidi tgtalpadfd yftykeld
```

FIGURE 2

SEQUENCE LISTING

<160> NUMBER OF SEQ ID NOS: 7

<210> SEQ ID NO 1
<211> LENGTH: 2601
<212> TYPE: DNA
<213> ORGANISM: Selenomonas ruminantium

<400> SEQUENCE: 1

```
gatcattacc gaactggaac aacgtcacca gcaggaaaag cattacacag atgacagtca      60
gctggctgcc agcaccttgt aaaaacgtgt ttaaattgga gacttcaaga tgaacattca     120
aaatcccgta ttaaaaggct ttaacccccga ccccagcatt gtccgggcag gcgatgacta    180
ctatattgcc acctccacct tcgagtggtt ccccggtgtg cagattcatc attccaaaga    240
tttagtacat tggcacctcg ttgcccatcc cctttccacc acggaatttc tggatatgaa    300
aggcaatccg gattccggcg gcatctgggc acctgacctt tcctatgccg atggcaagtt    360
ctggctcatt tacaccgatg taaaggtcgt agacggcatg tggaaggatt gtcataacta    420
cctgaccacc gccgaagaca taaaaggccc ctggtcaaaa ccgatactcc tgaacggtgc    480
tggctttgat gcctccctgt tccatgaccc cagcggcaaa aaatatctgg tcaatatgta    540
ctgggatcag cgcgtctacc atcataattt ctacggcatt gccctgcagg aatattccgt    600
agccgaagaa aaactcatcg gcaagccgga aatcatctat aagggtaccg atattgccta    660
taccgaaggt cccccacctt actatatcaa cgatatgtat tacctcatga cagctgaagg    720
cggcacgacg tatcagcatt ctgagaccat cgcccgcagc aagactatcc acgggcccta    780
tgaaatacag ccggactatc ccctgctgtc ggcatggaag gaagtccata accccctgca    840
gaaatgcggc catgcatcat tagtcgaaac gcaaaacggc cagtggtact tagcccatct    900
gactggcaga ccccctgcctg cccccgccgg cttccccagc cgcgaacgcg aacagcatgc    960
cttctgtccg ctgggcagag aaaccgccat ccaaaaaatc gaatggcagg acggctggcc   1020
cgtagtcgtt ggcggtcagc agggttcctt agaagtcgaa gcacctgacc tgccccagca   1080
ggaatgggca ccgacttacg aagaacgcga tgacttcgat aaggacacct taaacatcaa   1140
cttccagacc ctgcgtatcc ccttcagtga gcatttgggc agtctcaccg cccgtcccgg   1200
cttcctgcgc ctgtacggcc gcgaatccct gcagtccaaa tttacccagg cccatattgc   1260
ccgccgctgg cagtccttca atttcgatgc tggaaccagc gtggaatttt ctccgaactc   1320
cttccagcag atggccggtc ttacctgcta ctacaatacg gaaaactggt ccagcatcca   1380
tgtgacctgg aacgaagaaa aaggccgtat catcgatttg gtcaccgccg acaacggcac   1440
```

```
cttctccatg ccgcttgccg gagcagaaat ccccattccc gatgaagtaa agaccgtcca    1500
cttcaaggta tccgtgcgcg gcagaatcta ccaatacgct tattccttcg atggcgaaac    1560
cttccacacc ctgcccatag aactgccag ctggaaactc tccgatgact atgtgcgcgg    1620
cggcggattc ttcactggtg ctttcgtcgg cataaacgcc attgatatta ccggcacagc    1680
gcttcccgct gactttgatt atttcactta caaggaactg gactgaattc acgttacttg    1740 ttaaataat agataaaaga gctaactgga ggtacaggca tggttacgat gaaaagtatt    1800
gcggaaatat gcggtgtttc ccgaggcaca gtagaccgcg cattaaatgg ccgcggccgg    1860
gtaaactcag aaaccgctga caaaatccgt caaatcgcca aggaattagg ctatacccc    1920 aaccctgccg gcaaagcact ttcagcccga aaaaaagac cagtcatcgg cattgtaatc    1980
ccctctgaga acaaccccatt ctttgacgat gtactaaagg gcatggaaga agcagctgcc    2040
caatatcaaa tctatggtgt ccaaataaaa taccatacga tgaaaggtta tgacccggcc    2100
aaacagttag caaccctgca aaaatcgaa gaccaggtac aggcgctcat catcaacccc    2160
attgatgacc cagctattgt cagccaaatc aatcgcatga ttgacaaagg cgtcttcgtg    2220
gtaaccgtca caacgatat tgaaggtaca aagcgccatt gctatgtggg cagtgactac    2280
tacaacggcg gcataacatc ctgtgcactg atggaagcgc tcgtgggcaa aacagccaat    2340
ctggccatta tcctcggcag cctgaaactg cgcggtcatc gcctccgtct ggaaggtttc    2400
aaatcccgca tgcagcgatt gccggatttt cagctggcaa ccgtgctgga aacaatgat    2460 gatgacattt acgcctacga aaaaaccaag gagcttttaa ccgctcatcc ggaaatcaat    2520
gccatcagca ttttggccgc cggtgtctac ggcacctgcc gtgccgtcat gcagttgccg    2580
gaagaaaaac ggcccttgat c                                               2601

<210> SEQ ID NO 2
<211> LENGTH: 538
<212> TYPE: PRT
<213> ORGANISM: selenomonas ruminantium

<400> SEQUENCE: 2

Met Asn Ile Gln Asn Pro Val Leu Lys Gly Phe Asn Pro Asp Pro Ser
1               5                   10                  15

Ile Val Arg Ala Gly Asp Asp Tyr Tyr Ile Ala Thr Ser Thr Phe Glu
            20                  25                  30

Trp Phe Pro Gly Val Gln Ile His His Ser Lys Asp Leu Val His Trp
        35                  40                  45

His Leu Val Ala His Pro Leu Ser Thr Thr Glu Phe Leu Asp Met Lys
    50                  55                  60

Gly Asn Pro Asp Ser Gly Gly Ile Trp Ala Pro Asp Leu Ser Tyr Ala
65                  70                  75                  80

Asp Gly Lys Phe Trp Leu Ile Tyr Thr Asp Val Lys Val Val Asp Gly
                85                  90                  95

Met Trp Lys Asp Cys His Asn Tyr Leu Thr Thr Ala Glu Asp Ile Lys
            100                 105                 110

Gly Pro Trp Ser Lys Pro Ile Leu Leu Asn Gly Ala Gly Phe Asp Ala
        115                 120                 125

Ser Leu Phe His Asp Pro Ser Gly Lys Lys Tyr Leu Val Asn Met Tyr
    130                 135                 140

Trp Asp Gln Arg Val Tyr His His Asn Phe Tyr Gly Ile Ala Leu Gln
145                 150                 155                 160

Glu Tyr Ser Val Ala Glu Glu Lys Leu Ile Gly Lys Pro Glu Ile Ile
```

```
                    165                 170                 175
Tyr Lys Gly Thr Asp Ile Ala Tyr Thr Glu Gly Pro His Leu Tyr Tyr
                180                 185                 190
Ile Asn Asp Met Tyr Tyr Leu Met Thr Ala Glu Gly Thr Thr Tyr
            195                 200                 205
Gln His Ser Glu Thr Ile Ala Arg Ser Lys Thr Ile His Gly Pro Tyr
        210                 215                 220
Glu Ile Gln Pro Asp Tyr Pro Leu Leu Ser Ala Trp Lys Glu Val His
225                 230                 235                 240
Asn Pro Leu Gln Lys Cys Gly His Ala Ser Leu Val Glu Thr Gln Asn
                245                 250                 255
Gly Gln Trp Tyr Leu Ala His Leu Thr Gly Arg Pro Leu Pro Ala Pro
            260                 265                 270
Ala Gly Phe Pro Ser Arg Glu Arg Gln His Ala Phe Cys Pro Leu
        275                 280                 285
Gly Arg Glu Thr Ala Ile Gln Lys Ile Glu Trp Gln Asp Gly Trp Pro
290                 295                 300
Val Val Val Gly Gly Gln Gln Gly Ser Leu Glu Val Glu Ala Pro Asp
305                 310                 315                 320
Leu Pro Gln Gln Glu Trp Ala Pro Thr Tyr Glu Glu Arg Asp Asp Phe
                325                 330                 335
Asp Lys Asp Thr Leu Asn Ile Asn Phe Gln Thr Leu Arg Ile Pro Phe
                340                 345                 350
Ser Glu His Leu Gly Ser Leu Thr Ala Arg Pro Gly Phe Leu Arg Leu
                355                 360                 365
Tyr Gly Arg Glu Ser Leu Gln Ser Lys Phe Thr Gln Ala His Ile Ala
        370                 375                 380
Arg Arg Trp Gln Ser Phe Asn Phe Asp Ala Gly Thr Ser Val Glu Phe
385                 390                 395                 400
Ser Pro Asn Ser Phe Gln Gln Met Ala Gly Leu Thr Cys Tyr Tyr Asn
                405                 410                 415
Thr Glu Asn Trp Ser Ser Ile His Val Thr Trp Asn Glu Glu Lys Gly
                420                 425                 430
Arg Ile Ile Asp Leu Val Thr Ala Asp Asn Gly Thr Phe Ser Met Pro
        435                 440                 445
Leu Ala Gly Ala Glu Ile Pro Ile Pro Asp Glu Val Lys Thr Val His
        450                 455                 460
Phe Lys Val Ser Val Arg Gly Arg Ile Tyr Gln Tyr Ala Tyr Ser Phe
465                 470                 475                 480
Asp Gly Glu Thr Phe His Thr Leu Pro Ile Glu Leu Pro Ser Trp Lys
                485                 490                 495
Leu Ser Asp Asp Tyr Val Arg Gly Gly Phe Phe Thr Gly Ala Phe
                500                 505                 510
Val Gly Ile Asn Ala Ile Asp Ile Thr Gly Thr Ala Leu Pro Ala Asp
            515                 520                 525
Phe Asp Tyr Phe Thr Tyr Lys Glu Leu Asp
    530                 535
```

<210> SEQ ID NO 3
<211> LENGTH: 52
<212> TYPE: DNA
<213> ORGANISM: selenomonas ruminantium

<400> SEQUENCE: 3
ggctttaacc ccgccccagc attgtcgaca atgctggggc ggggttaaag cc    52

```
<210> SEQ ID NO 4
<211> LENGTH: 58
<212> TYPE: DNA
<213> ORGANISM: Selenomonas ruminantium

<400> SEQUENCE: 4
cggtgctggc tttgcagcct ccctgttccg gaacagggag gctgcaaagc cagcaccg        58

<210> SEQ ID NO 5
<211> LENGTH: 66
<212> TYPE: DNA
<213> ORGANISM: Selenomonas ruminantium

<400> SEQUENCE: 5
gatattgcct ataccgccgg tccccacctt tacgtaaagg tggggaccgg cggtataggc      60
aatatc                                                                66

<210> SEQ ID NO 6
<211> LENGTH: 78
<212> TYPE: DNA
<213> ORGANISM: Selenomonas ruminantium

<400> SEQUENCE: 6
ccctgcagaa atgcggcgca gcatcattag tcgaaacgcg cgtttcgact aatgatgctg      60
cgccgcattt ctgcaggg                                                   78

<210> SEQ ID NO 7
<211> LENGTH: 58
<212> TYPE: DNA
<213> ORGANISM: Selenomonas ruminantium

<400> SEQUENCE: 7
tgtccgctgg gcgcagaaac cgccatccat ggatggcggt ttctgcgccc agcggaca        58
```

BETA-XYLOSIDASE FOR CONVERSION OF PLANT CELL WALL CARBOHYDRATES TO SIMPLE SUGARS

CROSS-REFERENCE TO RELATED APPLICATION

This application claims the benefit under 35 U.S.C. 1.19(e) of U.S. provisional No. 60/850,668, filed Oct. 10, 2006, the contents of which are incorporated by reference herein.

BACKGROUND OF THE INVENTION

1. Field of the Invention

The invention relates to a novel process for hydrolyzing plant carbohydrates to xylose.

2. Description of the Prior Art

Plant biomass is a promising substrate for ethanol fuel production due to its ready availability and low cost. Most fuel ethanol is currently produced from hexose sugars derived from corn starch or cane syrup utilizing either *S. cerevisiae* or *Z. mobilis*. However, these are relatively expensive sources of biomass sugars and have competing value as foods. Moreover, starches and sugars represent only a fraction of the total carbohydrates available from plant material. Most of the available plant biomass is from sources such as residues and by-products from agriculture, gardening, and forestry, including straw, hulls, stalks, pulping wastes, sawdust, wood chips and other cellulosic materials. The principal component of the plant biomass from these sources is found as lignocellulose, making up approximately 90% of the dry weight of most plant material. Lignocellulose typically comprises approximately 30-60% cellulose, by weight, 20-50% hemicellulose, and 10-30% lignin. Cellulose is a β-glucan, a polymer of D-glucose units, while hemicellulose is a complex heteropolymer, the majority of which are predominantly polymers (e.g., xylooligosaccharides) of pentose sugar units such as D-xylose and D-arabinose, as well as smaller amounts of hexoses such as mannose, galactose, and glucose. Thus, hydrolysis of cellulose and hemicellulose releases a mixture of neutral sugars which include glucose, xylose, mannose, galactose, and arabinose. Of these sugars, the amount of xylose is second only to glucose in most plant materials.

Because of its abundance in plant biomass, xylose presents potentially significant economic resource for producing ethanol fuels and other valuable products. Methods of saccharifying lignocellulosic materials include acidic or alkaline pretreatments, followed by enzymatic hydrolysis. The use of enzymatic hydrolysis for as much of the saccharification process as possible is desirable for its mild reaction conditions that consume lower amounts energy and produce lower amounts of toxic waste products.

However, owing to low efficiency and high costs of enzymes, the need persists for improved methods for hydrolyzing plant biomass to produce xylose.

SUMMARY OF THE INVENTION

We have now discovered a β-D-xylosidase that exhibits unexpectedly high activity for the hydrolysis of xylose-containing plant material and natural xylooligosaccharides to xylose. The enzyme has a $k_{cat}$ value of catalysis of approximately 185 $sec^{-1}$ for 1,4-β-D-xylobiose (X2) when measured at a pH of 5.3 and a temperature of 25° C., and an isoelectric point of approximately 4.4. When reacted at a pH between about 4.5 and about 7.7, the β-D-xylosidase exhibits surprisingly high activity for hydrolyzing xylose-containing plant materials to xylose. The xylose released from plant materials may then be converted to other secondary products such as ethanol by fermentation or other reaction. This β-D-xylosidase may be used alone or in combination with other hydrolytic or xylanolytic enzymes for treatment of lignocellulosic or hemicellulosic plant materials or plant material hydrolysates or xylooligosaccharides.

In accordance with this discovery, it is an object of this invention to provide an improved β-D-xylosidase having high enzymatic activity for the enzymatic hydrolysis of D-xylose containing plant materials such as lignocellulose, hemicellulose, or plant material hydrolysates or xylooligosaccharides.

Another object of this invention is to provide an improved process for the enzymatic conversion of xylose containing plant materials to xylose using a β-D-xylosidase having high activity and stability at an acidic pH and moderately high temperatures.

Another object of this invention is to provide an improved process for the enzymatic conversion of xylose-containing plant materials to xylose, which may be subsequently fermented to ethanol or other secondary products, using a β-D-xylosidase having high activity at an acidic pH.

Other objects and advantages of this invention will become readily apparent from the ensuing description.

BRIEF DESCRIPTION OF THE DRAWINGS

FIG. 1 shows the gene sequence of the β-D-xylosidase produced by *Selenomonas ruminantium* GA192 deposited in GenBank under accession no. AF040720 (SEQ. ID No. 1).

FIG. 2 shows the predicted amino acid sequence of the β-D-xylosidase (SXA) produced by *Selenomonas ruminantium* GA192 deposited in GenBank under accession no. AAB97967 (SEQ. ID No. 2).

Figure 7:
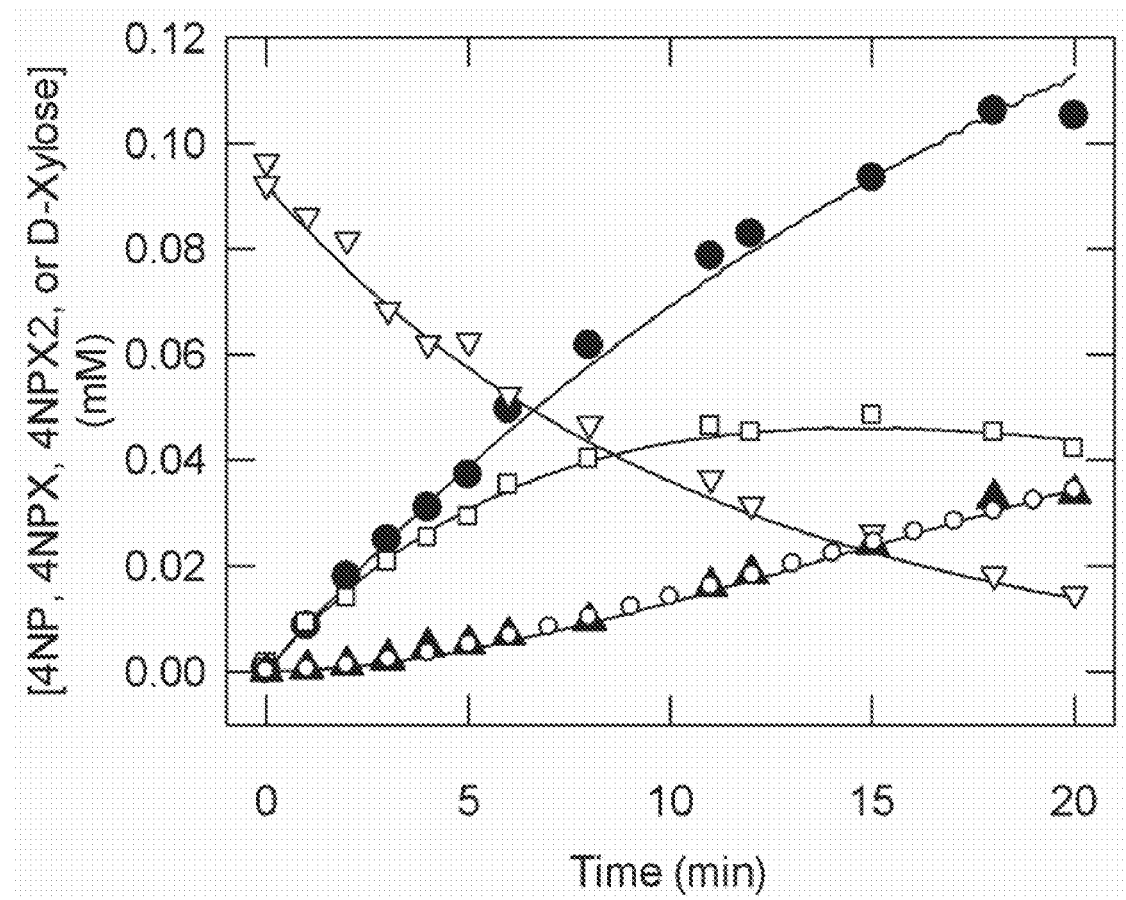

FIG. 7 shows the progress curves for SXA-catalyzed hydrolysis of 4NPX2. Reactions contained 24.8 nM SXA, 0.092 mM 4NPX2, 100 mM sodium phosphate, pH 7.0 and 25° C. Before and after enzyme addition, aliquots were removed with time, quenched and analyzed for substrate and product concentrations: 4NPX2 (▽), 4NPX (□), 4NP (▲), D-xylose (●). In a parallel reaction the absorbance at 400 mm was continuously monitored for a second determination of [4NP] (○). Curves were generated from a KINSIM calculation, using the indicated concentrations of SXA and 4NPX2 and kinetic parameters for SXA acting on 4NPX2 and 4NPX (determined using the same buffer and temperature conditions) as inputs in the following kinetic scheme: E+4NPX2<=>E4NPX2 ($K_m$=0.69±0.43 mM); E4NPX2=>E+4NPX+X1 ($k_{cat}$=50.5±25.7 s$^{-1}$); E+4NPX<=>E4NPX (4=0.443±0.008 mM); E4NPX=>E+4NP+X1 ($k_{cat}$=16.2±0.09 s$^{-1}$) The KINSIM model assumes rapid equilibrium binding, a single D-xylose is hydrolyzed from the nonreducing end of substrate per catalytic cycle and lack of processivity.

Figure 8:
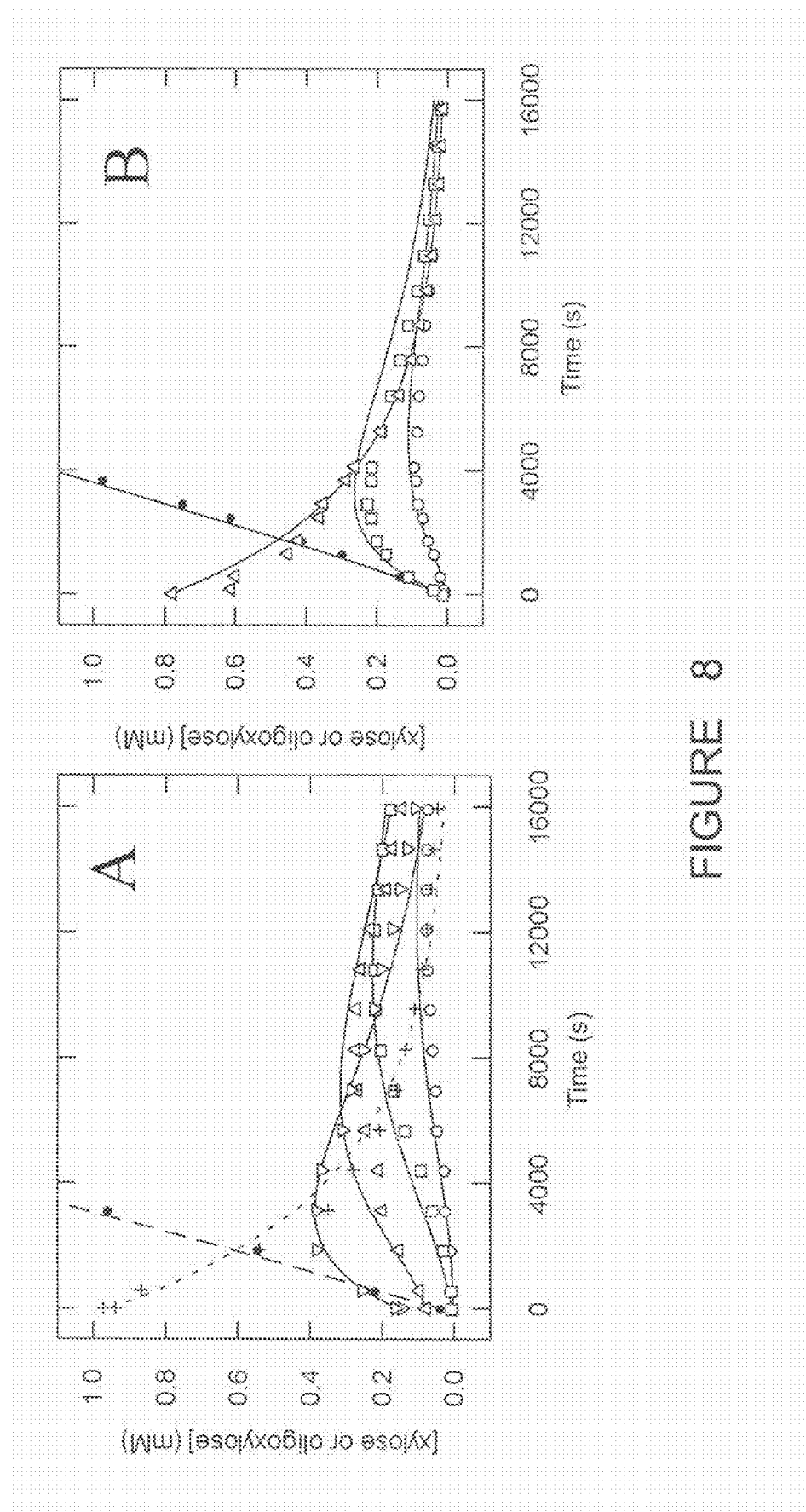

FIG. 8 shows the progress curves for SXA-catalyzed hydrolysis of X6 and X4. Reactions were in 100 mM succinate-NaOH, pH 5.30 and 25° C. Before and after enzyme addition, aliquots were removed with time for determination of reactant and product concentrations by HPLC analysis: X1 (●), X2 (○), X3 (□), X4 (Δ), X5 (▽), X6 (+). Curves were generated from KINSIM calculations using the indicated concentrations of SXA and X1-X6, the kinetic parameters reported in Table 5 for X2-X6, and $K_i$(xylose)=7.40 mM for inputs in the following kinetic scheme: E+X6<=>EX6 ($K_m$=2.7 mM); EX6=>E+X5+X1 ($k_{cat}$=96 s$^{-1}$); E+X5<=>EX5 ($K_m$=3.7 mM); EX5=>E+X4+X1 ($k_{cat}$=150 s$^{-1}$); E+X4<=>EX4 ($K_m$=4.0 mM); EX4=>E+X3+X1 ($k_{cat}$=150 s$^{-1}$); E+X3<=>EX3 ($K_m$=3.8 mM); EX3=>E+X2+X1 ($k_{cat}$=172 s$^{-1}$); E+X2<=>EX2 ($K_m$=4.2 mM); EX2=>E+X1+X1 ($k_{cat}$=412 s$^{-1}$); E+X1<=>EX1 ($K_i$(xylose)=7.40 mM). The KINSIM model assumes rapid equilibrium binding, a single D-xylose is hydrolyzed from the nonreducing end of substrate per catalytic cycle and lack of processivity. (A) Reactions were initiated with enzyme to give initial concentrations of 10 nM SXA, 0.953 mM X6, 0.15 mM X5, 0.077 mM X4, 0.0042 mM X3, 0.0023 mM X2, and 0.036 mM X1. (B) Reactions were initiated with enzyme to give initial concentrations of 9.0 nM SXA, 0.78 mM X4, 0.011 mM X3, 0.0058×2, and 0.016 mM X1.

Figure 9A:
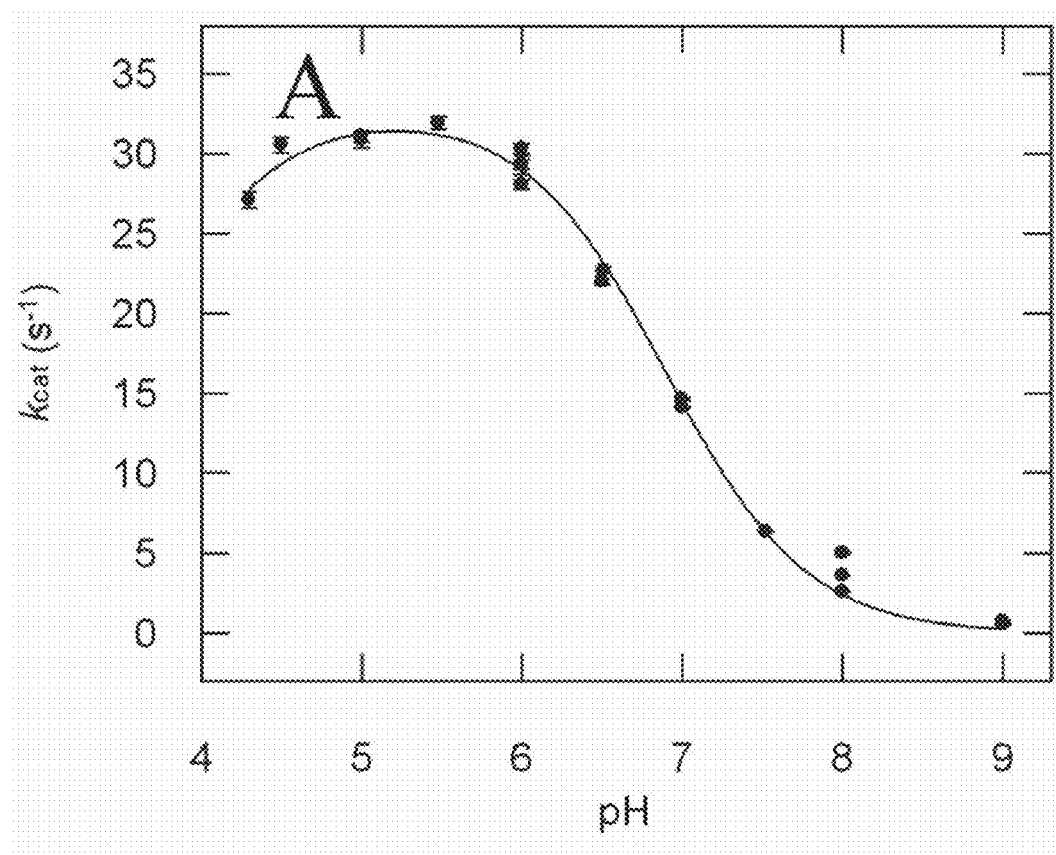
Figure 9B:
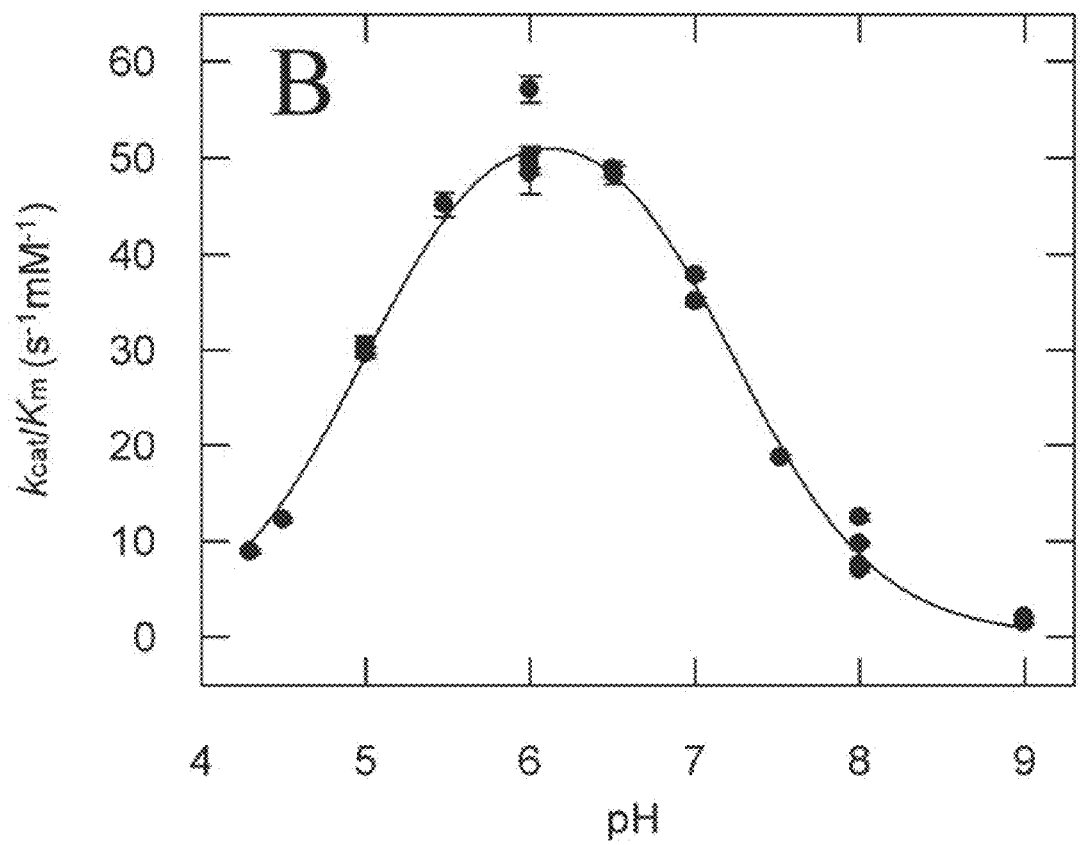

FIG. 9 shows the influence of pH on steady-state kinetic parameters of SXA-catalyzed hydrolysis of 4NPX. Initial-rate data, determined by using Method B, were fitted to Eq. 1 to determine kinetic parameters. Standard errors from fitting the data are indicated. (A) $k_{cat}$ versus pH. The curve was generated by fitting the $k_{cat}$ values for each pH to Eq. 5: pH-independent $k_{cat}$=32.7±0.5 s$^{-1}$, $pK_{a1}$=3.54±0.10, $pK_{a2}$=6.90±0.03. (B) $k_{cat}/K_m$ versus pH. The curve was generated by fitting the $k_{cat}/K_m$ values for each pH to Eq. 5: pH-independent $k_{cat}/K_m$=58.7±1.3 s$^{-1}$ mM$^{-1}$, $pK_{a1}$=5.00±0.04, $pK_{a2}$=7.23±0.04. (C) 1/$K_m$ versus pH. The solid curve was generated by fitting the data to Eq. 7 (two protonatable groups): middle limit 1/$K_m$=1.46±0.33 mM$^{-1}$, upper limit 1/$K_m$=2.79±0.06 mM$^{-1}$, $pK_{a1}$=4.81±0.21, $pK_{a2}$=6.39±0.26, reduced $\chi^2$=0.0242. The dotted curve was generated by fitting the data to Eq. 4 (single protonatable group): pH-independent 1/$K_m$=2.65±0.081 mM$^{-1}$, $pK_a$=5.56±0.08, reduced $\chi^2$=0.0694. F test indicates that there is a 0.022% probability that data fit Eq. 4 as well as Eq. 7.

Figure 10A:
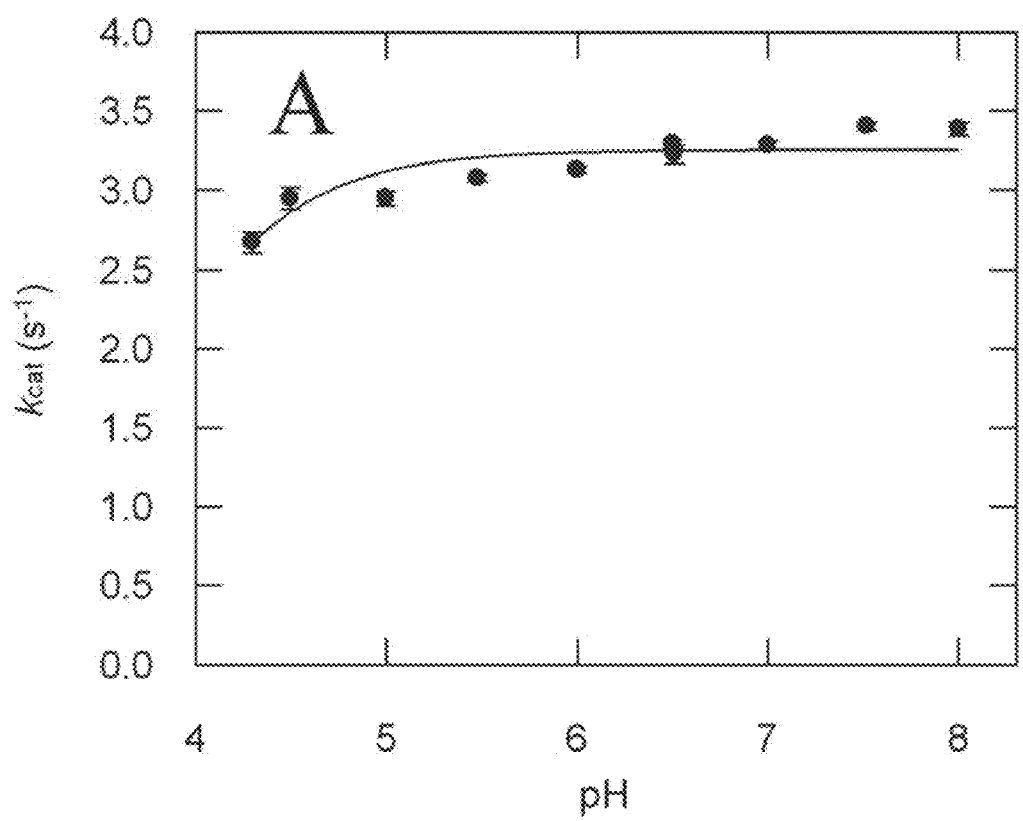
Figure 10B:
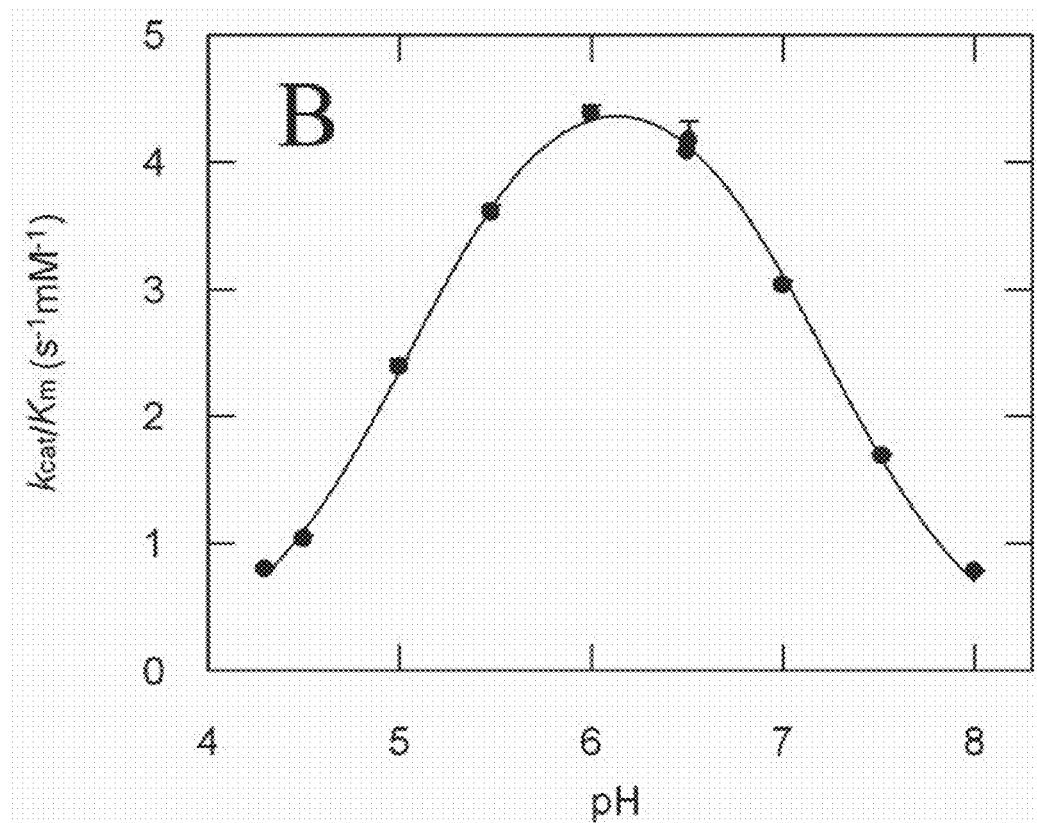
Figure 10C:
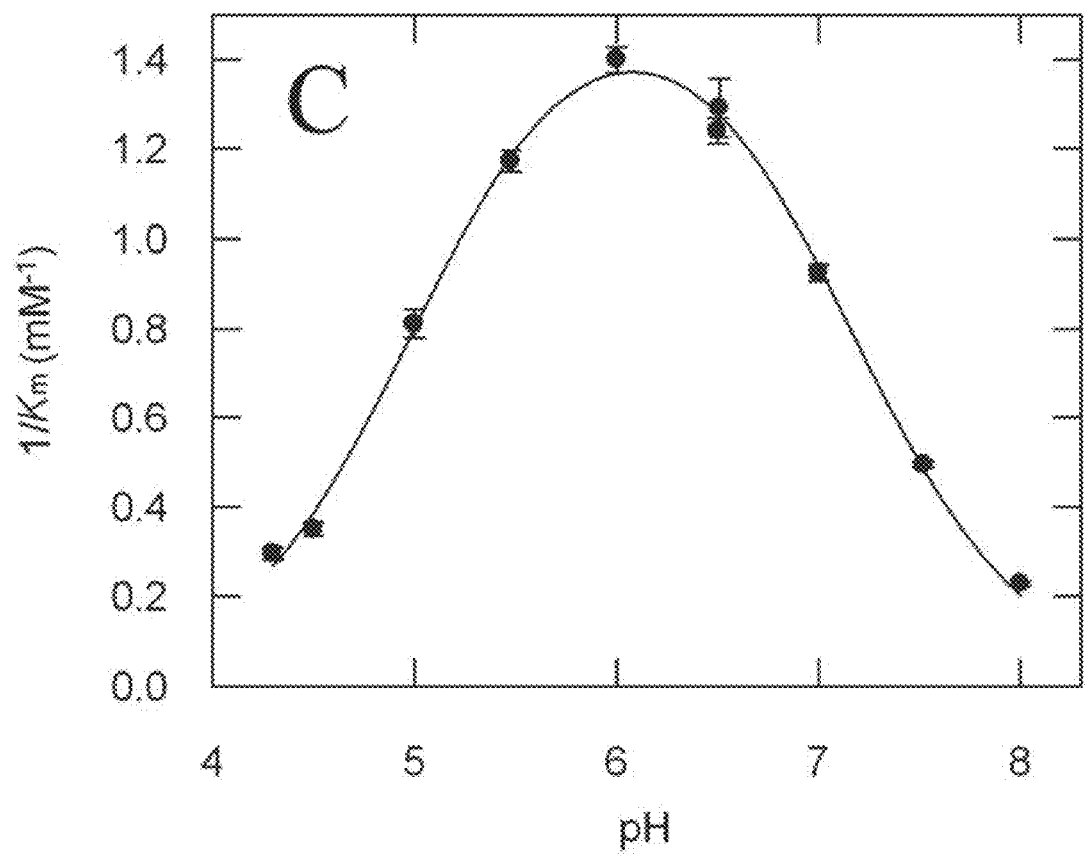

FIG. 10 shows the influence of pH on steady-state kinetic parameters of SXA-catalyzed hydrolysis of 4NPA. Initial-rate data, determined by using Method B, were fitted to Eq. 1 to determine kinetic parameters. Standard errors from fitting the data are indicated. (A) $k_{cat}$ versus pH. The curve was generated by fitting the $k_{cat}$ values for each pH to Eq. 4: pH-independent $k_{cat}$=3.25±0.05 s$^{-1}$, $pK_a$=3.64±0.10. (B) $k_{cat}/K_m$ versus pH. The curve was generated by fitting the $k_{cat}/K_m$ values for each pH to Eq. 5: pH-independent $k_{cat}/K_m$=5.10±0.07 s$^{-1}$mM$^{-1}$, $pK_{a1}$=5.06±0.02, $pK_{a2}$=7.20±0.02. (C) 1/$K_m$ versus pH. The curve was generated by fitting the data to Eq. 5: pH-independent 1/$K_m$=1.60±0.02 mM$^{-1}$, $pK_{a1}$=5.00±0.03, $pK_{a2}$=7.16±0.03.

Figure 11:
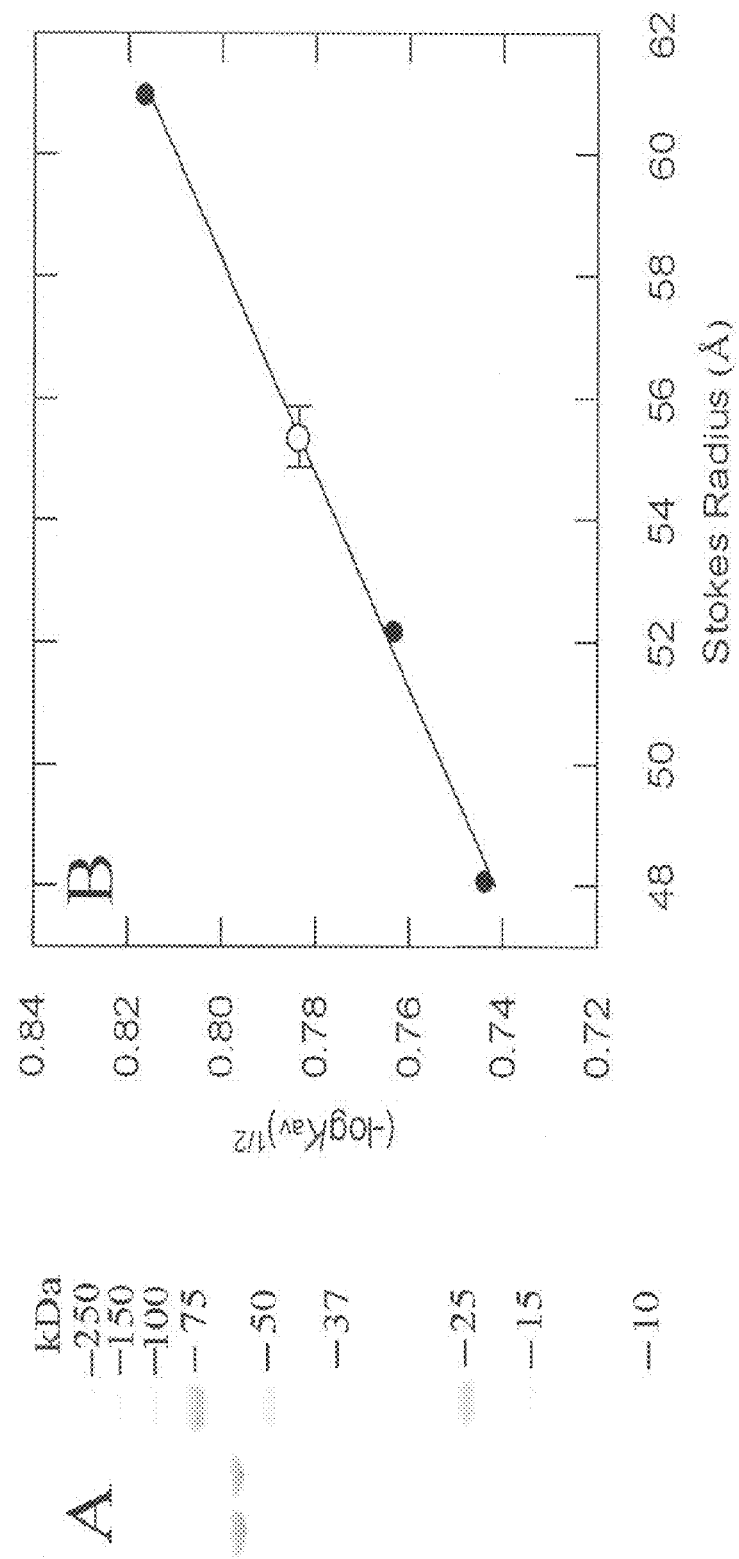

FIG. 11 shows the molecular mass and size of heterologously-produced SXA. (A) SDS-PAGE analysis of SXA. From left to right are lanes containing 1 mg SXA, 0.5 mg SXA, protein standards, and molecular masses (in kDa) of the protein standards. (B) Stokes radius of SXA. $K_{av}$ values were determined for protein standards (●) of known Stokes radius and the line was drawn by fitting the values to equation 2. SXA (○) is positioned by using the value determined for $K_{av}$ and the value determined for its Stokes radius ($R_S$)±the standard error of the estimate of the standard line ($R_S$=55.4±0.5 Å).

Figure 12:
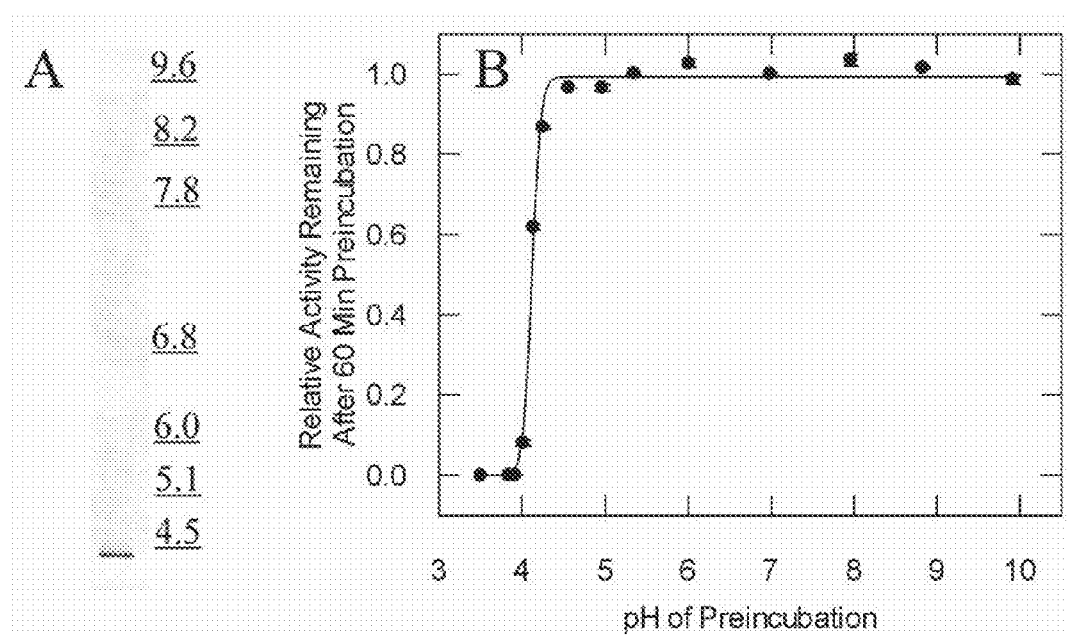

FIG. 12 shows the influence of pH on SXA. (A) Isoelectric focusing of native SXA. The left lane contains 0.5 mg SXA. The right lane indicates the positions of protein standards of known isoelectric point. (B) pH stability of SXA catalytic activity. SXA was preincubated at the indicated pH values and 25° C. for 60 min prior to analyzing for relative activity remaining (catalytic activity relative to SXA preincubated at 0° C. and pH 7.0). Standards deviations (±) of at least three determinations are indicated. The curve is drawn as a visual aid.

Figure 13:
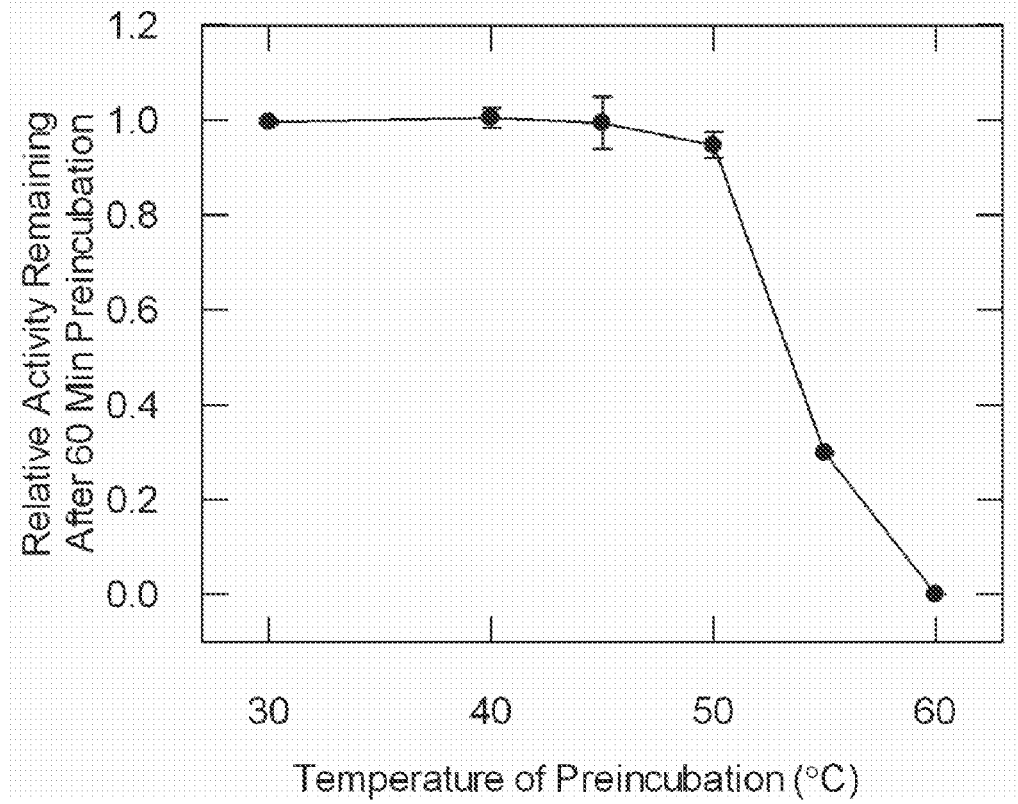

FIG. 13 shows the influence of temperature on SXA stability. SXA was preincubated at the indicated temperatures and pH 5.3 for 60 min prior to analyzing for relative activity remaining (catalytic activity relative to SXA preincubated at 0° C. and pH 7.0). Standards deviations (±) of at least three determinations are indicated. The curve is drawn as a visual aid.

FIG. 14 shows the protection of SXA from thermal inactivation at 55° C. by D-xylose. (A) Decay curves. Prior to analyzing for relative activity remaining, SXA was preincubated for the indicated times at pH 5.3 and 55° C. in the absence (○) or presence of D-xylose at 18.7 mM (●), 46.7 mM (□), 93.5 mM (■), and 280 mM (Δ). Progress curves were generated by fitting the data for each D-xylose concentration to equation 3: 0 mM ($k_{obs}$=0.0252±0.0020 min$^{-1}$), 18.7 mM ($k_{obs}$=0.0132±0.0010 min$^{-1}$), 46.7 mM ($k_{obs}$=0.00649±0.00087 min$^{-1}$), 93.5 mM ($k_{obs}$=0.00326±0.00056 min$^{-1}$), and 280 mM ($k_{obs}$=0.000917±0.00033 min$^{-1}$). (B) Dependence of first order decay rates on the concentration of D-xylose. The $k_{obs}$ values determined from the decay rates of panel A (±standard errors) are plotted versus the D-xylose concentration of each preincubation condition. The curve was generated by fitting the $k_{obs}$ values to equation: $K_{i(D-xylose)}$=17.6±1.8 mM.

FIG. 15 shows the protection of SXA from thermal inactivation at 55° C. by D-glucose. (A) Decay curves. Prior to analyzing for relative activity remaining, SXA was preincubated for the indicated times at pH 5.3 and 55° C. in the absence (○) or presence of D-glucose at 93.5 mM (●), 187 mM (□), 280 mM (■), and 374 mM (Δ). Progress curves were generated by fitting the data for each D-glucose concentration to equation 3: 0 mM ($k_{obs}$=0.0256±0.0015 min$^{-1}$), 93.5 mM ($k_{obs}$=0.00949±0.00069 min$^{-1}$), 187 mM ($k_{obs}$=0.00588±0.00077 min$^{-1}$), 280 mM ($k_{obs}$=0.00445±0.00081 min$^{-1}$), and 374 mM ($k_{obs}$=0.00336±0.00095 min$^{-1}$). (B) Dependence of first order decay rates on the concentration of D-glucose. The $k_{obs}$ values determined from the decay rates of panel A (±standard errors) are plotted versus the D-glucose concentration of each preincubation condition. The curve was generated by fitting the $k_{obs}$ values to equation 4: $K_{i(D-glucose)}$=56.1±0.8 mM.

FIG. 16 shows the protection of SXA from low pH inactivation at pH 4.0 by D-xylose. (A) Decay curves. Prior to analyzing for relative activity remaining, SXA was preincubated for the indicated times at pH 4.0 and 25° C. in the absence (●) or presence of D-xylose at 46.7 mM (o), 93.5 mM (■), and 280 mM (□). Progress curves were generated by fitting the data for each D-xylose concentration to equation 3: 0 mM ($k_{obs}$=0.0784±0.0023 min$^{-1}$), 46.7 mM ($k_{obs}$=0.0335±0.0008 min$^{-1}$), 93.5 mM ($k_{obs}$=0.0186±0.0004 min$^{-1}$), and 280 mM ($k_{obs}$=0.00614±0.00036 min$^{-1}$). (B) Dependence of first order decay rates on the concentration of D-xylose. The $k_{obs}$ values determined from the decay rates of panel A (±standard errors) are plotted versus the D-xylose concentration of each preincubation condition. The curve was generated by fitting the $k_{obs}$ values to equation 4: $K_{i(D-xylose)}$=31.7±2.8 mM.

FIG. 17 shows the protection of SXA from low pH inactivation at pH 4.0 by D-glucose. (A) Decay curves. Prior to analyzing for relative activity remaining, SXA was preincubated for the indicated times at pH 4.0 and 25° C. in the absence (o) or presence of D-glucose at 234 mM (●), 467 mM (□), and 701 mM (■). Progress curves were generated by fitting the data for each D-glucose concentration to equation 3: 0 mM ($k_{obs}$=0.0518±0.0037 min$^{-1}$), 234 mM ($k_{obs}$=0.0210±0.0016 min$^{-1}$), 467 mM ($k_{obs}$=0.0124±0.0007 min$^{-1}$), and 701 mM ($k_{obs}$=0.00748±0.00083 min$^{-1}$). (B) Dependence of first order decay rates on the concentration of D-glucose. The $k_{obs}$ values determined from the decay rates of panel A (±standard errors) are plotted versus the D-xylose concentration of each preincubation condition. The curve was generated by fitting the $k_{obs}$ values to equation 4: $K_{i(D-glucose)}$= 147±12 mM.

Figure 18:
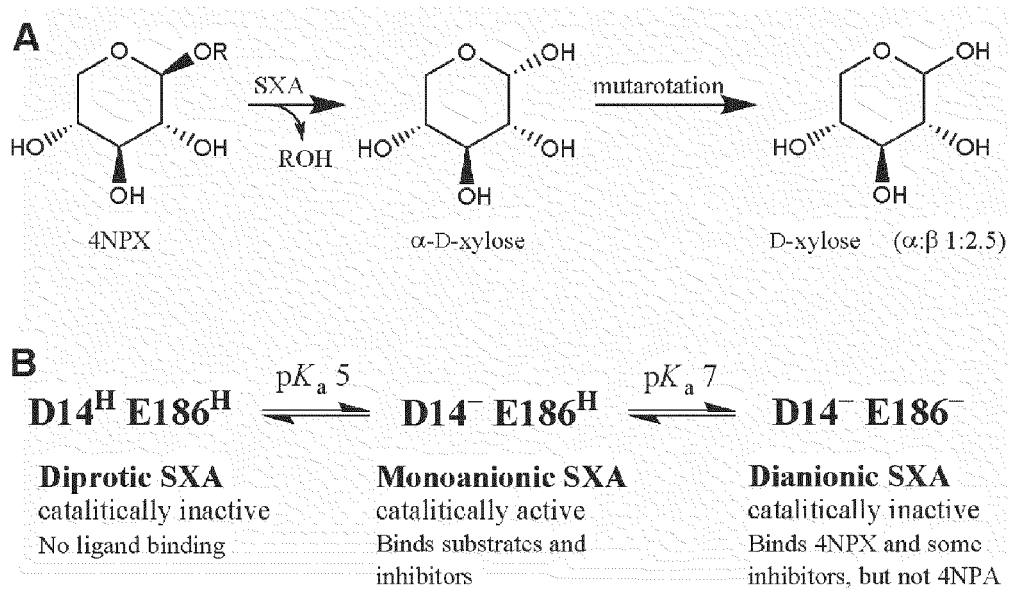

FIG. 18 shows the properties of SXA-catalyzed hydrolysis of 4-nitrophenyl-β-D-xylopyranoside (4NPX) as described in Example 3. (A) Stereochemistry. SXA catalyzes hydrolysis of 4NPX with inversion of anomeric configuration. Mutarotation, off the enzyme, converts α-D-xylose to its equilibrium mixture (α:β ratio of 1:2.5) with a half life of ~1 h (3). R=4-nitrophenyl. (B) Diprotic model. $pK_a$'s 5 and 7, assigned to catalytic base (D14) and catalytic acid (E186), respectively, govern catalysis and binding of ligands (3).

Figure 19A:
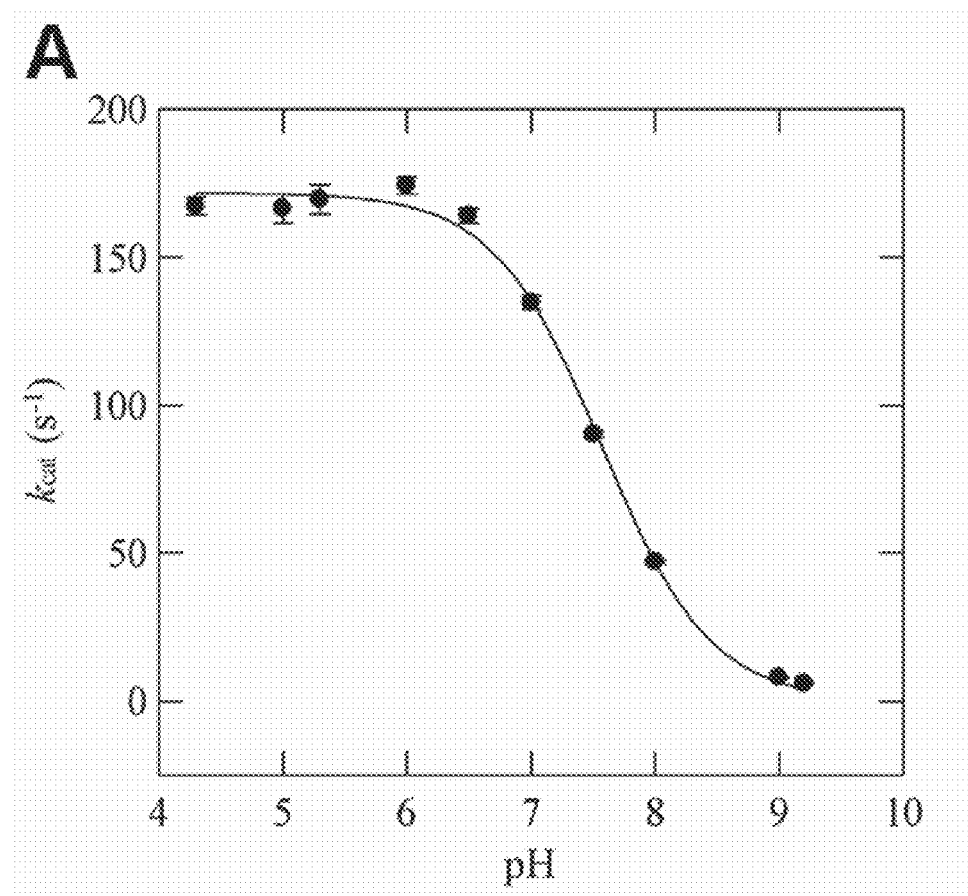
Figure 19B:
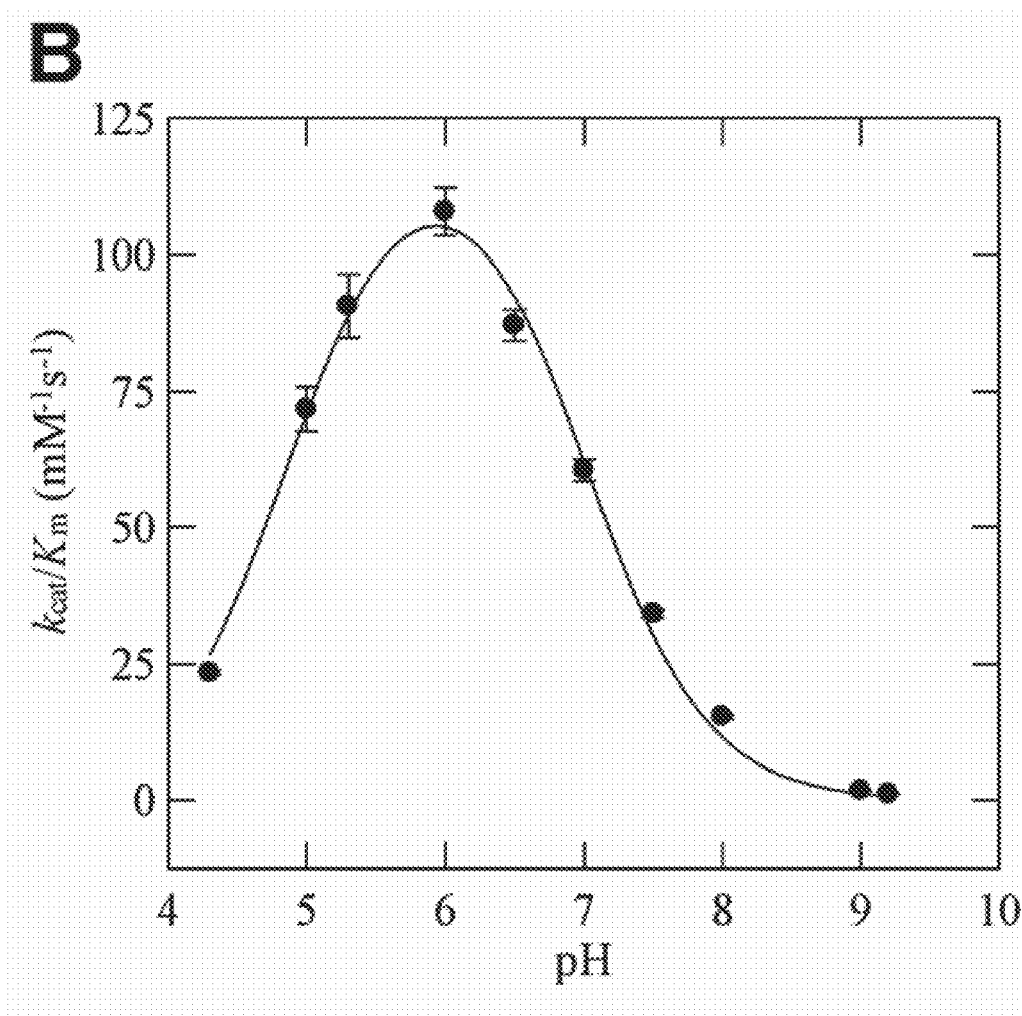
Figure 19C:
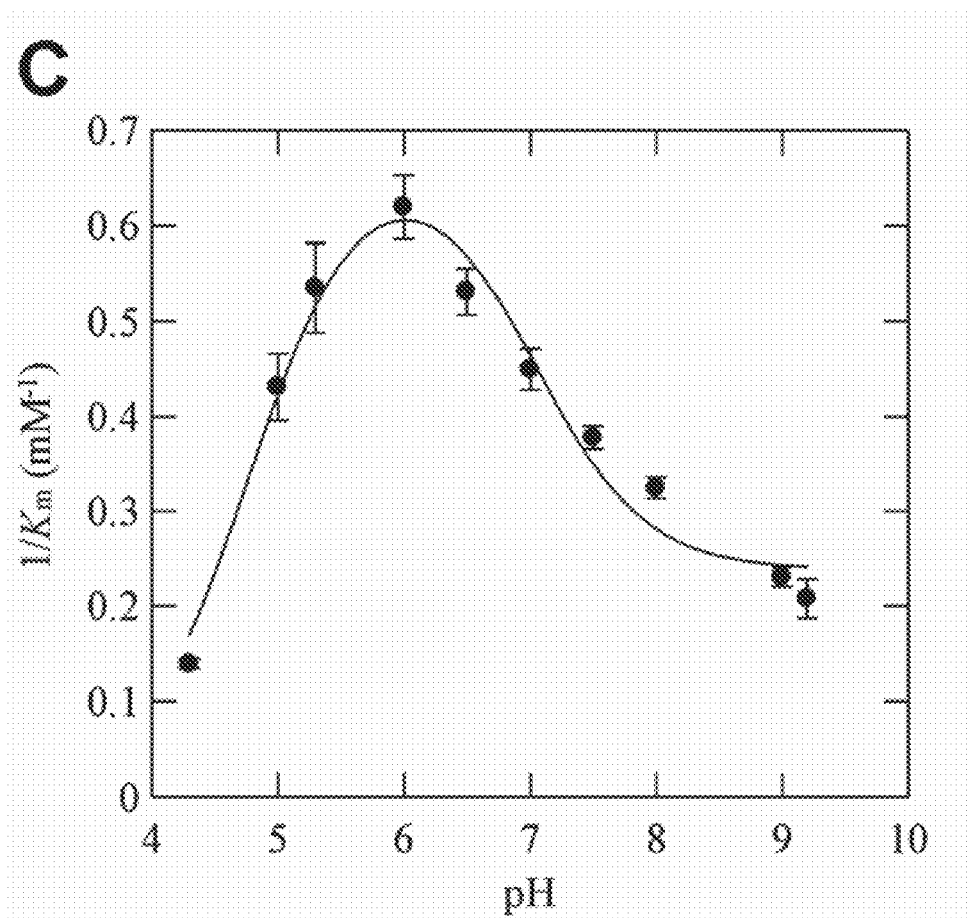

FIG. 19 shows the pH dependence of steady-state kinetic parameters for 1,4-β-D-xylobiose hydrolysis catalyzed by SXA at 25° C. as described in Example 3. Initial rates were determined from reactions in buffers of constant ionic strength (I=0.3 M) and kinetic parameters were determined by fitting initial-rate data to Eq. 1; standard errors (±) are indicated. (A) $k_{cat}$ versus pH. The curve was generated by fitting $k_{cat}$ values versus pH to Eq. 5: $pK_a$=7.57±0.03, pH-independent $k_{cat}$=172±2. (B) $k_{cat}/K_m$ versus pH. The curve was generated by fitting $k_{cat}/K_m$ values versus pH to Eq. 6: $pK_{a1}$=4.86±0.06, $pK_{a2}$=7.01±0.05, pH-independent $k_{cat}/K_m$=123±5. (C) $1/K_m$ versus pH. The curve was generated by fitting $1/K_m$ values versus pH to Eq. 7: $pK_{a1}$=4.78±0.11, $pK_{a2}$=7.03±0.17, middle limit $1/K_m$=0.682±0.048, upper limit $1/K_m$=0.238±0.022.

Figure 20A:
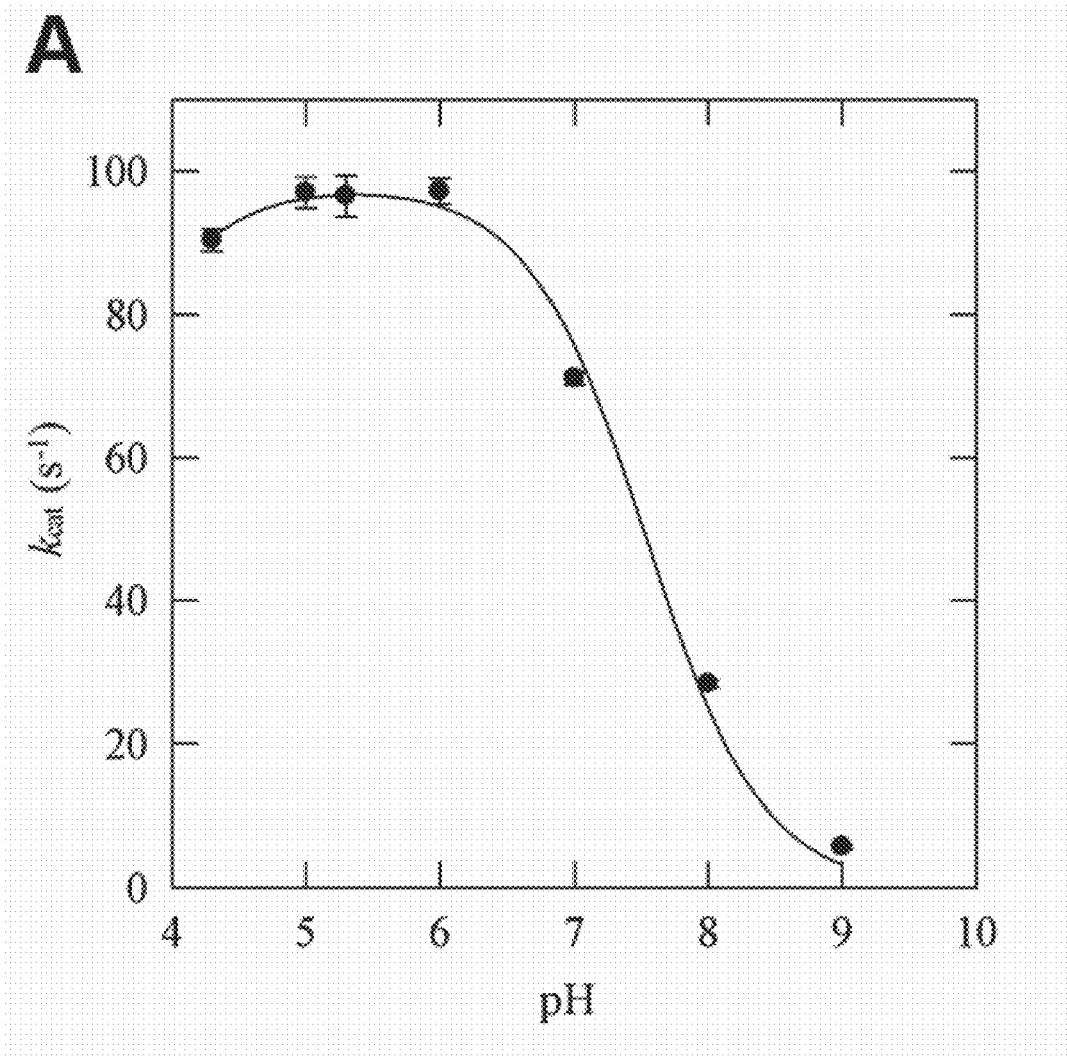
Figure 20B:
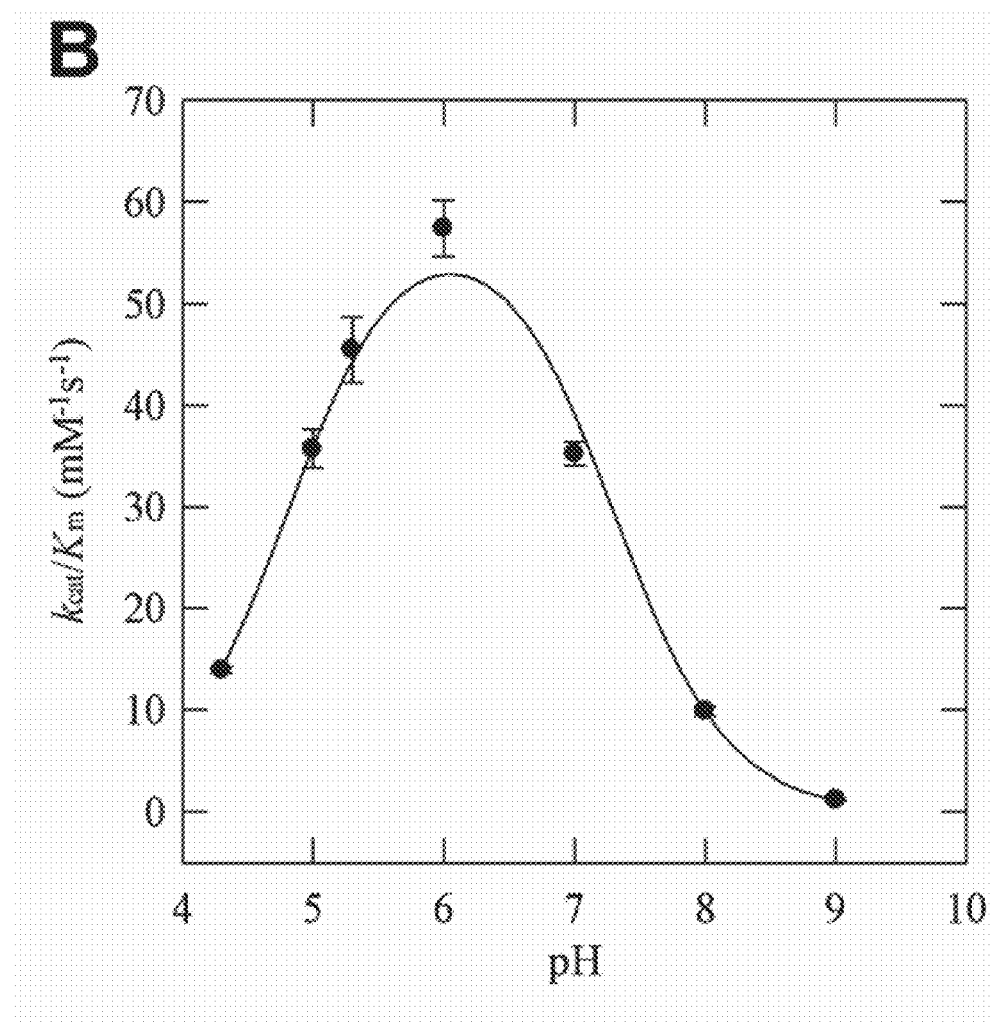
Figure 20C:
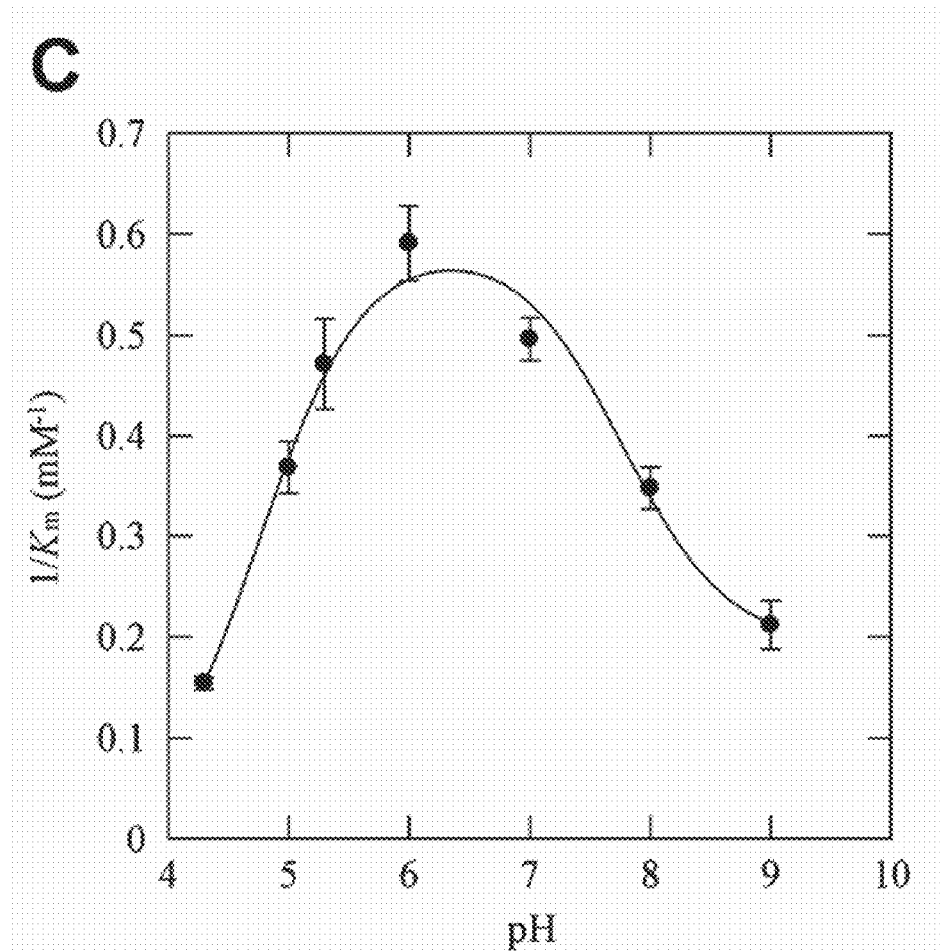

FIG. 20 shows the pH dependence of steady-state kinetic parameters for 1,4-β-D-xylotriose hydrolysis catalyzed by SXA at 25° C. as described in Example 3. Initial rates were determined from reactions in buffers of constant ionic strength (I=0.3 M) and kinetic parameters were determined by fitting initial-rate data to Eq. 1; standard errors (±) are indicated. (A) $k_{cat}$ versus pH. The curve was generated by fitting $k_{cat}$ values versus pH to Eq. 6: $pK_{a1}$=3.21±0.27, $pK_{a2}$=7.53±0.06, pH-independent $k_{cat}$=98.0±2.3. (B) $k_{cat}/K_m$ versus pH. The curve was generated by fitting $k_{cat}/K_m$ values versus pH to Eq. 6: $pK_{a1}$=4.80±0.06, $pK_{a2}$=7.30±0.04, pH-independent $k_{cat}/K_m$=58.9±3.3 mM$^{-1}$s$^{-1}$. (C) $1/K_m$ versus pH. The curve was generated by fitting $1/K_m$ values versus pH to Eq. 7: $pK_{a1}$=4.76±0.05, $pK_{a2}$=7.76±0.14, middle limit $1/K_m$=0.594±0.027, upper limit $1/K_m$=0.191±0.017.

Figure 21:
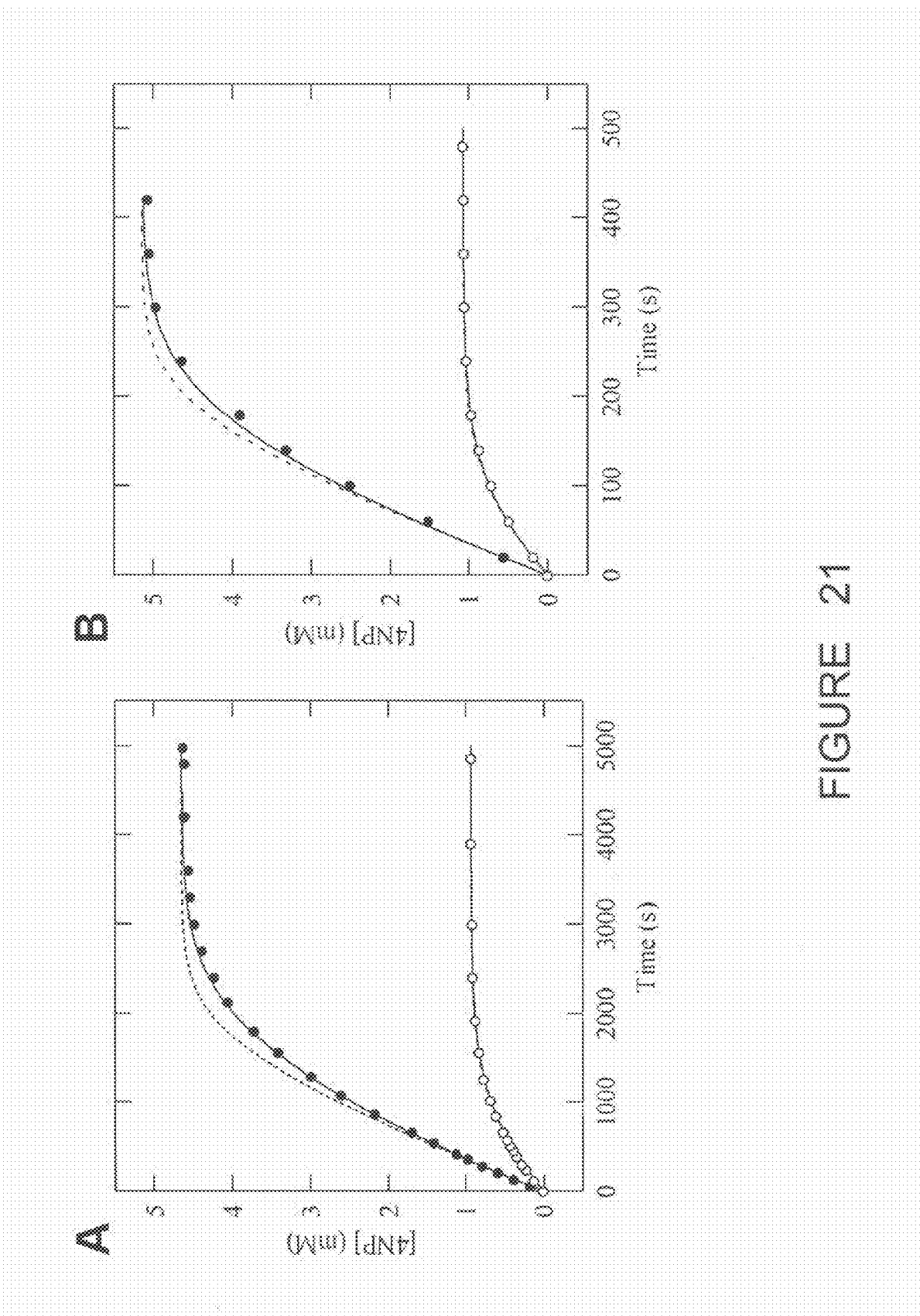

FIG. 21 shows the progress curves of 4NPX hydrolysis catalyzed by SXA. Reactions contained 100 mM succinate-NaOH, pH 5.3 at 25° C. as described in Example 3. [4NP] was determined spectrophotometrically. Curves were generated from the KINSIM calculations, assuming rapid equilibrium binding, with the indicated [enzyme] and [4NPX] and the following as inputs: E+S<=>E·S ($K_m^{4NPX}$=0.716±0.032 mM); E·S=>E+P+Q ($k_{cat}^{4NPX}$=32.1±0.5 s$^{-1}$); E·P<=>E+P ($K_i^{D-xylose}$=9.63±0.30 mM); E·Q<=>E+Q ($K_i^{4NP}$=6.28±0.55 mM); EP4NPX<=>EP+4NPX ($K_{is}^{D-xylose·4NPX}$=15.9±2.1 mM). Solid curves included all parameters as inputs in the KINSIM simulations; dotted curves excluded the $K_i^{4NP}$ term in the simulations. (A) Reactions were initiated by addition of enzyme to give initial reaction conditions of 52 nM SXA and 0.93 mM 4NPX (○) or 104 nM SXA and 4.65 mM 4NPX (●). (B) Reactions were initiated by addition of enzyme to give initial reaction conditions of 520 nM SXA and 1.07 mM 4NPX (o) or 1040 nM SXA and 5.15 mM 4NPX (●).

FIG. 22 shows the influence of D-xylose anomeric stereochemistry on inhibition of SXA-catalyzed hydrolysis of 4NPA at pH 5.3 and 25° C. as described in Example 3. Left syringe of stopped-flow instrument contained varied 4NPA concentrations in 100 mM succinate-NaOH, pH 5.3 at 25° C. Right syringe contained the indicated concentrations of SXA and D-xylose (or 1,4-β-D-xylobiose) in 100 mM succinate-NaOH, pH 5.3 and 25° C. Contents of the syringes were preincubated 6 min at 25° C., to achieve full conversion of 1,4-β-D-xylobiose to D-xylose, prior to initiating 20-s reactions (by mixing 50 μL from each syringe) and recording linear absorbance changes at 360 nm for determination of initial rates (v in moles 4NP produced per second per mole SXA protomer). (A) D-Xylose α:β ratio of 6:1. Right syringe of stopped flow contained 5.07 μM SXA and the following concentrations of 1,4-β-D-xylobiose: 0 (○), 8.6 mM (●), and 17.2 mM (▲). Lines were generated by fitting initial rate data to Eq. 2 (competitive inhibition): $K_i^{D-xylose}$=11.9±0.3 mM, $k_{cat}^{aNPA}$=2.78±0.01 s$^{-1}$, $k_{cat}/K_m^{4NPA}$=3.16±0.04 mM$^{-1}$s$^{-1}$, and $K_m^{4NPA}$=0.880±0.13 mM. (B) D-Xylose α:β ratio of 1:2.5. Right syringe of stopped flow contained 5.07 μM SXA and the following concentrations of D-xylose: 0 (○), 20 mM (●), 40 mM (□). Lines were generated by fitting initial rate data to Eq. 2 (competitive inhibition): $K_i^{D-xylose}$=11.8±0.3 mM, $k_{cat}^{4NPA}$=2.79±0.01 s$^{-1}$, $k_{cat}/K_m^{4NPA}$=3.10±0.04 mM$^{-1}$s$^{-1}$, and $K_m^{4NPA}$=0.900±0.013 mM.

Figure 23:
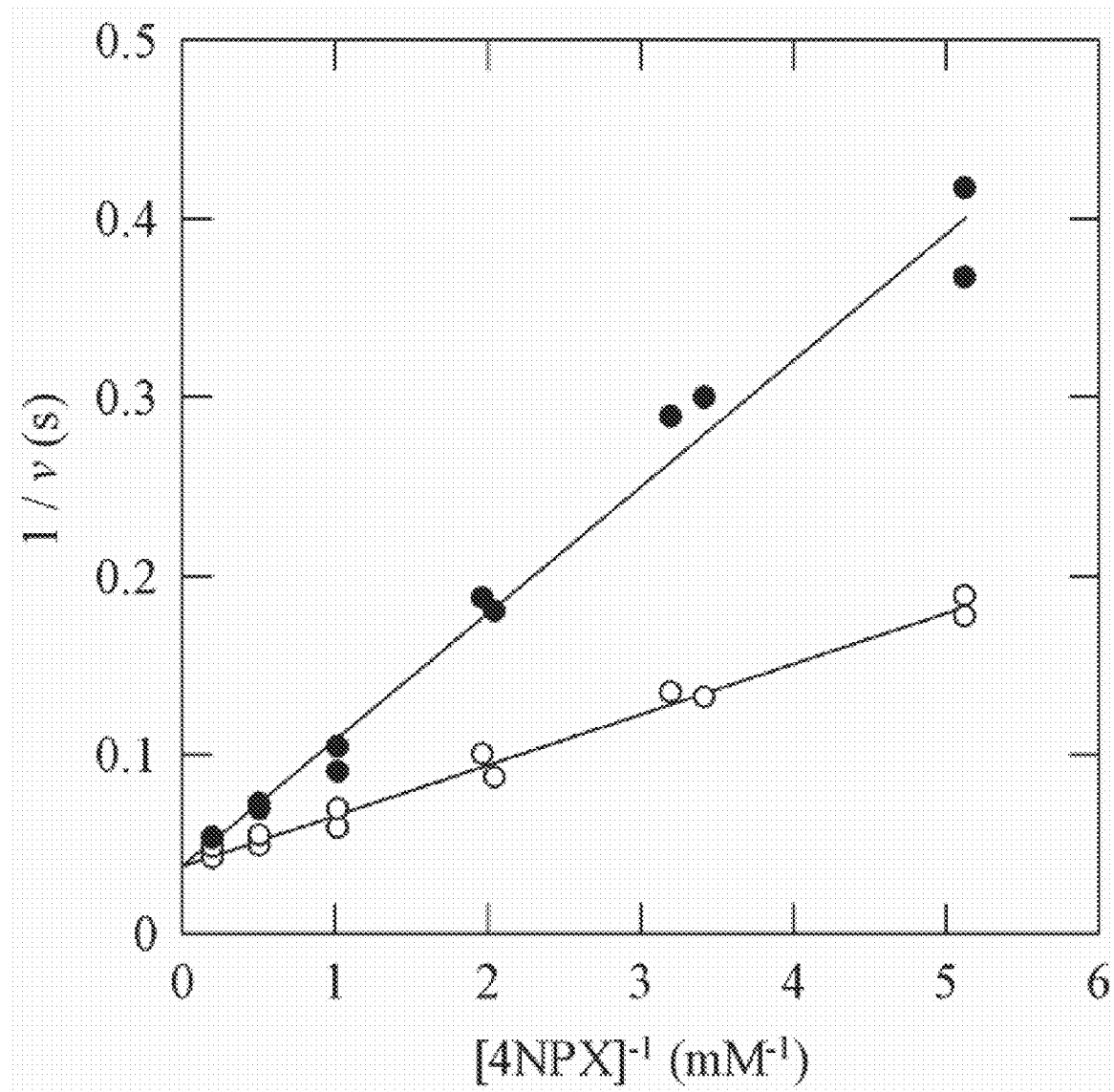

FIG. 23 shows the inhibition of SXA-catalyzed hydrolysis of 4NPX by 4-nitrophenol (4NP) at pH 5.3 and 25° C. as described in Example 3. Reactions contained 0 (○) or 9.4 mM 4NP (●), 7.09-33.8 nm SXA, and varied concentrations of 4NPX in 100 mM succinate-NaOH, pH 5.3 at 25° C. Concentrations of D-xylose produced were quantified by HPLC for determination of initial rates (v). Lines were generated by fitting initial rates to Eq. 2 (competitive inhibition): $K_i^{4NP}=6.28\pm0.55$ mM, $k_{cat}^{4NPX}=26.7\pm1.1$ s$^{-1}$, and $K_m^{4NPX}=0.758\pm0.059$ mM.

Figure 24:
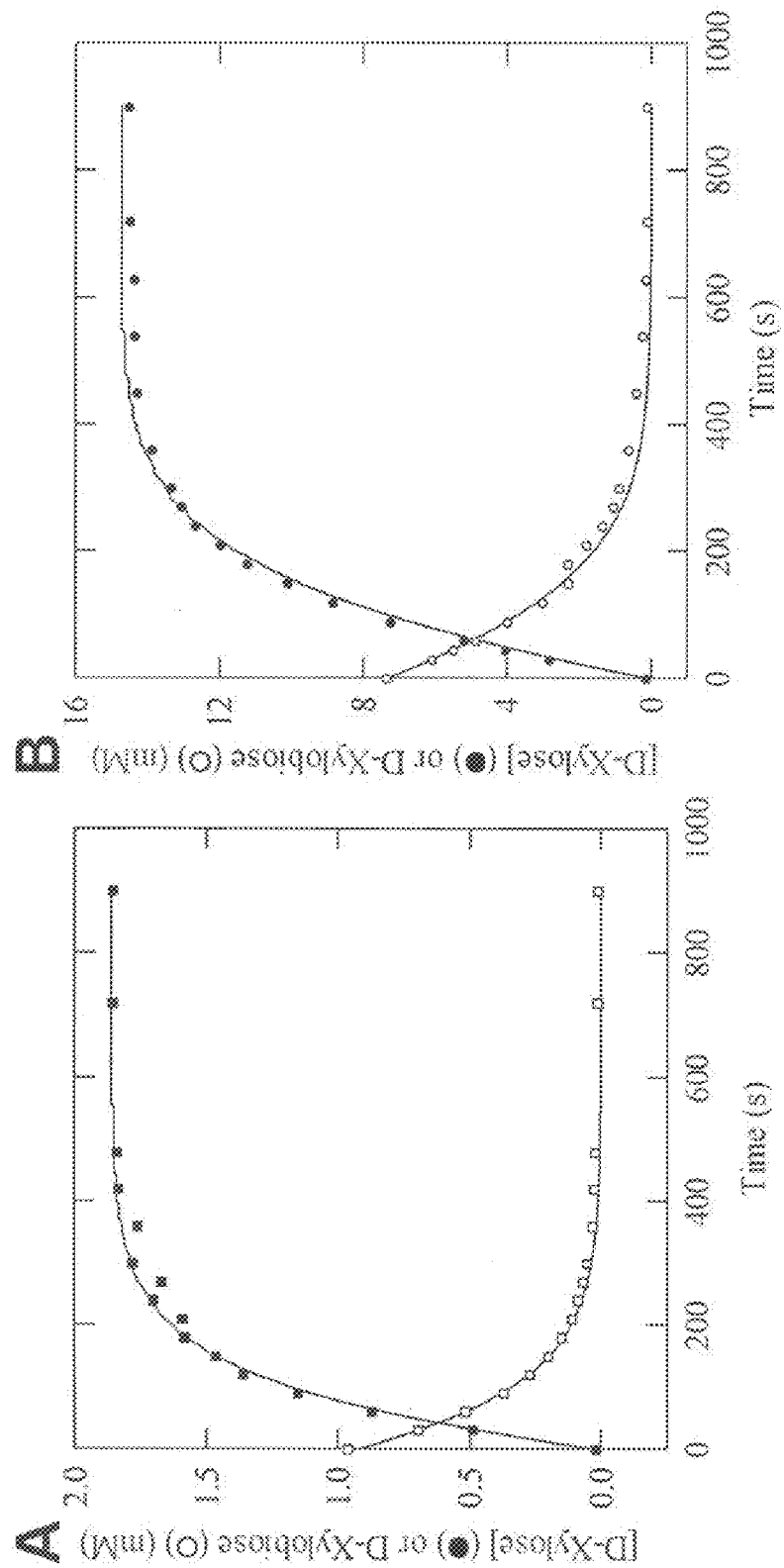

FIG. 24 shows the progress curves of 1,4-β-D-xylobiose (X2) hydrolysis catalyzed by SXA as described in Example 3. Reactions contained 100 mM succinate-NaOH, pH 5.3 at 25° C. Curves were generated from the KINSIM calculations, assuming rapid equilibrium binding, with the indicated [enzyme] and [X2] and the following as inputs: E+X2<=>E·X2 ($K_m$=2.06±0.08 mM); EX2=>E+X1+X1 ($k_{cat}^{X2}$=185±3 s$^{-1}$); E·X1<=>E+X1 ($K_i^{D-xylose}$=9.63±0.32 mM). Determined $K_m^{X2}$ and $k_{cat}^{X2}$ values at pH 5.3 at 25° C. are from Table 1 and determination of $K_i^{D-xylose}$ at pH 5.3 at 25° C. is described in the text. (A) Reaction contained 152 nM SXA, 0.922 mM X2, and 0.0146 mM X1 (contaminant of X2); concentrations of X1 (●) and X2 (○) were monitored by HPLC. (B) Reaction contained 303 nM SXA, 7.31 mM X2, and 0.111 mM X1 (contaminant of X2); concentrations of X1 (●) and X2 (○) were monitored by HPLC.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and some fungi, for example, the exogenous DNA may be maintained on an episomal element such as a plasmid. With respect to most eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

The enzyme of the invention is β-D-xylosidase (E.C. 3.2.1.37 and also referred to herein as SXA) within the glycoside hydrolase family 43, which catalyzes the hydrolysis of β-1,4-glycosidic bonds linking D-xylose residues in xylooligosaccharides with the release of xylose therefrom. The activity of the enzyme, $k_{cat}$, is surprising high toward natural xylooligosaccharides and natural xylose-containing substrates (xylans; arabinoxylans), being more than 10-fold higher than other reported β-D-xylosidases at their optimal pH. This is particularly surprising because the β-D-xylosidase of this invention and other reported β-D-xylosidases can have similar activity toward synthetic substrates such as 4NPX. In the course of our initial investigation of enzyme properties described in Example 1, the optimal activity of the enzyme was determined at a pH of between about 4.5 and about 7.7, particularly about 6.0. Specifically, the β-D-xylosidase was initially found to exhibit the following $k_{cat}$ values for catalysis toward representative natural xylooligosaccharides: approximately 410 $sec^{-1}$ for 1,4-β-D-xylobiose (X2), approximately 170 $sec^{-1}$ for 1,4-β-D-xylotriose (X3), approximately 150 $sec^{-1}$ for 1,4-β-D-xylotetraose (X4), approximately 150 $sec^{-1}$ for 1,4-β-D-xylopentaose (X5), and approximately 100 $sec^{-1}$ for 1,4-β-D-xylohexaose (X6), all measured at a pH of 5.3 and a temperature of 25° C. (Example 1). However, as described in Example 3, we have more recently developed an improved technique for measuring the kinetic parameters of the β-D-xylosidase of this invention for its catalysis toward the same natural oligosaccharides described above, wherein the reaction mixtures are quenched with an equal volume of 0.2 M sodium phosphate, pH 11.3 at 0° C. (so that quenched reaction mixtures were at a pH of 10.5 to 11). When measured using this improved technique, the β-D-xylosidase exhibited the following $k_{cat}$ values for catalysis toward representative natural xylooligosaccharides: approximately 185 $sec^{-1}$ for 1,4-β-D-xylobiose (X2), approximately 95.1 $sec^{-1}$ for 1,4-β-D-xylotriose (X3), approximately 91.6 $sec^{-1}$ for 1,4-β-D-xylotetraose (X4), approximately 77.2 $sec^{-1}$ for 1,4-β-D-xylopentaose (X5), and approximately 81.5 $sec^{-1}$ for 1,4-β-D-xylohexaose (X6). Other characteristics of the enzyme include pKa values for catalysis of approximately 5.0 and 7.2 based on the kinetic parameter $k_{cat}/K_m$ for the substrates 4-nitrophenyl-β-D-xylopyranoside (4NPX), 4-nitrophenyl-α-L-arabinofuranoside (4NPA), 1,4-β-D-xylobiose (X2), and 1,4-β-D-xylotriose (X3), and an isoelectric point of approximately 4.4. The enzyme also has a molecular weight of approximately 60 kiloDaltons as determined by SDS-PAGE, is stable at temperatures up to about 55° C., lacks transglycosylation activity which would impair the hydrolysis reaction, and also catalyzes the hydrolysis of arabinose side chains from arabinoxylooligosaccharides which occur in the hemicelluloses of some plant species (i.e., arabinofuranosidase activity).

The β-D-xylosidase used in this invention was originally isolated from the ruminal bacterium *Selenomonas ruminantium* GA192 as described by Cotta (1993, Applied and Environmental Microbiology, 59:3557-3563). *S. ruminantium* GA192 is available from The American Type Culture Collection (10801 University Blvd., Manassas, Va., USA) as deposit accession no. ATCC 12561. The enzyme was subsequently cloned into *E. coli* and sequenced, and the gene sequence and the predicted amino acid sequence of the enzyme was deposited in GenBank under accession no. AF040720 and AAB97967, respectively, as described by Whitehead and Cotta (2001, Current Microbiology, 43:293-298), the contents of which are incorporated by reference herein. The gene sequence and the predicted amino acid sequence of the β-D-xylosidase are also shown in FIGS. 1 and 2, respectively.

One microorganism for the production of the β-D-xylosidase is the above-mentioned *Selenomonas ruminantium* GA192, although, in the preferred embodiment, recombinant bacteria transformed with the *S. ruminantium* GA192 gene encoding the enzyme, particularly *E. coli*, are used. Alternatively, the process may utilize β-D-xylosidase enzyme having at least 90%, preferably at least 95%, homology with the amino acid sequence deposited in GenBank under accession no. AAB97967, and which enzyme is still capable of hydrolyzing xylose-containing plant material to produce xylose, and has a $k_{cat}$ value for catalysis of approximately 185 $sec^{-1}$ for 1,4-β-D-xylobiose (X2) when measured at a pH of 5.3 and a temperature of 25° C. The enzyme should also preferably have $k_{cat}$ values for catalysis of approximately 95.1 $sec^{-1}$ for 1,4-β-D-xylotriose (X3), approximately 91.6 $sec^{-1}$ for 1,4-β-D-xylotetraose (X4), approximately 77.2 $sec^{-1}$ for 1,4-β-D-xylopentaose (X5), and approximately 81.5 $sec^{-1}$ for 1,4-β-D-xylohexaose (X6), all measured at a pH of 5.3 and a temperature of 25° C.

Two polypeptides are said to be "identical" if the sequence of amino acid residues, respectively, in the two sequences is the same when aligned for maximum correspondence as described below. Sequence comparisons between two (or more) polypeptides are typically performed by comparing sequences of the two sequences over a segment or "comparison window" to identify and compare local regions of sequence similarity. Optimal alignment of sequences for comparison may be conducted by the local homology algorithm of Smith and Waterman (1981, Adv. Appl. Math., 2:482), by the homology alignment algorithm of Needleman and Wunsch (1970, J. Mol. Biol., 48:443), by the search for similarity method of Pearson and Lipman [1988, Proc. Natl. Acad. Sci. (U.S.A.) 85:2444], by computerized implementations of these algorithms [(GAP, BESTFIT, FASTA, and TFASTA in the Wisconsin Genetics Software Package, Genetics Computer Group (GCG), 575 Science Dr., Madison, Wis.], or by inspection. "Percentage of sequence identity" is determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "substantial identity" of amino acid sequences for these purposes normally means sequence identity of at least 90%, and most preferably at least 95% compared to a reference sequence. The reference sequence herein is the predicted amino acid sequence of the β-D-xylosidase produced by *Selenomonas ruminantium* GA192 deposited in GenBank under accession no. AAB97967. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Techniques for the preparation of β-D-xylosidase having modified amino acid sequences from that of the enzyme produced by *S. ruminantium* GA192 (GenBank accession no. AAB97967) are described in Example 1, hereinbelow.

The DNA sequence of the β-D-xylosidase gene produced by *S. ruminantium* GA192 (GenBank accession no. AF040720) can be used to prepare recombinant DNA molecules by cloning into any suitable vector. A variety of vector-host cell expression systems may be employed in practicing the present invention. Strains of bacteria, such as *Escherichia coli* such as described by Whitehead and Cotta (2001, ibid) and Example 1 hereinbelow are particularly useful in producing the β-D-xylosidase used in the practice of the invention. However, the novel invention described here can be applied with numerous hosts that would desirable. Host strains may be of bacterial, fungal, or yeast origin. Factors that can be considered in choosing host strains include substrate range, hardiness, sugar tolerance, salt tolerance, temperature tolerance, pH tolerance, and lactate tolerance. Ascertaining the most appropriate host-vector system is within the skill of the person in the art.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the β-D-xylosidase of the invention not fused to any heterologous polypeptide), or alternatively, fusion vectors (i.e., those producing the β-D-xylosidase fused to a vector encoded polypeptide). The fusion proteins would of course vary with the particular vector chosen.

Within each specific vector, various sites may be selected for insertion of the isolated DNA sequence. These sites are usually designated by the restriction enzyme or endonuclease that cuts them.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences comprising the β-D-xylosidase gene may be inserted into the desired vector by known techniques. If, however, the vector is to serve as an expression vector, the vector should have a promoter, and the DNA sequence should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eucaryotic). Alternatively, any or all of the above control sequences may be ligated to the coding sequence prior to insertion into the vector.

DNA constructs may be introduced into the appropriate host by numerous methods described in the technical and scientific literature. Transformation of bacteria or yeast may be performed using standard techniques described in Maniatis et al., supra. Techniques for transforming filamentous fungi may include those described by Goosen et al. [Handbook for Applied Mycology, Arora, Elander & Mukerji, eds. (1992) pp. 151-195] and May et al. [Applied Molecular Genetics of Filamentous Fungi, Kinghorn and Turner, eds. (1992) pp. 1-27]. Transformations with *E. coli* are described in Example 1.

In general, linear or circular DNA constructs may be introduced into the host by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed host. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct.

The DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

Production of the β-D-xylosidase may be accomplished by culture of any of the aforementioned microorganisms by conventional techniques under appropriate anaerobic or aerobic conditions that are effective to promote growth and β-D-xylosidase production. Any number of well-known liquid or solid culture media may be used, although growth on liquid media is preferred. Without being limited thereto, particularly preferred culture media include LB medium, Brain-Heart Infusion Broth or Trypticase Soy Broth. Similarly, a variety of conventional carbon sources will support growth and production of the enzyme and may be used herein. The presence of xylose and xylooligosaccharides in the culture medium is not essential for production of the enzyme, although optimal β-D-xylosidase production is achieved by their addition when using *Selenomonas ruminantium*. The precise degree of enhancement is variable and is dependent upon the particular microorganism used. The amount of xylose and xylooligosaccharides added to the media is not critical and may be readily determined by the practitioner skilled in the art.

Upon completion of the fermentation, typically between 6 to 96 hours, β-D-xylosidase may be isolated or separated from the microorganisms using techniques conventional in the art, such as by centrifugation followed by cell breakage. Suitable techniques for concentration and/or purification of the enzyme may be readily determined by the practitioner skilled in the art and include, for example, dialysis, ion-exchange chromatography, and HPLC size-exclusion chromatography and electrophoresis, particularly polyacrylamide-gel-electrophoresis (PAGE). Using these techniques, β-D-xylosidase may be recovered in pure or substantially pure form. It is also envisioned that the enzyme may be formulated in conjunction with a suitable inert carrier or vehicle as known in the art. The skilled practitioner will recognize that such carriers must be compatible with the enzyme.

The β-D-xylosidase may be used alone, or preferably in combination with one or more other xylanolytic enzymes, for the hydrolysis of D-xylose containing plant materials such as hemicelluloses and xylooligosaccharides. Examples of hemicellulosic materials which may be treated in accordance with this invention include lignocellulosic biomass such as gardening and agricultural residues (straw, hulls, stems, stalks), grasses, corn fiber, corn stover, corn cobs, wood, including sawdust and wood chips, forestry waste, municipal solid wastes (paper, cardboard, yard trash, and wood products), wastes from the pulp and paper industry, herbaceous crops, plant material hydrolysates, and particularly sugarcane bagasse, wheat, wheat straw, and switchgrass. Specific applications of the enzyme include, but are not limited to, the saccharification of these xylose-containing plant materials to the fermentable sugar xylose which may be optionally subsequently fermented to secondary products such as ethanol, butanol, xylitol, lactic acid or acetic acid, the treatment of plant materials for use as animal feed, delignification of pulp, and the therapeutic cleavage of xylose residues off the polysaccharides on the surface of bacterial pathogens to reduce their adhesion to animal cell surfaces.

When used alone, the enzyme effectively cleaves the substrate with the release of D-xylose therefrom. The resultant xylose and/or hydrolyzed substrate may be recovered and subsequently used in a variety of applications as described above, or they may be subjected to additional treatments. Although the enzyme is effective for hydrolyzing xylooligosaccharides in general, optimal activity is exhibited against shorter chain xylooligosaccharides, particularly those having two to six xylose units. Thus, where a greater degree of hydrolysis or saccharification is required, particularly for the treatment of hemicelluloses, the β-D-xylosidase is preferably used in combination with one or more xylanolytic enzymes. A variety of xylanolytic enzymes are suitable for use herein, and the specific enzyme selected will vary with the substrate and the desired degree of hydrolysis. Without being limited thereto, particularly preferred enzymes which may be used in combination with β-D-xylosidase include xylanases to hydrolyze the xylan to smaller chains, including endoxylanase (endo-1,4-β-xylanase) which hydrolyzes the linear polyxylose chain of xylans and arabinoxylans to xylooligosaccharides and xylobiose, galactosidase, α-L-arabinofuranosidase, and other xylanolytic enzymes which are effective for removing side groups from polymeric xylans such as ferulic acid esterase, coumaric acid esterase, acetic acid esterase, and α-glucuronidase. Hydrolysis of the hemicellulosic materials to xylose may be effected by use of the β-D-xylosidase alone, although it is also envisioned that it may be used in combination with one or both of β-xylanase and α-L-arabinofuranosidase.

The source of the xylanolytic enzymes is not critical, and suitable enzymes may be obtained from commercial preparations, or they may be produced by culture of well known microorganisms, most notably *Aureobasidium, Thermomonospora*, and *Streptomyces* species, such as described by Sunna and Antranikan (1997, Critic. Rev. in Biotech., 17(1):39-67), Ball and McCarthy (1988, J. Gen Microbiol., 134:2139-2147) or Bachmann and McCarthy (1991, Appl. Environ. Microbiol., 57:2121-2130), the contents of each of which are incorporated by reference herein.

Hydrolysis of the hemicellulosic materials may be accomplished using conventional techniques. A number of processes have been described for the enzymatic hydrolysis of lignocellulosic materials generally using cellulolytic and/or xylanolytic (hemicellulase) enzymes, and are suitable for use with the enzymes described herein as well. These include, but are not limited to, techniques described by Hespell et al. (1997, Appl. Biochem. Biotechnol., 62:87-97), and techniques reviewed by Wright (1988, Chem. Engin. Progress, 84(8):62-74), the contents of each of which are incorporated by reference herein.

In general, the xylose-containing plant material is contacted with catalytically effective amounts of the β-D-xylosidase and optional xylanolytic enzymes in an aqueous solution and under conditions effective to hydrolyze xylose from the substrate. The substrate may be treated with the enzymes in sequence (consecutively), although optimal hydrolysis of the entire substrate may require simultaneous (concurrent) treatment with the xylanases or other enzymes.

The actual amount of the enzymes and the conditions for the reaction will vary with the substrate and the source of the xylanolytic enzymes, and may be readily determined. Suitable pH and temperature conditions for the β-D-xylosidase are between about 4.5 and about 7.7, and between about 15 and about 55° C., respectively, with a pH between about 4.5 and about 6.0 and a temperature between about 15 and about 50° C. being preferred. However, optimal conditions for the xylanolytic enzymes may be different. Typically, for optimal xylanase activity, the pH will be between about 4.0 to 9.0, and the temperature will be between about 40 to 80° C. (Sunna and Antranikian, 1997, ibid); and Ball and McCarthy, 1988, ibid).

The process may be conducted with agitation in conventional batch, fed-batch, or continuous reactor systems, such as described by Wang et al. (1979, Fermentation and Enzyme Technology, John Wiley & Sons, New York, pp. 339-343). Furthermore, the enzymes may be in solution or, in the alternative, immobilized onto a conventional solid support. A number of techniques for the immobilization of enzymes have been previously reported and may be used with the enzyme of this invention as well. Examples of suitable immobilization techniques and supports include, but are not limited to, those described by Woodward and Capps (1992, Appl. Biochem. Biotechnol., 34/35:341-347), Karube et al. (1977, Biotech. Bioeng., 19:1183-1191), Woodward and Zachry (1982, Enzyme Microb. Technol., 4:245-248), Srinivasan and Bumm (1974, Biotech. Bioeng., 16:1413-1418), Bissett and Sternberg (1978, Appl. Environ. Microbiol., 35:750-755), Venardos et al. (1980, Enzyme Microb. Technol., 2:112-116), and Sundstrom et al. (1981, Biotechnol. Bioeng., 23:473-485), the contents of each of which are incorporated by reference herein. If the enzymes are in solution, they may be optionally recovered from the product stream for recycle, such as described by Lee et al. (1995, Biotechnol. Bioeng., 45:328-336), the contents of which are also incorporated by reference herein.

This invention may be practiced using lignocellulosic biomass as the substrate. While it is envisioned that this biomass may be treated with the enzymes directly, the rate of hydrolysis and fermentable sugar yields will be significantly reduced due to the complex structure of these molecules preventing enzyme access to the hemicellulose. Consequently, in the preferred embodiment, the lignocellulosic biomass is pretreated to break down the lignin-hemicellulose matrix, solubilizing the hemicellulose and/or increasing the surface area of hemicellulose accessible to the enzymes. The advantages of pretreating lignocellulosic biomass in this manner have been widely recognized in the art, and a variety of different mechanical and chemical pretreatments have been described. Examples of pretreatments which may be suitable for use herein include, but are not limited to treatment with dilute or concentrated acid (e.g., HCl, $H_2SO_4$, or $H_3PO_4$) treatment with alkali (e.g., NaOH, or $NH_4OH$) or alkaline peroxide, ammonia fiber (or freeze) explosion (AFEX), treatment with organic solvents (e.g., ethanol, methanol, ethylene glycol, butanol, phenol), autohydrolysis by steam explosion, acid steam ($SO_2$) treatment, treatment with hot, compressed liquid water, or pressure cooking. Mechanical pretreatments which may be used include ball or roll milling, grinding, shearing, or extruding. A detailed review of the mechanisms and conditions for these different pretreatments is described by McMillan (Pretreatment of Lignocellulosic Biomass, In: *Enzymatic Conversion of Biomass for Fuels Production*, Himmel et al. [ed.], American Chemical Soc., Washington, D.C., 1994, pp. 293-324), Weil et al. (1994, Enzyme Microb. Technol., 16:1002-1004), and Wright (1988, ibid), the contents of each of which are incorporated by reference herein.

The above-described pretreatments vary considerably in their effectiveness and in the physical and chemical properties of the resultant, treated substrates. For instance, acid pretreatments often produce furfural or other compounds which are toxic to many microorganisms. Before the hydrolyzed substrate may be subjected to any subsequent fermentation, these toxic compounds must be removed, such as by vacuum distillation, and the acid must be neutralized (Dunning and Lathrop, 1945, Indust. Eng. Chem., 37:24-29). Furthermore, the pretreatment itself may result in the hydrolysis of a portion of the hemicellulose to oligomers, or the saccharides xylose and L-arabinose. The actual degree of hydrolysis will vary greatly with the particular pretreatment selected. For instance, hemicellulose hydrolysis resulting from pretreatment with ammonia freeze explosion, alkali, or organic solvents is typically very small. In contrast, pretreatment of lignocellulosic substrates with acids, particularly concentrated acids and/or acids at high temperatures, generally hydrolyzes a large portion of the hemicellulose to sugars. Acid pretreatments and other pretreatments (i.e. steam explosion) can result in the loss of large amounts of sugars.

In view of the differences between the pretreatments, the selection of the optimal procedure will vary with the particular substrate and the desired application or further treatment of the hydrolyzed substrate and sugars. However, pretreatments which are typically preferred for use herein include treatment with organic solvents (e.g., ethanol, methanol, ethylene glycol, butanol, phenol), treatment with alkali (e.g., NaOH, $NH_4OH$, or alkaline peroxide), and ammonia fiber (or freeze) explosion (AFEX). Low temperature AFEX pretreatment as described by Bothast et al. (Conversion of Corn Fiber to Ethanol, In: *Liquid Fuel and Industrial Products from Renewable Resources*, Cundiff et al. [ed.], The American Society for Agricultural Engineers, St. Joseph, Mich., 1996, pp. 241-252), Hespell et al. (1997, ibid) and DeLaRosa et al. (1994, Appl. Biochem. Biotechnol., 45/46:483-497), the contents of each of which are incorporated by reference herein, is particularly preferred.

At the conclusion of the pretreatment of the lignocellulosic material, the solid residue will typically contain cellulose and lignin. All or a portion of the hemicellulose may be solubilized into the liquid phase, as in the case of chemical pretreatments such as AFEX, acid, base, solvent, or steam treatments, or it may remain entirely in the solid phase as in the case of mechanical treatments. The cellulose containing fraction may be retained for enzymatic conversion to glucose as described by Saha and Bothast (U.S. Pat. No. 5,747,320), Olsson and Hahn-Hägerdal (1996, Enzyme Microbial Technol., 18:312-331), or Wright (1988, ibid), the contents of each of which are incorporated by reference herein.

The hemicellulose containing fraction from the pretreatment is retained for enzymatic conversion to xylose using the β-D-xylosidase of this invention as described above. Following completion of this enzymatic hydrolysis, the xylose may be recovered and stored, or it may be subsequently fermented to ethanol or other secondary products using conventional techniques.

Processes for the fermentation of xylose are known in the art, and are suitable for use herein. In brief, the hydrolyzate containing the xylose from the enzymatic reaction is contacted with an appropriate microorganism under conditions effective for the fermentation of the xylose to ethanol or other product. This fermentation may be separate from and follow the enzymatic hydrolysis of the xylose containing substrate (sequentially processed), or the hydrolysis and fermentation may be concurrent and conducted in the same vessel (simultaneously processed). This concurrent hydrolysis and fermentation process provides the added advantage of avoiding the accumulation of inhibitory monosaccharides and is preferred. By including the fermenting organism in the enzymatic saccharification reaction the carbon flow is driven toward ethanol, thereby avoiding accumulation of monosaccharides which could inhibit the saccharification reaction. If the fermentation is conducted sequentially, following the enzymatic saccharification, high concentrations, above 2 M, of monosaccchariades such as D-glucose ($K_i$=27±0.4 mM), D-xylose ($K_i$=4.2±0.1 mM), and L-arabinose ($K_i$=20±0.5 mM) may accumulate and complex with the β-D-xylosidase/α-L-arabinofuranosidase, inhibiting enzyme activity toward the end of the saccharification. In contrast, if the saccharification and fermentation are conducted concurrently, the enzyme is only weakly inhibited by ethanol ($K_i$=1.04±0.08 M at pH 7.0). Any ethanologenic microorganism effective for utilizing xylose is suitable for use herein, wherein ethanologenic refers to the ability of the microorganism to produce ethanol from a carbohydrate, in this case, xylose. Without being limited thereto, a suitable microorganism for the production of ethanol is recombinant *Escherichia coli* FB5R described by Dien et al. (2000, Appl. Biochem Biotechnol., 84-86, 181-196, the contents of which are incorporated by reference herein). Without being limited thereto, other suitable microorganisms include recombinant *Bacillus* species such as described by Ingram et al. (U.S. Pat. No. 6,849,434), *Thermobacter mathranii* as described by Ahring et al. (U.S. Pat. No. 6,555,350), *Zymomonas* species such as *Z. mobilis*, and the yeast *Pichia stipitis* as disclosed by Shi et al. (U.S. Pat. No. 6,391,599) and Keller, Jr. et al. (U.S. Pat. No. 6,498,029), the contents of each of which are incorporated by reference herein. Still other suitable microorganisms include *Saccharomyces cerevisiae* for fermentation of xylose to xylitol, transformed yeast strains as described by Porro et al. (U.S. Pat. No. 7,049,108) for producing lactic acid, and *Clostridium acetobutylicum* as described by Levy (U.S. Pat. No. 4,568,643) for producing butanol, and *Acetobacter* species for producing acetic acid. The contents of which each of these patents are incorporated by reference herein. Details of the fermentation techniques and conditions have been described, for example, by Beall et al. (1991, Biotechnol. Bioengin., 38:296-303) and Moniruzzaman et al. (1996, Biotechnol. Lett., 18:985-990), the contents of each of which are incorporated by reference herein as well. In the preferred embodiment, the xylose may also be fermented to ethanol as described by Wyman (1994, Bioresource Technol., 50:3-16) or Olsson and Hahn-Hägerdal (1996, ibid), the contents of each of which are incorporated by reference herein.

After completion of the fermentation, the ethanol or butanol, xylitol, lactic acid or acetic acid may be recovered and optionally purified or distilled. Solid residue containing lignin may be discarded or used as animal feed or burned as a fuel.

The following examples are intended only to further illustrate the invention and are not intended to limit the scope of the invention which is defined by the claims.

Example 1

Materials and General Methods

Buffers, 4-nitrophenol (4NP), 4NP glycosides, and D-xylose (X1) were obtained from Sigma-Aldrich. 1,4-β-D-Xylobiose (X2), 1,4-β-D-xylotriose (X3), 1,4-β-D-xylotetraose (X4), 1,4-β-D-xylopentaose (X5), 1,4-β-D-xylohexaose (X6), and 1,5-α-L-arabinobiose (A2) were from Megazyme. 4-Nitrophenyl-β-D-xylobioside (4NPX2) was a generous gift from Dr. Peter Biely. Water was purified through a Milli-Q unit (Millipore). All other reagents were reagent grade and high purity. Kinetic viscosity measurements were made at 25° C. using a Cannon-Fenske tube (Kimble); rates of sucrose solutions were divided by rates of water to yield relative viscosity ($\eta/\eta_o$). A Cary 50 Bio UV-Visible spectrophotometer (Varian), equipped with a thermostatted holder for cuvettes, was used for spectral and kinetic determinations. A model SX.18MV-R stopped-flow (Applied Photophysics) was used for rapid kinetic studies. Kinetic simulations were through the computer program KINSIM: Chemical Kinetics Simulation System, 32-bit DOS-Extended Version 4.0, March, 1997 (Barshop, B. A., Wrenn, R. F., and Frieden, C. (1983), *Anal. Biochem.* 130:134-145). Manipulations of coordinates (overlays, distance measurements, etc.) were through Swiss-PDB Viewer 3.7 (Guex, N., and Peitsch, M. C. (1997), *Electrophoresis* 18:2714-2723). Molecular graphics images were produced using the UCSF Chimera package from the Resource of Biocomputing, Visualization, and Informatics at the University of California, San Francisco (supported by NIH P41 RR-01081) (Pettersen, E. F., Goddard, T. D., Huang, C. C., Couch, G. S., Greenblatt, D. M., Meng, E. C., and Ferrin, T. E. (2004), *J. Comput. Chem.* 25, 1605-1612) containing a package for calculating solvent-excluded molecular surfaces (Sanner, M. F., Olson, A. J., and Spehner, J. C. (1996), *Biopolymers* 38:305-320).

Preparation of Homogeneous SXA and Mutant Enzymes

Site-directed mutagenesis was performed using the QuikChange site-directed mutagenesis kit (Stratagene) according the manufacturer's instructions. Oligonucleotide primers are listed in Table 1. The template was pSRA1 with the SXA gene cloned into pET21(+) (Whitehead, T. R., and Cotta, M. A. (2001), *Curr. Microbiol.* 43:293-298). Complete sequences were determined on a 3700 sequencer (Applied Biosystems) using T7 promoter and specific primers to confirm that only the intended mutations had been introduced. Lasergene software (DNAStar) was used to analyze the sequence data. pSRA1 and its mutated plasmids were used for the transformation of *E. coli* BL21(DE3). Transformants were inoculated to 50 mL Luria-Bertani (LB) broth supplemented with 50 mg ampicillin/mL and the flask was shaken overnight at 250 rpm and 37° C. Twenty mL of the overnight culture were transferred to a 2.8-liter baffled flask containing 1.0 liter SOB medium [2.0% tryptone, 0.5% yeast extract, 0.05% NaCl, 0.0186% KCl (all in wt/vol) and 10 mM $MgSO_4$] supplemented with 50 mg ampicillin/mL. The culture was shaken at 250 rpm and 37° C. When absorbance at 600 nm reached 0.6, the culture was brought to 1 mM isopropyl-b-D-thiogalactopyranoside to induce expression of the SXA gene, and shaking was continued for 4 h. Cells were harvested by centrifugation and cell pellets were stored at −80° C. until use.

Initial purification steps and diafiltration steps were performed at 4° C. Chromatography was at room temperature (~24° C.). Cells were thawed, suspended in 40 mL of 50 mM Tris-HCl, pH 7.5 (Buffer A) containing Complete protease inhibitor cocktail (Roche) and disrupted by sonication. Following centrifugation, the supernatant was brought to 30% saturation with respect to ammonium sulfate and centrifuged. The supernatant was injected onto a column (2.6×22 cm) containing Phenyl Sepharose 6 Fast Flow resin (Amersham) equilibrated with Buffer A with 30% saturation ammonium sulfate. The column was washed until absorbance at 280 nm of the eluate became minimal (~200 mL) and developed with a 500-mL linear gradient (Buffer A+30% saturated ammonium sulfate to Buffer A). Column fractions (7 mL) were assayed for SXA activity (Methods A or B, below) for wild-type enzyme or by SDS-PAGE for catalytically-impaired mutant enzymes. SXA eluted towards the end of the gradient. Pooled fractions containing SXA were diafiltered against Buffer A and injected onto a Mono Q column (1.6×10 cm) equilibrated with Buffer A. The column was washed with Buffer A until absorbance at 280 nm of the eluate became minimal (~50 mL) and then developed with a 300-mL linear gradient (Buffer A to Buffer A+1 M NaCl). Fractions (7 mL) containing SXA were pooled, frozen in liquid $N_2$ and stored at −80° C. until use. The procedure produced homogeneous SXA and SXA mutant proteins by SDS-PAGE analysis. Overall purification of SXA on a protein basis was a factor of ~3, which is consistent with ~30% of the soluble protein in induced cells containing SXA as estimated by SDS-PAGE. Protein concentrations were estimated by using a Warburg and Christian method for impure samples and by using an extinction coefficient at 280 nm of 129600 $M^{-1}$ $cm^{-1}$ for homogeneous SXA and SXA mutants, calculated from amino acid composition (Gill, S. C., and von Hippel, P. H. (1989), *Anal. Biochem.* 182:319-326).

NMR Experiments

SXA, substrates (X2 and 4NPX), and buffer (100 mM sodium phosphate, pH 6.0) were lyophilized, dissolved in $D_2O$, and relyophilized to convert exchangeable protons to deuterium. Buffer and substrates were redissolved in $D_2O$ and added to a 5 mm NMR tube. After a reference spectrum of the substrate was completed, enzyme (10 μL enzyme in $D_2O$) was added to yield initial reaction conditions of 3 mM X2 or 4NPX, 170 nM enzyme, 70 mM sodium phosphate, pD 6.0, and 27° C. The reaction was monitored by $^1H$ NMR with a Bruker DX 500 MHz spectrometer. Time points reported represent the time when the data collection began; each time point consists of 16 scans and took approximately a minute to acquire.

Kinetics with 4NP Substrates

Two methods were employed for determining initial rates. In Method A (discontinuous monitoring), aliquots (0.02-0.2 mL) were removed from temperature-equilibrated reaction mixtures at varying time points, placed into a cuvette containing 0.80-0.98 mL 0.1 M NaOH (or 1 M $Na_2CO_3$ at pH 11 for 4NPA) so that the final volume was 1 mL, and the absorbance was read at 410 nm. Initial rates were calculated from fitting the absorbance readings versus time to a line (minimum of 4 points per reaction progression) and by using an extinction coefficient of 17.4 $mM^{-1}$ $cm^{-1}$. In Method B (continuous monitoring), temperature-equilibrated reactions (1 mL) were monitored at 380 nm (for pH values below 6) or 400 nm (for pH values of 6 and above). Reactions were generally monitored 0.3 min for initial rate determinations. Delta extinction coefficients (product-substrate) used for molar conversion were determined by subtracting the absorbance of substrate (at pH 5 so even very minor contaminating 4NP would not contribute) from the absorbance of 4NP for each reaction condition. The concentration of 4NP used for these determinations was calculated using the reported extinction coefficient of 18.3 $mM^{-1}$ $cm^{-1}$ at 400 nm for 4NP in NaOH (Kezdy, F. J., and Bender, M. L. (1962), *Biochemistry* 1:1097-1106). The concentration of 4NP substrates was determined by incubating the substrate with excess enzyme until an end point was reached, adding an aliquot (0.01 to 0.1 mL) to 0.1 M NaOH, recording the absorbance at 400 nm and using the extinction coefficient of 18.3 $cm^{-1}mM^{-1}$. Unless indicated otherwise, for both Methods A and B, reactions were initiated by adding a small aliquot of enzyme (generally 7 μl of enzyme diluted into 10 mM sodium phosphate, pH 7.0, and incubated on wet ice or at ~25° C.) to the 1-mL, temperature-equilibrated (25° C.) reaction mixtures. For pH studies, buffers of constant ionic strength (I=0.3 M), adjusted with NaCl, were used as indicated: 100 mM succinate-NaOH (pH 4.3-6), 100 mM sodium phosphate (pH 6-8), 30 mM sodium pyrophosphate (pH 8-9), glycine-NaOH (pH 9) and glycylglycine-NaOH (pH 9). The parameter, $k_{cat}$, is expressed in moles of substrate hydrolyzed per s per mole of enzyme active sites (monomers), the latter calculated from the 280 nm extinction coefficient for SXA.

Kinetics with Substrates 4NPX2, A2 and X2-X6

Products from SXA-catalyzed hydrolysis of substrates 4NPX2, A2, and X2-X6, were separated and quantified by using a DX500 HPLC system with an ED40 electrochemical detector (pulsed amperometry), AS3500 autosampler, PA-100 (4×250 mm) anion exchange column, and Chromeleon software (Dionex Corp.). Samples (25 μL) were injected onto the column equilibrated with 0.1 M NaOH and developed with a 15-min linear gradient (0.1 M NaOH to 15 mM sodium acetate) at ~25° C. and a flow rate of 1 mL $min^{-1}$. Several concentrations of the products of interest (e.g., D-xylose, 4NPX2, 4NPX, L-arabinose, and X2-X6) were used to establish standard curves on the same day experimental samples were run. Substrate concentrations were determined by HPLC analysis of samples incubated with excess SXA for complete conversion to D-xylose or L-arabinose.

For X2-X6 substrates, 1-mL reaction mixtures contained varied substrate concentrations (0.3-7 mM), 100 mM succinate-NaOH, pH 5.3 at 25° C. Before (time=0 min) and after (time=1-6 min) initiating reactions with enzyme (7 μL), samples (0.05-0.1 mL) were removed and quenched with an equal volume of 0.5 M acetic acid and frozen. Following lyophilization, samples were dissolved in $H_2O$ and analyzed by HPLC. Initial rates were calculated from linear regressions of the [D-xylose] produced versus time, rejecting later time points when they did not fit the line due to excess substrate consumption. The parameter, $k_{cat}$, is expressed in moles of substrate hydrolyzed per s per mole enzyme active sites (monomers); thus, for substrate X2, the product [D-xylose] produced was divided by two to provide the [X2] hydrolyzed, whereas for X3-X6, the [D-xylose] produced was taken as the concentration of substrate hydrolyzed. For progress curves of SXA-catalyzed hydrolysis of X4 and X6, reactions (2 mL) contained 100 mM succinate-NaOH, pH 5.3 at 25° C. Before and after addition of enzyme (7 μL), 25-μl aliquots of the reaction mixtures were directly injected onto the HPLC column for quantification of X1-X6 carbohydrates. Results from two replicate reactions were combined to provide data points for the progress curves.

In determination of initial rates for the SXA-catalyzed hydrolysis of A2, reaction mixtures (0.3 mL) contained A2 (0.2-9.0 mM), 100 mM succinate-NaOH, pH 5.3 at 25° C. Before and after addition of enzyme (7 μL), 25-μl aliquots of the reaction mixtures were directly injected onto the HPLC column for quantification of product L-arabinose. Several replicate reactions of each A2 concentration were used to generate varied time points (0-30 min) for linear regressions of product L-arabinose produced versus time. Initial rates are expressed as moles of A2 hydrolyzed per s per mole SXA active sites (monomers); thus the [L-arabinose] produced in reaction was divided by two to provide the [A2] hydrolyzed.

Reaction mixtures with varied concentrations of 4NPX2 (0.028-0.184 mM) contained 100 mM sodium phosphate, pH 7.0 at 25° C. Before (time=0) and after (time=1 and 2 min) initiating 0.5-mL reactions with 7 μl SXA, 0.1 mL aliquots were removed and quenched with 0.1 mL of 60 mM sodium pyrophosphate, pH ~12 at 4° C. so that the quenched sample was ~pH 10. Quenched samples were analyzed by HPLC for D-xylose. Initial rates were determined from linear regressions of [D-xylose] produced versus reaction time. The determined rates are expressed as moles D-xylose produced per s per mole SXA active sites. For progress curves, reaction mixtures contained 0.092 mM 4NPX2, 100 mM sodium phosphate, pH 7.0 at 25° C. Before (time=0) and after (time=1-20 min) initiating 1-mL reactions with 7 µl SXA, 0.2 mL aliquots were removed and quenched with 0.2 mL sodium pyrophosphate pH ~12 at 4° C. Quenched samples were split: one aliquot (0.15 mL) was analyzed by HPLC for D-xylose, 4NPX2, and 4NPX; the other aliquot (0.2 mL) was analyzed for 4NP by adding it to 0.8 mL of 0.1 M NaOH, recording the absorbance at 400 nm and using an extinction coefficient of 18.3 mM$^{-1}$ cm$^{-1}$ (Kezdy and Bender, ibid). Four 1-mL replicate reactions were conducted to supply data points for the progress curves. Two parallel reactions were conducted, under the same conditions with the same reaction components, the absorbance at 400 nm was continuously monitored (20 min) for 4NP production, and the absorbance values were converted to mM 4NP concentrations by using a delta extinction coefficient (product-substrate) of 8.22 mM$^{-1}$ cm$^{-1}$.

Equations

Data were fitted to equations used in this Example by using the computer program Grafit (Erithacus Software). Symbol definitions in order of occurrence: n is the observed initial rate of catalysis, $k_{cat}$ is the maximum rate of catalysis, S is the substrate concentration, $K_m$ is the Michaelis constant, I is the inhibitor concentration, $K_i$ is the inhibitor dissociation constant, p is the determined parameter at a single pH, P is the pH-independent value of the parameter, $K_a$ is the acid dissociation constant of the group affecting P, H$^+$ is the proton concentration, $K_{a1}$ is the acid dissociation constant of the first group affecting P, $K_{a2}$ is the acid dissociation constant of the second group affecting P, $P_1$ is the lower limit of p with respect to pH, $P_2$ is the upper limit of p with respect to pH, and $P_3$ is the middle limit of p with respect to pH.

$$v = \frac{k_{cat} * S}{K_m + S} \quad (1)$$

$$v = \frac{k_{cat} * S}{K_m * \left(1 + \frac{I}{K_i}\right) + S} \quad (2)$$

$$p = \frac{P}{1 + \frac{K_a}{H^+}} \quad (3)$$

$$p = \frac{P}{1 + \frac{H^+}{K_a}} \quad (4)$$

$$p = \frac{P}{1 + \frac{H^+}{K_{a1}} + \frac{K_{a2}}{H^+}} \quad (5)$$

$$p = P_1 + \frac{P_2 - P_1}{1 + \frac{H^+}{K_a}} \quad (6)$$

Results and Discussion

Models of Enzyme-Substrate Complexes

Figure 3:
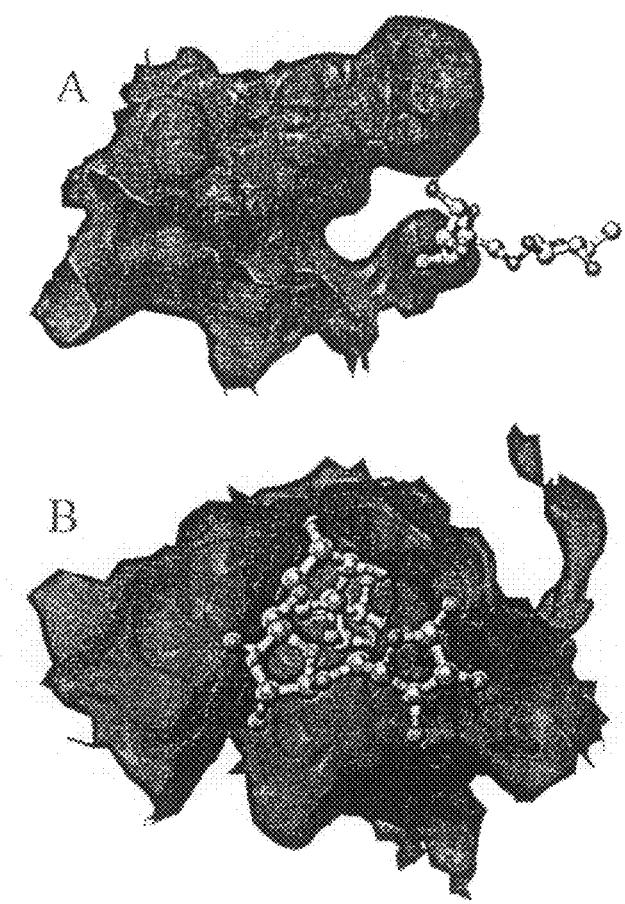
FIG. 3 shows a Molecular surface model of the SXA active site with docked 1,5-α-L-arabinohexaose. The model is based on the X-ray structures of β-xylosidase (PDB ID: 1YI7) and arabinanase with arabinohexaose bound (PDB ID: 1GYE), both enzymes of GH43. (A) View indicating that two residues of the nonreducing end of the arabinohexaose are excluded from the SXA active-site pocket. The arabinanase used for the model cleaves the arabinohexaose to yield two equivalents of arabinotriose. Because the general acid and general base of the arabinanase are aligned with those of the xylosidase, the exclusion of two residues of the nonreducing end of the arabinohexaose suggests that SXA cleaves a single residue from the nonreducing end of substrate. (B) View showing four residues of the arabinohexaose extending from the opening of the active-site pocket. Note that two arabinose residues of the reducing end of arabinohexaose protrude from the SXA active site with few protein interactions.

Recently, X-ray structures of GH43 β-xylosidases have been deposited in the Protein Data Bank (PDB ID CODES, species: 1YI7, *Clostridium acetobutylicum*; 1YIF, *Bacillus subtilis*; 1YRZ, *Bacillus halodurans*; 1Y7B, *Clostridium acetobutylicum*). The structures are of homotetrameric proteins with monomers containing two domains, one of which is similar to the five-bladed β propeller domain found in a GH43 arabinanase from *Cellvibrio Cellulosa* (Nurizzo, D., Turkenburg, J. P., Charnock, S. J., Roberts, S. M., Dodson, E. J., McKie, V. A., Taylor, E. J., Gilbert, H. J., and Davies, G. J. (2002), *Nat. Struct. Biol.* 9:665-668), which is a homodimer of monomers comprising the singe domain. Protein sequence identity of SXA against the GH43β-xylosidases with reported X-ray structures is 53-72%, and none of the X-ray structures contain glycone ligands in the active site useful for computer docking of substrates. We chose the structure of β-xylosidase from *C. acetobutylicum* (PDB ID: 1YI7) for modeling because of its highest percentage sequence identity to SXA; as well, within a 9 Å sphere of the active site of 1YI7, all 21 residues are identical in the sequence of SXA. One X-ray structure of the GH43 arabinanase (PDB ID: 1GYE) contains 1,5-α-L-arabinohexaose (A6) in the active site of a catalytically-debilitated mutant of the enzyme. A6 was computationally transferred as a rigid body from the mutant arabinanase structure to the structure of β-xylosidase from *Clostridium acetobutylicum* by aligning the backbones of the five-bladed β propeller domains (root mean square deviation of 812 pairs of atoms fitted=1.4 Å), followed by aligning two atoms of the catalytic acid and one atom of the catalytic base for a minor adjustment. The resulting model of xylosidase complexed with A6 indicates that two residues of the nonreducing end of the oligosaccharide are in steric conflict with the xylosidase protein: subsites −3, and −2 of the arabinanase are blocked by protein in the xylosidase (FIG. 3); note that subsite −1 refers to the protein site that binds the first residue on the nonreducing side of the glycosidic bond of substrate that is cleaved and more negative numbering indicates subsites that are further removed from the cleaved bond on the nonreducing side; subsite +1 refers to the protein site that binds the first residue on the reducing side of the cleaved bond and more positive numbering indicates subsites that are further removed from the cleaved bond on the reducing side (Davies, G. J., Wilson, K. S., and Henrissat, B. (1997), *Biochem. J.* 321: 557-559). Blockage of subsites −3 and −2 is conferred primarily by the presence of F509 and F510 (SXA residue numbering is used throughout the work; it differs from that of the *C. acetobutylicum* b-xylosidase by 1-6) of the xylosidase C terminus within the same subunit as the active site that is blocked. There are no corresponding residues in the arabinanase as its C terminus ends at residue 346. The arabinanase cleaves A6 to two equivalents of arabinotriose, but the model of FIG. 3 suggests that the xylosidase, having a shallower active-site cavity, cleaves a single monosaccharide from the nonreducing end.

Figure 4A:
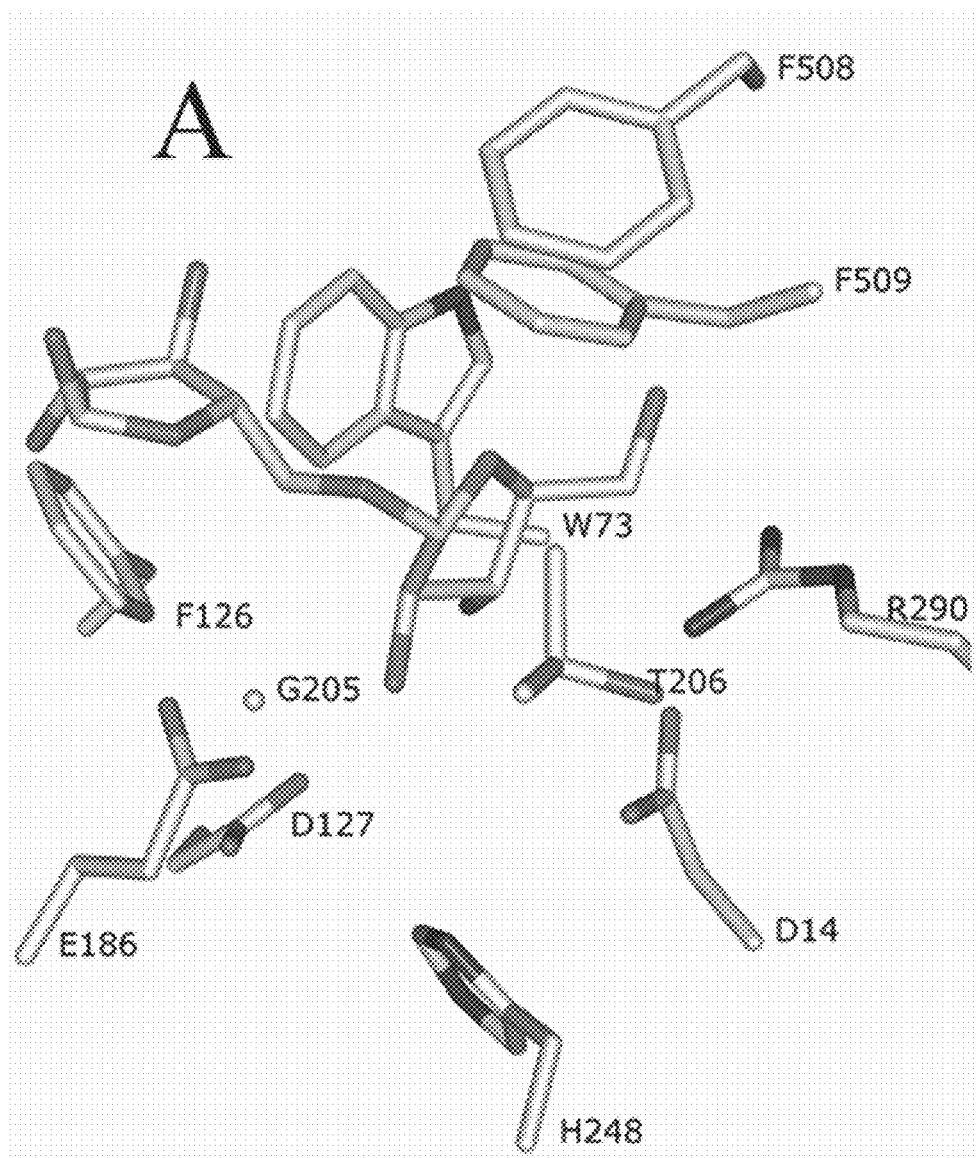
FIG. 4 shows models of disaccharide substrates docked in the active site of SXA. Views are of a sphere emanating 6 Å from the oxygen atom bridging the two monosaccharide residues. Key residues, D14, D127 and H248, which are ~1 Å outside the 6 Å radius, are added to the view. (A) 1,5-α-L-Arabinobiose (A2). (B) 1,4-β-D-Xylobiose (X2). (C) α-Arabinofurano-D-xylose (AX).

1,5-α-L-Arabinobiose (A2) is accepted as a substrate by SXA (Natural Substrates section). A model of A2 in the xylosidase active site was built by clipping two arabinose residues from the nonreducing end and two residues from the reducing end of A6 in the model of FIG. 3 (FIGS. 4A and 5). In the model, the carboxylate oxygen of D14 is ~6 Å from the anomeric carbon of the scissile bond and the carboxylate oxygen of E186 is ~4 Å from the glycosidic oxygen atom of substrate. The distances are similar to those found in other glycoside hydrolases that act by inverting the configuration of the anomeric carbon of substrate: thus, in FIG. 4 there is space to accommodate a water molecule between the carboxyl group of D14 and the anomeric carbon of substrate for addition and the carboxyl group of E186 is in position to protonate the oxygen atom bridging arabinose residues. The carboxyl group of D14 shares a salt bridge with the guanidinium group R290 and an H bond with the imidazole group of H248. The carboxyl group of E186 shares an H bond with the carboxyl group of D127. Together, E186, D127, H248, D14 and R290 form an H bonding network within subsite −1.

Figure 4B:
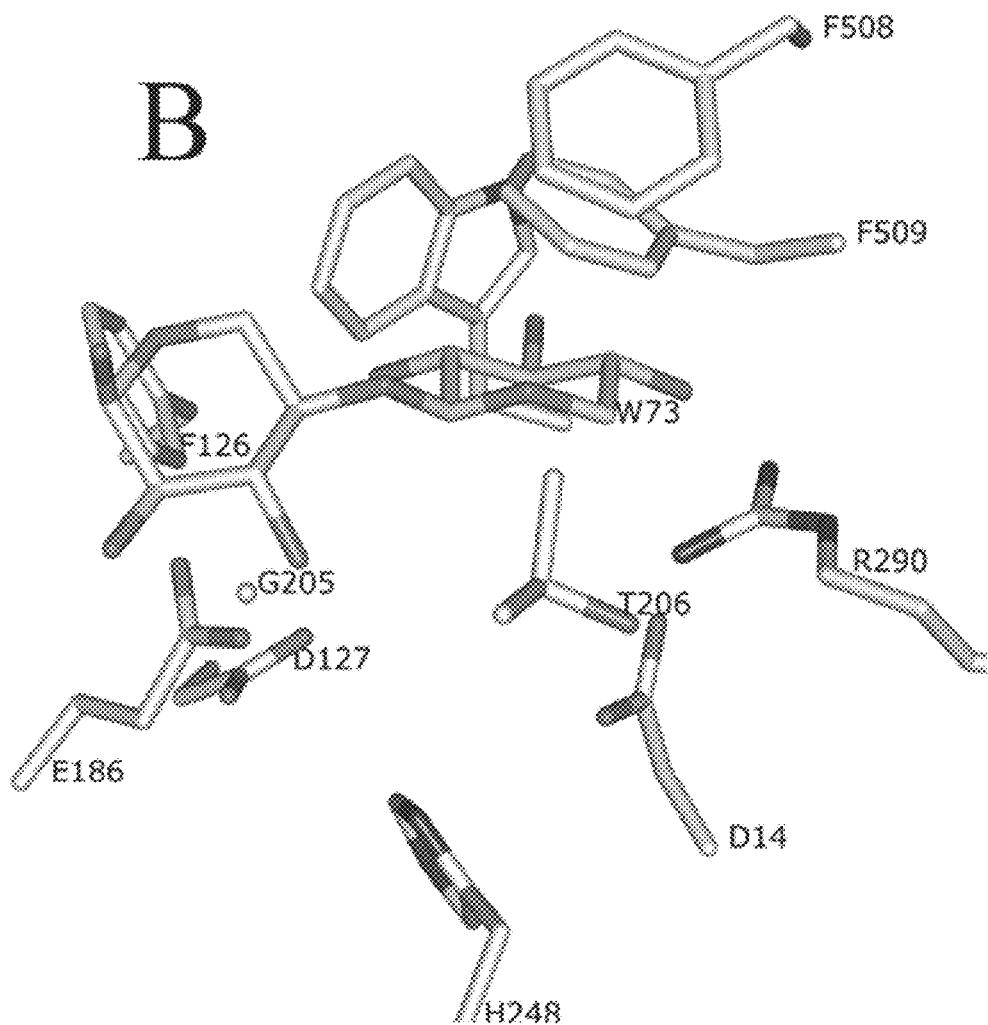
Figure 5:
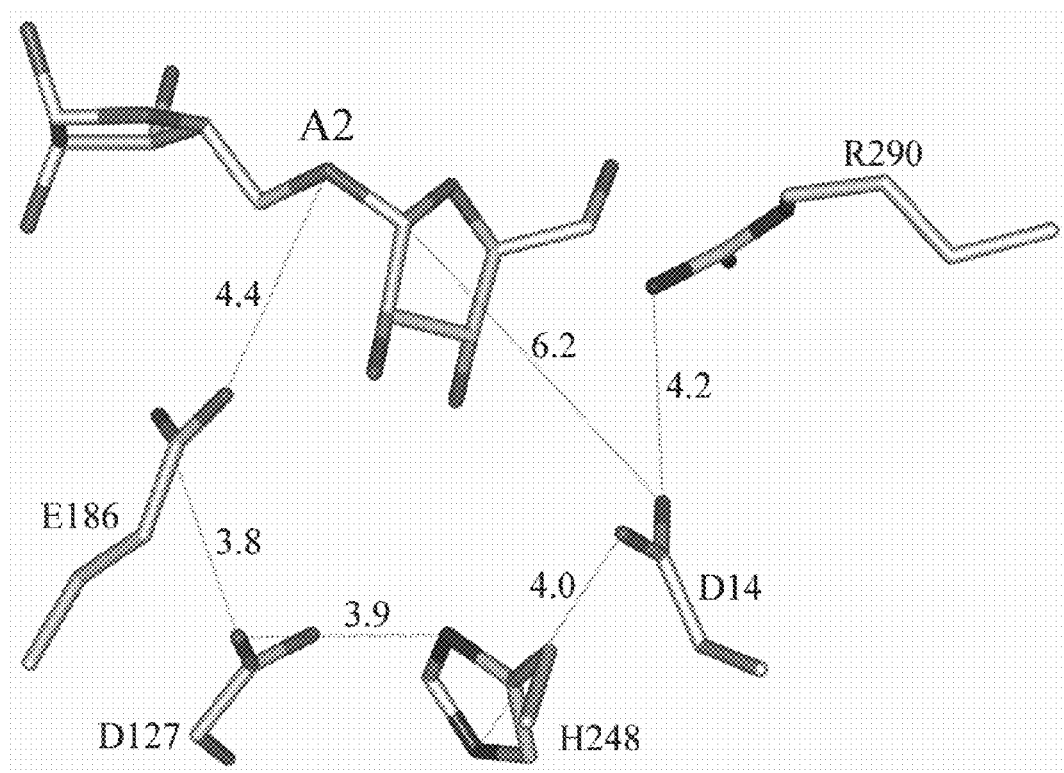
FIG. 5 shows a model of 1,5-α-L-arabinobiose (A2) docked in the active site of SXA. Key residues and distances (in Å) are shown.

Xylobiose (X2) was built into the model of xylosidase using the A2 ligand as a guide, overlaying atoms of the glycosidic bond that is cleaved and the C3 of the reducing xylose onto the C2 of the reducing arabinose residue of A2 to generate the model (FIG. 4B). Similar to the model with A2 in the active site, X2 is well positioned to serve as substrate (with similar distances reported for the SXA-A2 model). X2 is an excellent substrate for SXA (Natural Substrates section).

Figure 4C:
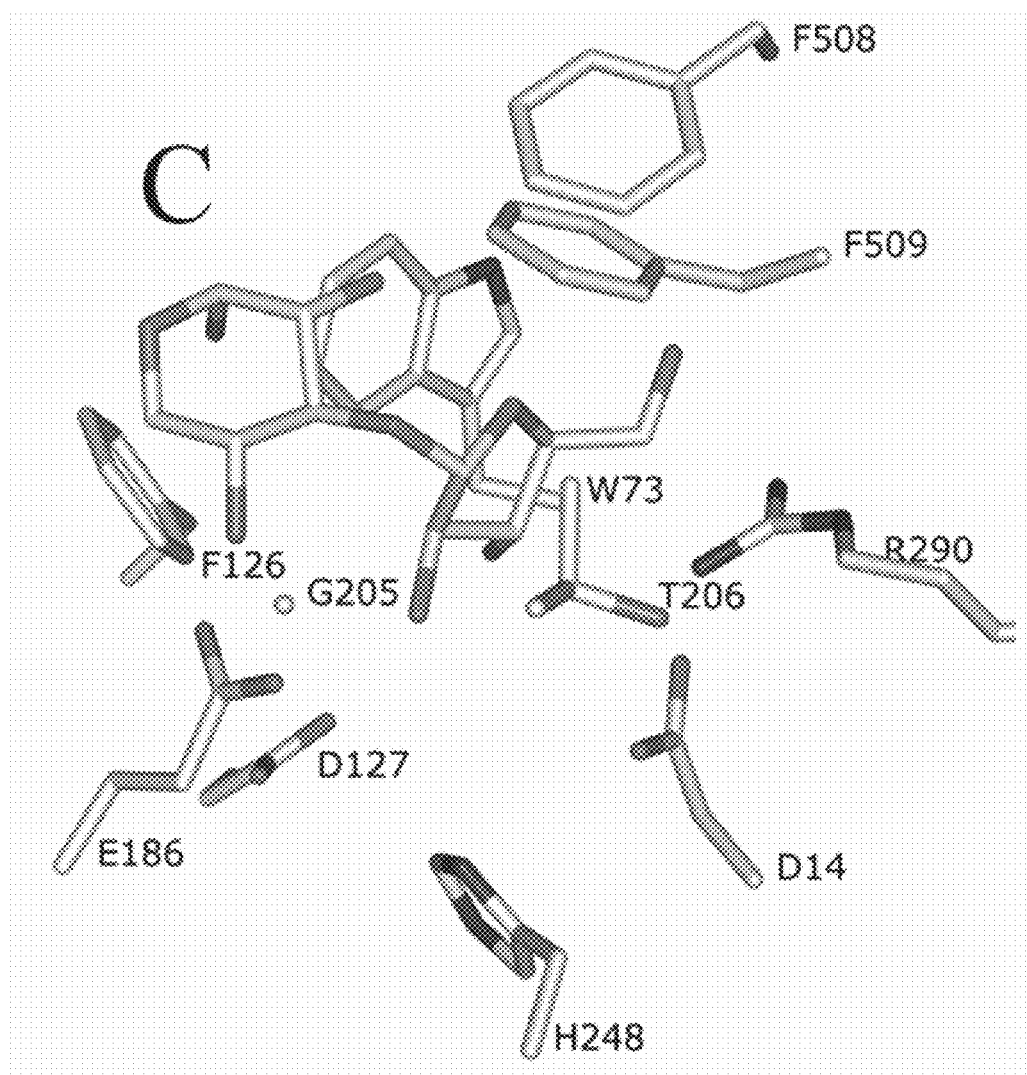

D-Xylose, substituted at the 2' or 3' OH group with L-arabinofuranose, is a constituent of xylan from certain plant species and a potential substrate for SXA and other β-xylosidases. 1,3-α-Arabinofurano-D-xylose (AX) was built into the active-site model of SXA by replacing the arabinose residue of the reducing end of A2 (in the model of FIG. 4A) with D-xylose (FIG. 4C). The model suggests that AX is in a good position to serve as substrate. As well, it suggests that the arabinose substitutions of xylooligosaccharides must be to the nonreducing end of the chain for SXA to catalyze its cleavage; i.e., the arabinofuranose residue must occupy subsite −1 of SXA. Moreover, if there is more than one arabinose substitution to a xylooligosaccharide, it could not be accommodated by subsite +1 and would have to be two or three residues more towards the reducing end of the xylooligosaccharide, which extend to bulk solvent. AX, specifically, has not been studied as a substrate for SXA, but SXA has been shown to liberate arabinose residues from arabinoxylan, digested to oligosaccharides by xylanase (Cotta, M. A., and Whitehead, T. R. (1998), *Curr. Microbiol.* 36: 183-189).

¹H NMR Determination of Reaction Stereochemistry

Figure 6:
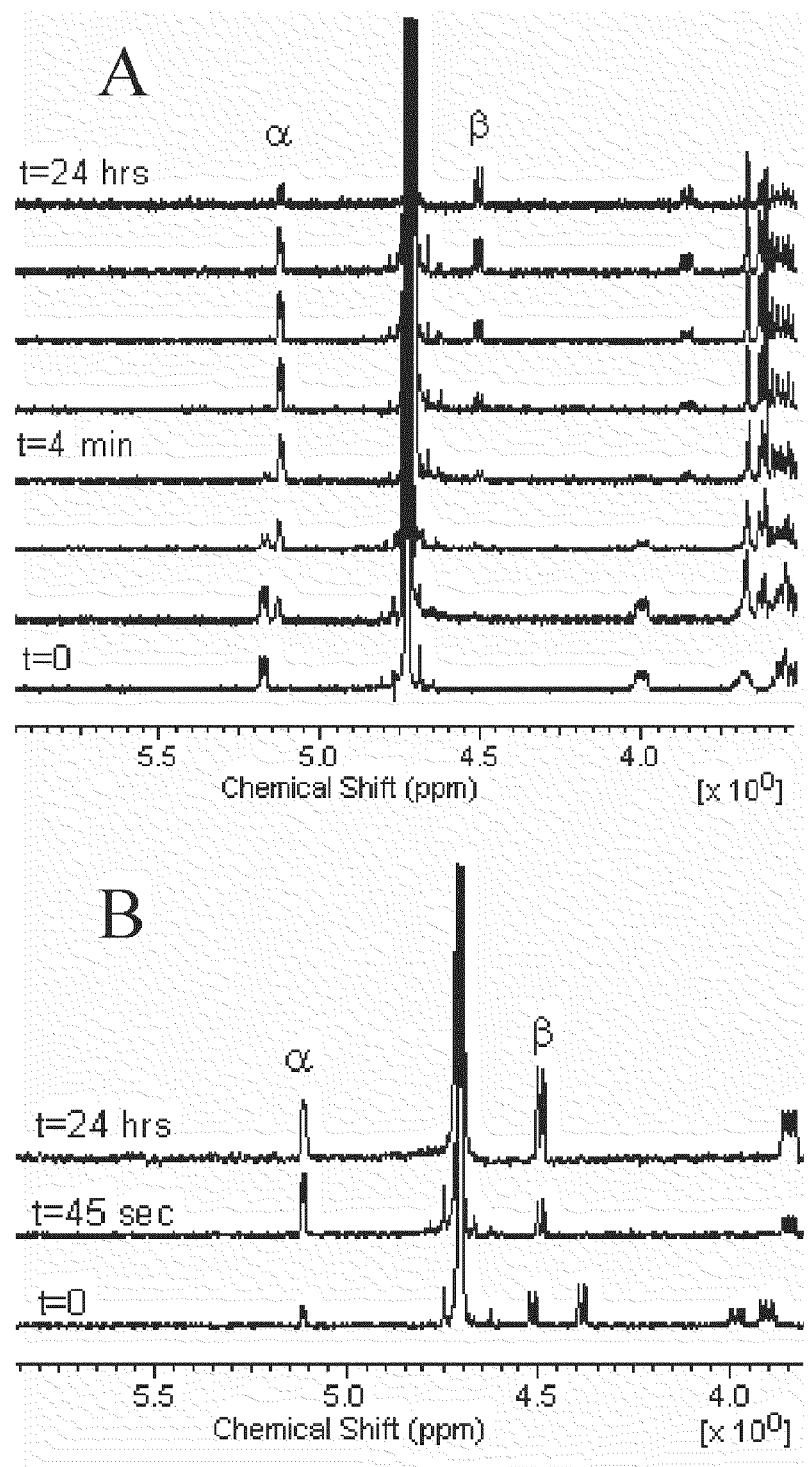
FIG. 6 shows $^1H$ NMR monitoring of SXA-catalyzed hydrolysis of 4-nitrophenol-β-D xylose (4NPX) and 1,4-β-xylobiose (X2). (A) 4NPX. The bottom spectrum is a reference spectrum of 4NPX before enzyme addition (time=0). After the addition of enzyme the spectra, in ascending order, are time=45 s, 2.5 min, 4 min, 5.5 min, 7 min, 11 min, and 24 h. (B) X2. The bottom spectrum is a reference spectrum of X2 before enzyme addition (time=0). After the addition of enzyme the spectra, in ascending order, are time=45 s and 24 h.

GH43 is annotated to catalyze hydrolysis of substrates to products through inversion of stereochemistry of the anomeric carbon. The inversion mechanism has been determined experimentally for a GH43 β-xylosidase from *Bacillus pumilus* acting on substrate 4NPX and using an enzyme coupling reaction that specifically reports for α-xylose (Kersters-Hilderson, H., Claeyssens, M., Van Doorslaer, E., and De Bruyne, C. K. (1976), *Carbohydr. Res.* 47:269-273) and for a GH43 β-xylosidase from *Butyrivibrio fibrisolvens* acting on 2-nitrophenyl-β-D-xylopyranoside by using an HPLC separation method (Braun, C., Meinke, A., Ziser, L., and Withers, S. G. (1993), *Anal. Biochem.* 212:259-62). Stereochemistry of GH43 xylosidases acting on xylooligosaccharides has not been reported. We used ¹H NMR to determine the stereochemistry of 4NPX and X2 hydrolysis reactions catalyzed by SXA (FIG. 6). For 4NPX, the enzymatic reaction was complete in approximately 5 min. At 4 min, the anomeric isomer ratio (α:β) in the D-xylose product was 20:1. That 100% of the D-xylose product was not found in the α configuration is likely due to mutarotation from α to β, which has a half life of <1 h under the incubation conditions. After incubation 24 h, the anomeric isomer ratio at equilibrium was determined as 1:2.5. For substrate X2, the enzymatic reaction was faster and the reaction had reached completion at the first time point (45 s) after enzyme addition. At 45 s, the anomeric isomer ratio (α:β) of the xylose product was 6:1. The 6:1 ratio suggests that the anomeric carbon of X2, not sharing the scissile bond, has an isomeric ratio (α:β) of 2.5:1. After incubation 24 h, the anomeric isomer ratio at equilibrium was determined as 1:2.5. Thus, SXA catalyzes the hydrolysis of 4NPX and X2 by inversion of configuration of the anomeric carbon sharing the scissile bond. This invokes a single step mechanism (single transition state) for the hydrolysis reactions catalyzed by SXA.

4NP-Glycoside Substrates

For experimental convenience and latitude, it is desirable to have the availability of several 4NP-glycosides as substrates for the study of SXA. A survey of commercially available 4NP-gylcosides found that only two (4NPX and 4NPA) serve as substrates for the enzyme (Table 2). Upon first inspection, 4-nitrophenyl-β-L-arabinopyranoside appeared to serve as a substrate, having a rate less than 0.1% that of 4NPX under the reaction conditions shown in Table 2. Further examination of the potential substrate, monitoring its progression to 4NP in a reaction catalyzed by SXA, indicated that only 0.08% of the 4NP-glycoside can be hydrolyzed by SXA. After incubating SXA for 1 h in the absence or presence of the preparation of 4-nitrophenyl-β-L-arabinopyranoside, aliquots were removed and assayed with substrate 4NPX; enzyme incubated in the absence or presence of the preparation had the same catalytic activity, indicating that SXA was not inactivated by the preparation. Therefore, 99.9% of the 4-nitrophenyl-β-L-arabinopyranoside preparation does not serve as a substrate for SXA, and it is likely that the commercial preparation was contaminated with a 4NP-glycoside that serves as a substrate (possibly 4NPA).

Steady-state kinetic parameters of SXA-catalyzed hydrolysis of 4NPX or 4NPA were modestly influenced by increased viscosity (Table 3). When 50% sucrose was included in the reaction mixtures, $k_{cat}$ and $k_{cat}/K_m$ for substrates 4NPX and 4NPA were eroded by less than 12%, indicating that diffusion is a minor kinetic factor limiting SXA-catalyzed hydrolysis of these substrates. Had the reactions been fully controlled by diffusion, the kinetic parameters would be degraded by more than 80%.

Stopped-flow experiments, recording reactions (at 400 nm) of 4 mM 4NPX or 4NPA with 10 μM SXA in 100 mM sodium phosphate, pH 7.0, I=0.3 M and 25° C., gave no indication of bursts (or lags) in the production of 4NP, ruling out the possibility of slow release of products limiting the steady-state rates for these substrates. Moreover, zero-order rates, determined by using the stopped-flow in 100 ms reactions, were similar (within 5%) to the zero-order rates determined by using the conventional spectrophotometer in 30 min reactions under the same buffer, temperature and substrate conditions but much lower concentration of SXA.

A recent study of the GH43 β-xylosidase from *Geobacillus stearothermophilus* reported that the progress curve of the enzyme-catalyzed hydrolysis of 4-nitrophenyl-β-D-xylobioside (4NPX2) shows a lag in 4NP production (Shallom, D., Leon, M., Bravman, T., Ben-David, A., Zaide, G., Belakhov, V., Shoham, G., Schomburg, D., Baasov, T., and Shoham, Y. (2005), *Biochemistry* 44:387-397), suggesting that the enzyme catalyzes hydrolysis of the D-xylose residue occupying the nonreducing end of 4NPX2 (to yield D-xylose and 4NPX) instead of catalyzing hydrolysis of the 4NP residue from the opposite end of 4NPX2. However, production of D-xylose and 4NPX and consumption of 4NPX2 were not monitored quantitatively, leaving the possibility that all products and substrates display lags. We monitored progress of SXA-catalyzed hydrolysis of 4NPX2 using HPLC and spectrophotometric methods for determining the concentrations of 4NPX2, 4NPX, D-xylose, X2 and 4NP (FIG. 7). The progress curves indicate that there is a lag in the production of 4NP, but not in the production of D-xylose or 4NPX and not in the consumption of 4NPX2, ruling out the possibility that the lag in 4NP production owes to hystereses of SXA action on 4NPX2. There was no accumulation of X2. It strongly suggests that SXA catalyzes the hydrolysis of 4NPX2 in two steps without processivity: in the first, D-xylose is cleaved from the nonreducing end of 4NPX2 and products D-xylose and 4NPX leave the enzyme; and, in the second, D-xylose is cleaved from the nonreducing end of 4NPX. Kinetic parameters for first step of SXA-catalyzed hydrolysis of 4NPX2 (4NPX2 to 4NPX+D-xylose) were determined (in the same reaction buffer) by HPLC analyses of product D-xylose: $k_{cat}$=50.5±25.7 s$^{-1}$, $k_{cat}/K_m$=73.3±8.4 s$^{-1}$mM$^{-1}$, and $K_m$=0.69±0.43 mM. Kinetic parameters for the second step (4NPX to 4NP+D-xylose) were determined (in the same reaction buffer) spectrophotometrically (Method B): $k_{cat}$=16.2±0.09 s$^{-1}$, $k_{cat}/K_m$=36.6±0.5 s$^{-1}$mM$^{-1}$, and $K_m$=0.443±0.008 mM. The kinetic parameters and concentrations of SXA (24.8 nM) and 4NPX2 (0.092 mM) were used as inputs for KINSIM calculations to a model that assumes rapid equilibrium binding, a single residue from the nonreducing end of substrate is cleaved per catalytic cycle and lack of processivity so that hydrolysis products are removed from SXA at the end of each catalytic cycle prior to initiating a new one. The simulation closely fits the observed concentrations of 4NPX2, D-xylose, 4NPX and 4NP in the progress curves of FIG. 7, thus reinforcing the conclusion that SXA catalyzes the hydrolysis of 4NPX2 in two steps by removing a D-xylose residue from the nonreducing end of substrate in each step without processivity. It should be noted that, whereas $k_{cat}$ (4NPX2) and $K_m$ (4NPX2) are not well determined because the highest substrate concentration was well below the $K_m$ in the determination, $k_{cat}/K_m$(4NPX2) is fairly well determined and the latter parameter was most important in the KINSIM calculations of the reaction progress that was conducted under $k_{cat}/K_m$ conditions.

Site-Directed Mutations and Catalysis

According to the models of FIG. 4, D14 is positioned to serve as a general base activating a water molecule for addition to the anomeric carbon of substrate and E186 is positioned to protonate the leaving group oxygen atom. Residues D128, H248 and R290 form an H bonding network with D14 and E186, likely for the purpose of positioning the side chains of D14 and E186 for reacting with substrate and to manipulate their p$K_a$ values for reactivity. Individual mutation of the residues to alanine degrades $k_{cat}$(4NPX) by factors of 3300, 12000, 24000, 330, and 2500 for D14A, E186A, D127A, H248A, and R290A, respectively, confirming the individual importance of the native residues to catalysis (Table 4). $K_m$(4NPX) values were similar to wild-type with the exception of R290A, whose $K_m$(4NPX) is increased by 70-fold. Thus, four of the residues appear to exclusively serve in roles of general acid or general base (D14 and E186) or indirectly in supporting the general acid or general base (D127 and H248). R290, in addition to its role in assisting D14 in its role as a general base in the hydrolysis reaction, appears to serve as a recognition element for the substrate. The guanidinium group of R290 resides near the nonreducing end of substrate in the models of FIG. 4.

SXA mutations, D14A and E186A, degraded catalysis with substrate 4NPA to a similar extent as with substrate 4NPX (Table 5). As with substrate 4NPX, $K_m$(4NPA) values were similar to native SXA, while the $k_{cat}$ parameter was degraded by factors of 3000 and 11000 for mutations D14A and E186A, respectively. Despite such drastic erosion of catalytic power in the mutants, native SXA and the mutants share similar values for relative substrate specificity for 4NPX and 4NPA: $k_{cat}/K_m$(4NPX)/$k_{cat}/K_m$(4NPA) values calculated from the values in Tables 4 and 5 are 12.3±0.9, 10.2±0.7, and 13.4±1.3 for native SXA, D14A, and E186A, respectively. The relative substrate specificity values substantiate that substrates 4NPX and 4NPA share the same active site.

Natural Substrates of SXA

By using HPLC analysis for quantification of reaction products, steady-state kinetic parameters of SXA-catalyzed hydrolysis of substrates X2-X6 and A2 were determined (Table 6). X2 is the best substrate having a $k_{cat}/K_m$ value of 99 s$^{-1}$mM$^{-1}$, whereas $k_{cat}/K_m$ values of ~40 s$^{-1}$mM$^{-1}$ were determined for substrates X3-X6. A $k_{cat}$ of 412 s$^{-1}$ was determined for X2, which is 2-4 fold that of substrates X3-X6. Clearly, chain lengths beyond two xylose residues do not increase substrate specificity, and this corresponds with the lack of well-defined subsites beyond +1 in SXA active-site models for recognition of additional xylose residues on the reducing side of substrate. The observed decrease in $k_{cat}/K_m$ and $k_{cat}$ for X3-X6 may owe to somewhat lower flexibility of the residue occupying the +1 position that could impede deformation of substrate by enzyme in approaching the structure in the transition state. In comparison with substrate 4NPX under the same reaction conditions (Table 4), $k_{cat}$ and $k_{cat}/K_m$ for X2 are respectively 12-fold and 2-fold larger, even though 4NPX has a much better leaving group in 4NP and the noncatalyzed rate of hydrolysis of 4NPX exceeds 10$^7$-fold that of X2. Hence, subsite +1 can exert considerable influence on the rate of catalysis, and thus substrate specificity. Besides SXA, there are only a few β-xylosidases for comparing kinetic parameters for xylooligosaccharides (Van Doorslaer, E., Kersters-Hilderson, H., and De Bruyne, C. K. (1985), *Carbohydr. Res.* 140:342-346; Wagschal, K, Franqui-Espiet, D., Lee, C. C., Robertson, G. H., and Wong, D. W. (2005), *Appl. Environ. Microbiol.* 71:5318-5323; Kimura, I., and Tajima, S. (1999), *J. Biosci. Bioeng.* 87:572-575). The best catalyst among these, the enzyme from *Bacillus pumilus*, has reported $k_{cat}$ and $k_{cat}/K_m$ values for X2 of 18 s$^{-1}$ and 6.2 s$^{-1}$mM$^{-1}$ at pH 7 (the pH optimum for the catalyzed hydrolysis of 4NPX by the enzyme) and 25° C. (Van Doorslaer, ibid), values that are less than 7% those of SXA. Similarly, the reported $k_{cat}$ and $k_{cat}/K_m$ values for the *Bacillus pumilus* enzyme acting on substrates X3-X6 are less than 6% those of SXA. Assuming the noncatalyzed rate of hydrolysis for X2 is similar to that of a-methylglucopyranoside (Wolfenden, R., Lu, X., and Young, G. (1998), *J. Am. Chem. Soc.* 120:6814-6815), SXA enhances the rate of X2 hydrolysis by a factor exceeding 1017 and the dissociation constant for the transition state (ES') is ~10$^{-19}$. A2 was the worst naturally-occurring substrate examined, having $k_{cat}$ and $k_{cat}/K_m$ values reduced by factors of 36 and 53, respectively, in comparison to 4NPA, and by factors of 5600 and 1600, respectively, in comparison to X2. Clearly, SXA does not accommodate well the arabinofuranose residue in subsite +1 with an α-1,5 linkage to the arabinofuranose residue in subsite −1, and it is likely that A2 does not serve as a natural substrate for SXA. In contrast, AX, with an arabinofuranose residue occupying subsite −1 and a xylose residue, subsite +1, is considered a likely natural substrate for SXA, though kinetic parameters are not yet available for AX to judge how well it is accepted by SXA.

Progress curves for SXA-catalyzed hydrolysis of X6 and X4 were monitored by using HPLC analysis for quantification of substrates and products and compared with progress curves predicted by KINSIM calculations with inputs of the kinetic parameters of Table 6 and $K_i$(xylose)=7.4 mM (determined using substrate 4NPX in the same buffer at pH 5.3 at 25° C.) and assuming that a single xylose residue is removed from the nonreducing end of substrate per catalytic cycle without processivity (FIG. 8). The KINSIM calculations of temporal concentrations of hydrolysis products of substrates X6 and X4 approximate the observed concentrations in the SXA-catalyzed reactions. In the hydrolysis of X6, peak heights of intermediate products (observed: KINSIM predicted) occur in the reaction coordinate as follows (values in s): X5 (3138:3140), X4 (8260:7070), X3 (10822:10750), and X2 (13384:13700). Thus, experimental data indicate temporal peaks of intermediates occur in descending order of appearance X5>X4>X3>X2, which was assumed in the simulation. Similarly, in the hydrolysis of X4, the occurrence of peak heights of intermediate products (observed: KINSIM predicted) are as follows: X3 (4130:5100) and X2 (2940:3300), indicating that X3 precedes X2 as a product in the reaction coordinate. Thus, SXA-catalyzed hydrolysis of naturally-occurring substrates, X6 and X4, proceeds with a single residue cleaved per catalytic cycle in the absence of processivity.

Influence of pH on Catalysis

Steady-state kinetic parameters were determined at varying pH and constant ionic strength for substrates 4NPX and 4NPA (FIGS. 9 and 10). SXA is unstable at pH values below 4.1, limiting the study to higher pH's. Curves for the two substrates are similar in shape for $k_{cat}/K_m$ with $pK_{a1}$ and $pK_{a2}$ values of 5.0 and 7.2 for the acidic and basic limbs, respectively: $pK_{a1}$=5.0 for the catalytic base (D14) and $pK_{a2}$=7.2 for the catalytic acid (E186). Thus, for substrates 4NPX and 4NPA, the pH-independent $k_{cat}/K_m$ reflects the "monoanionic" form of SXA (D14$^-$E186$^H$), and $k_{cat}/K_m$ is fully degraded when the enzyme becomes protonated to the "diprotic" SXA (D14$^H$ E186$^H$) or deprotonated to the "dianionic" SXA (D14$^H$ E186$^H$). The $pK_a$ values for active-site carboxylic acid residues (D14, D127, and E186) are likely raised by their proximity to one another (within 6 Å); $pK_{a1}$=5.0, reporting for the carboxylic group of D14, is likely made more normal by its close proximity (4.2 Å) to the guanidinium group of R290 and $pK_{a2}$=7.2, reporting for the carboxylic group of E186, is likely made more basic by its close proximity (3.8 Å) to the carboxylic group of D127. Curves for the two substrates differ in shape for $k_{cat}$: substrate 4NPA is mainly flat over the pH range examined and $k_{cat}$ drops on the acid side with a single $pK_a$ value of 3.6; $k_{cat}$ for substrate 4NPX shows a $pK_{a1}$ of 3.5 for a drop on the acid side and a $pK_{a2}$ of 6.9 for a drop on the basic side. The $pK_a$ values of ~3.5 are not well determined because the lowest pH in the studies was 4.3; yet, for substrate 4NPX, omitting the $K_{a1}$ parameter of Eq. 5 (to give Eq. 3) is not preferred statistically over its inclusion (F test probability of 8%), and for substrate 4NPA, omitting the $K_a$ term of Eq. 4 (to give a line of slope=0) is not preferred over its inclusion (F test probability of 1%). Extension by 1.5 pH units of the $pK_a$ for $k_{cat}$ over that of $k_{cat}/K_a$ would not be unusual (Cleland, W. W. (1982), Methods Enzymol. 87:390-405). It is plausible that the $pK_a$ of D14 is shifted in the ES complex in comparison to the free enzyme ($pK_a$=5.0) because in our models of SXA complexed with A2, X2, and AX (FIG. 4) there is space for only one water molecule in subsite −1. The water (water of hydrolysis) is located between substrate C1 and the carboxyl group of D14. Thus, in this model, the "diprotic" SXA (D14$^H$ E186$^H$) does not bind nor catalyze the hydrolysis of 4NPX nor 4NPA. On the basic side, differences between the two $k_{cat}$ profiles are likely conferred by formation of a nonproductive complex between substrate 4NPX and the "dianionic" form of SXA (D14$^-$ E186$^-$), in which both the general base and general acid are deprotonated and unable to catalyze the hydrolysis reaction, whereas substrate 4NPA does not bind to the "dianionic" form. The binding constant of 4NPX to the "dianionic" SXA is moderately more potent than the binding constant to the "monoanionic" SXA (D14$^-$ E186$^H$), the latter in which the base and acid are in the correct protonation state for catalysis. Thus, increased pH inhibits the SXA-catalyzed hydrolysis of 4NPX noncompetitively (inhibition cannot be overcome by increased 4NPX concentrations) and the $1/K_m$(4NPX) value remains high, but the SXA-catalyzed hydrolysis of 4NPA is inhibited competitively by increased pH so that $k_{cat}$ remains at the pH-independent value as $1/K_m$(4NPA) becomes smaller.

Figure 9C:
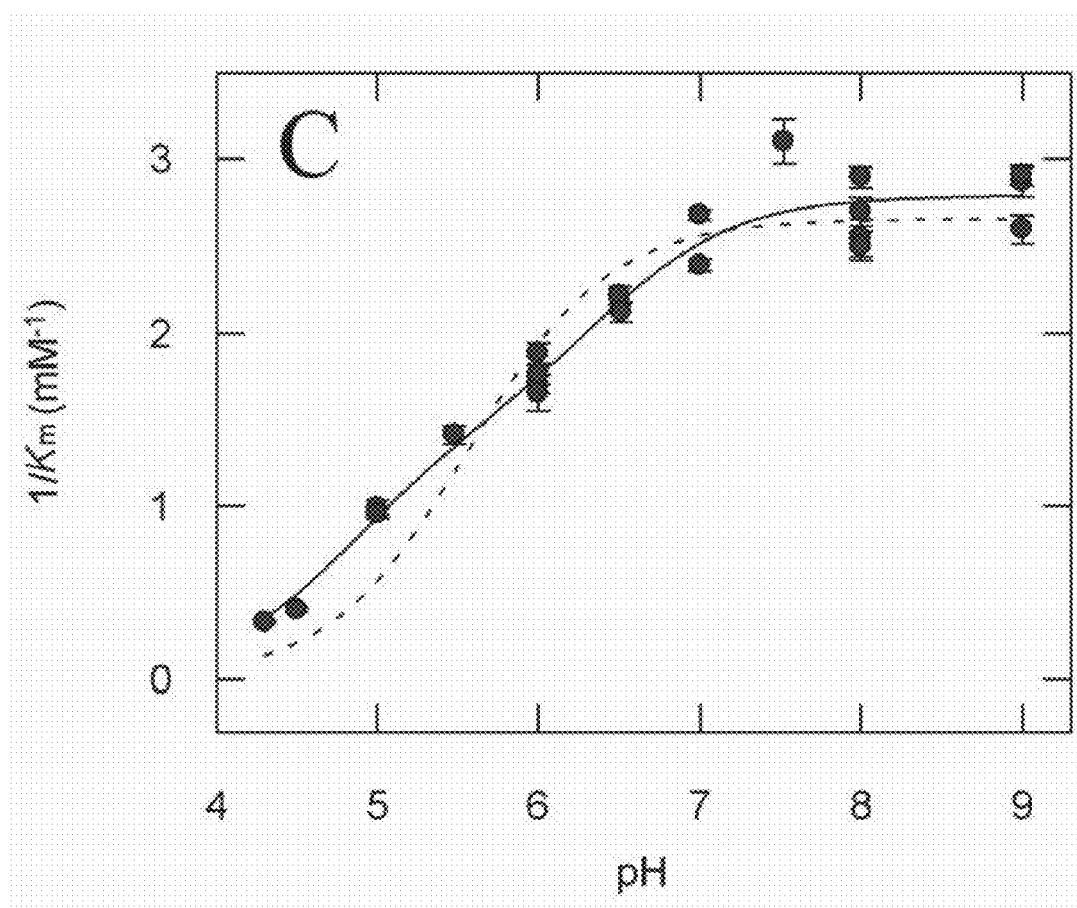

The pH dependency of $1/K_m$(4NPX) fits a diprotic model (Eq. 7) with two protonatable groups on the acidic limb (FIG. 9C): $pK_{a1}$=4.8 and $pK_{a2}$=6.4. In the diprotic model, and 4NPX binds with ~2-fold greater affinity to the "dianionic" SXA (D14$^-$ E186$^-$) than to the "monoanionic" SXA (D14$^-$ E186$^H$), and it does not bind to the "diprotic" form of enzyme (D14$^H$ E186$^H$). The parameter, $1/K_m$(4NPX), can be fitted to a monoprotic model (Eq. 4), but the fitted curve has a higher reduced $\chi^2$ value than that for the diprotic model (Eq. 7) and F test indicates that there is 0.033% probability the data fit Eq. 4 as well as Eq. 7 (FIG. 9C). Also, fitting the data to Eq. 4 provides p $K_a$ value of 5.6 for $1/K_m$(4NPX), which approximates an average of the values for $pK_{a1}$ and $pK_{a2}$, determined in the diprotic model, and $pK_a$ of 5.6 has no known structure-function relevance.

It is not unusual, in the literature, for the relative activities of bifunctional enzymes to be reported as a ratio of the two individual activities, measured separately at a single pH and single substrate concentration. In the case of SXA, which has disparate pH profiles for $k_{cat}$ with substrates 4NPX and 4NPA, relative rates (4NPX/4NPA) at a single pH and nearly saturating substrate concentrations would range from 10 to 0.6 between pH 4.3 and 8 and would approach 0 at higher pH's. The different pH profiles for $1/K_m$ and $k_{cat}$ for substrates 4NPX and 4NPA could lead to an incorrect inference that SXA has separate active sites for the two substrates; this, of course, can be ruled out from our data that indicates mutations of SXA active-site residues (D14A and E186A), which impart severe erosion of catalysis, have similar values as wild-type SXA for relative substrate specificities of 4NPX and 4NPA:

$k_{cat}/K_m$(4NPX)/$k_{cat}/K_m$(4NPA)=12 at pH 5.3 and 25° C.

Conclusions

SXA is the best catalyst known for promoting hydrolysis of β-D-1,4-xylooligosaccharides, by factors greater than 15 when comparing $k_{cat}$ and $k_{cat}/K_m$ values for substrates X2-X6 to values obtained for the enzymes from other species. This property, its ability to catalyze hydrolysis of L-arabinoxylose (Whitehead and Cotta, 2001, ibid), its favorable pH optima (nearly constant $k_{cat}$ between pH 4.5 and 6), and its apparent lack of transglycosylation activity place SXA in the forefront among β-xylosidases for application in the saccharification of xylan-containing materials. Limitations to its effectiveness, if any, in fermentation applications can be addressed upon their identification. SXA was isolated from an organism, S. ruminantium, whose native environment (cow rumen) is rich in materials containing xylan and (with assistance from xylanases) xylooligosaccharides. Thus, SXA serves in a highthroughput environment that may select for high performing catalysts in providing nutrients to support the large animal. It is encouraging that diversity of hydrolases in the cow rumen continues to be explored (Ferrer, M., Golyshina, O. V., Chemikova, T. N., Khachane, A. N., Reyes-Duarte, D., Martins Dos Santos, V. A. P., Strompl, C., Elborough, K., Jarvis, G., Neef, A., Yakimov, M. M., Timmis, K. N., and Golyshin, P. N. (2005), *Environ. Microbiol.* 7:1996-2010).

Certain mechanistic fundamentals are established for SXA: it catalyzes hydrolysis of the glycosidic bond shared by the terminal residue of the nonreducing end of substrate, SXA catalyzes hydrolysis through a single displacement mechanism that inverts the configuration of the anomeric carbon that shares the glycosidic bond of hydrolysis, the catalytic base and catalytic acid of SXA have p $K_a$ values of ~5 and 7, respectively, hydrolysis of 4NPX and 4NPA are catalyzed by the same active site with the sugar moiety occupying subsite −1, and subsites −1 and +1 are the only subsites that affect binding and catalysis. Subsites −1 and +1 can exert considerable and selective catalytic power as seen in the progression of relative $k_{cat}$ values (at pH 5.3 and 25° C.) of 5600, 340, 34, and 1 for substrates X2, 4NPX, 4NPA, and A2, respectively.

Biochemical conclusions are fully consistent with the three-dimensional models of the active site in terms of residues and distances: the active-site models allow assignments of D14 and E186 as the catalytic base and catalytic acid, respectively; the lack of subsites beyond −1 on the nonreducing side owe to the active site being capped with amino acid residues that prevent formation of additional subsites; the lack of subsites beyond +1 on the reducing side owes to the wide, solvent-exposed opening to the active site preventing additional subsites to be defined; and the $pK_a$ values for the carboxyl groups of D14 and E186 are differentially modulated through H bonds and a salt bridge. In addition, the models place restrictions on the binding mode of putative substrate AX (arabinose moiety must occupy subsite −1) and arabinoxylose analogs that may serve as substrates.

The influence of pH on catalysis apparently reflects the protonation state of the catalytic base (D14, p $K_a$=5.0 for $k_{cat}/K_m$) and catalytic acid (E186, p $K_a$=7.2 for $k_{cat}/K_m$). The catalytically active form of SXA is the "monoanionic" form (D14$^-$ E186$^H$). One of the two catalytically inactive forms of SXA is the "diprotonated" form (D14$^H$ E186$^H$). D14$^H$ E186$^H$ binds substrates 4NPX and 4NPA weakly, if at all, because otherwise the pH profiles for $k_{cat}$ would reflect a p $K_a$ of 5, which they do not. Thus, D14$^H$ E186$^H$ has no apparent functional properties. It is plausible that the protonation state of D14$^H$ E186$^H$ disrupts H bonds and the salt bridge that are formed in the active site of D14$^-$ E186$^H$ such that ligand recognition elements are dismantled. The other catalytically inactive form of SXA is the "dianionic" form (D14$^-$ E186$^-$). D14$^-$ E186$^-$ binds 4NPA weakly, if at all, but it binds 4NPX with ~2-fold greater affinity than the D14$^-$ E186$^H$ enzyme. We speculate that D14$^-$ E186$^-$ may bind the xylose residue of 4NPX in subsite +1 (or portions thereof) to avoid clash between the negative charges of the carboxylic acids (belonging to D14 and E186) in subsite −1 and the oxygen atoms of the sugar moiety. Certainly, subsite +1 has affinity for D-xylose as seen in the 13-fold larger $k_{cat}$ and 2-fold larger $k_{cat}/K_m$ of SXA acting on X2 in comparison to 4NPX. Subsite +1 of SXA may have little or no affinity for arabinofuranose, as suggested by the 36-fold larger $k_{cat}$ and 13-fold larger $k_{cat}/K_m$ of SXA acting on 4NPA in comparison to A2. Repulsion of 4NPA from subsite −1 of the D14$^-$ E186$^-$ enzyme, without binding affinity for subsite +1 to form a nonproductive complex, would account for the pH independence of $k_{cat}$ above pH 4 for SXA acting on 4NPA. In any case, the catalytically inactive D14$^-$ E186$^-$ has ligand binding properties, which distinguish it from the apparently functionless D14$^H$ E186$^H$.

TABLE 1

Primers Used for Site-Directed Mutagenesis of SXA[a]

| Mutation | Primer sequence (5'→3') | SEQ. ID No. |
|---|---|---|
| D14A | GGCTTTAACCCC<u>GC</u>CCCAGCATTGTC GACAATGCTG<u>GG</u>GCGGGGTTAAAGCC | 3 |
| D127A | CGGTGCTGGCTTT<u>GC</u>AGCCTCCCTGTTCC GGAACAGGGAGGC<u>TG</u>CAAAGCCAGCACCG | 4 |
| E186A | GATATTGCCTATAC<u>CGC</u>CGGTCCCCACCTTTAC GTAAAGGTGGGGACC<u>GGC</u>GGTATAGGCAATATC | 5 |
| H248A | CCCTGCAGAAATGCGGC<u>GC</u>AGCATCATTAGTCGAAAC GCGCGTTTCGACTAATGATGC<u>TGC</u>GCCGCATTTCTGCAGGG | 6 |
| R290A | TGTCCGCTGGGC<u>GC</u>AGAAACCGCCATCCA TGGATCGCGGTTTC<u>TGC</u>GCCCAGCGGACA | 7 |

[a]Underlined nucleotides indicate mutations incorporated into primers.

TABLE 2

Survey of 4NP-Glycosides as Potential Substrates of SXA[a]

| 4NP-Glycoside (5 mM) | Relative Rate[b] |
|---|---|
| 4-Nitrophenyl-β-D-xylopyranoside (4NPX) | 1.00 ± 0.01 |
| 4-Nitrophenyl-α-L-arabinofuranoside (4NPA) | 0.101 ± 0.003 |
| 4-Nitrophenyl-β-L-arabinopyranoside[c] | <10$^{-6}$ |
| 4-Nitrophenyl-α-L-fucopyranoside | <10$^{-6}$ |
| 4-Nitrophenyl-α-L-arabinopyranoside | <10$^{-6}$ |
| 4-Nitrophenyl-β-D-glucopyranoside | <10$^{-6}$ |
| 4-Nitrophenyl-β-D-mannopyranoside | <10$^{-6}$ |
| 4-Nitrophenyl-α-D-xylopyranoside | <10$^{-6}$ |
| 4-Nitrophenyl-β-D-fucopyranoside | <10$^{-6}$ |
| 4-Nitrophenyl-α-D-galactopyranoside | <10$^{-6}$ |
| 4-Nitrophenyl-β-D-galactopyranoside | <10$^{-6}$ |
| 4-Nitrophenyl-α-D-mannopyranoside | <10$^{-6}$ |
| 4-Nitrophenyl-α D-glucopyranoside | <10$^{-6}$ |
| 4-Nitrophenyl-α-L-rhamnopyranoside | <10$^{-6}$ |
| 4-Nitrophenyl-β-fucopyranoside | <10$^{-6}$ |

[a]Reactions contained 5 mM 4NP glycoside in 100 mM succinate-NaOH, pH 5.3 and 25° C. Initial rates were determined by using Method A.
[b]Initial rates are expressed as relative to that of 4NPX (25.1 s$^{-1}$). Standard deviations of replicates are indicated. Limit of detection <10$^{-6}$, estimated from having 1.2-2.4 × 10$^3$ fold larger enzyme concentrations, (7.7-15.4 μM), 100-fold longer reaction times, and the ability to detect 10-fold smaller changes in absorbance per min in comparison to 4NPX reactions.
[c]This glycoside was contaminated with a small percentage (0.08%) of a 4NP substrate that was hydrolyzed by SXA. To determine substrate activity for the remaining 99.9%, samples were incubated with a high concentration of SXA (7.7 μM) to consume the impurity and the hydrolysis rate was determined from the reaction progression that followed.

TABLE 3

Influence of Viscosity on SXA Steady-State Kinetic Parameters[a]

| Substrate/Exper. No. | $\eta/\eta_o$[b] | $k_{cat}$ (s$^{-1}$) | $k_{cat}$ Rel. to $\eta/\eta_o = 1$ | $k_{cat}/K_m$ (s$^{-1}$mM$^{-1}$) | $k_{cat}/K_m$ Rel. to $\eta/\eta_o = 1$ | $K_m$ (mM) |
|---|---|---|---|---|---|---|
| 4NPX/1[c] | 1.00 | 32.8 ± 0.6 | 1.00 | 44.1 ± 2.4 | 1.00 | 0.742 ± 0.041 |
| 4NPX/1[c] | 6.12 | 29.8 ± 0.5 | 0.910 ± 0.0152 | 43.1 ± 2.2 | 0.980 ± 0.050 | 0.690 ± 0.035 |
| 4NPX/2[d] | 1.00 | 32.9 ± 0.5 | 1.00 | 47.1 ± 1.7 | 1.00 | 0.699 ± 0.035 |
| 4NPX/2[d] | 6.85 | 30.1 ± 1.1 | 0.920 ± 0.040 | 41.6 ± 3.5 | 0.880 ± 0.080 | 0.637 ± 0.081 |
| 4NPA/2[d] | 1.00 | 2.99 ± 0.05 | 1.00 | 4.01 ± 0.14 | 1.00 | 0.745 ± 0.036 |
| 4NPA/2[d] | 6.85 | 2.87 ± 0.12 | 0.960 ± 0.040 | 3.81 ± 0.37 | 0.950 ± 0.100 | 0.754 ± 0.101 |

[a]Viscosity was varied by the absence or presence of 50% (wt/vol) sucrose in the reaction mixtures. Initial-rate data were fitted to Eq. 1 for determination of kinetic parameters. Standard errors are indicated.
[b]Viscosity of reaction solution relative to that of water.
[c]Reactions contained variable concentrations of 4NPX in 100 mM succinate-NaOH, pH 5.3 at 25° C. Initial rates were determined by Method A.
[d]Reactions contained variable concentrations of 4NPX or 4NPA in 100 mM MES-NaOH, pH 6.00 at 25° C. Initial rates were determined by Method B.

TABLE 4

Effect of Site-Directed Mutations of SXA on Steady-State Kinetic Parameters with Substrate 4NPX[a]

| SXA | $k_{cat}$ (s$^{-1}$) | $k_{cat}/K_m$ (s$^{-1}$mM$^{-1}$) | $K_m$ (mM) |
|---|---|---|---|
| Wild-Type | 31.1 ± 0.4 | 40.7 ± 1.6 | 0.763 ± 0.031 |
| D14A | 0.00954 ± 0.00016 | 0.0123 ± 0.0006 | 0.777 ± 0.036 |
| E186A | 0.00267 ± 0.00005 | 0.00242 ± 0.00012 | 1.10 ± 0.05 |
| D127A | 0.000129 ± 0.000003 | 0.000150 ± 0.000010 | 0.881 ± 0.059 |
| H248A | 0.0950 ± 0.0025 | 0.0909 ± 0.0063 | 1.05 ± 0.07 |
| R290A[b] | 0.0126 ± 0.0020 | 0.000250 ± 0.000044 | 50.3 ± 8.8 |

[a]Reactions contained varied concentrations of 4NPX in 100 mM succinate-NaOH, pH 5.3 and 25° C. Initial rates, determined by using Method A, were fitted to Eq. 1 for determination of kinetic parameters. Standard errors are indicated.
[b]Values of $k_{cat}$ and $K_m$ were not well determined for R290A because the highest concentration of 4NPX examined (5 mM) is far below the estimated $K_m$.

TABLE 5

Effect of Site-Directed Mutations of SXA on Steady-State Kinetic Parameters With Substrate 4NPA[a]

| SXA | $k_{cat}$ (s$^{-1}$) | $k_{cat}/K_m$ (s$^{-1}$mM$^{-1}$) | $K_m$ (mM) |
|---|---|---|---|
| Wild-Type | 2.68 ± 0.06 | 3.30 ± 0.20 | 0.810 ± 0.050 |
| D14A | 0.000936 ± 0.000012 | 0.00121 ± 0.00005 | 0.771 ± 0.029 |
| E186A | 0.000239 ± 0.000008 | 0.000180 ± 0.000015 | 1.32 ± 0.11 |

[a]Reactions contained varied concentrations of 4NPA in 100 mM succinate-NaOH, pH 5.3 and 25° C. Initial rates, determined by using Method A, were fitted to Eq. 1 for determination of kinetic parameters. Standard errors are indicated.

TABLE 6

Steady-State kinetic Parameters of SXA Acting on Natural Substrates[a]

| Substrate | $k_{cat}$ (s$^{-1}$) | $k_{cat}/K_m$ (s$^{-1}$mM$^{-1}$) | $K_m$ (mM) |
|---|---|---|---|
| X2 | 412 ± 18 | 99 ± 8 | 4.2 ± 0.5 |
| X3 | 172 ± 14 | 45 ± 4 | 3.8 ± 0.6 |
| X4 | 150 ± 5 | 38 ± 1 | 4.0 ± 0.3 |
| X5 | 150 ± 15 | 41 ± 3 | 3.7 ± 0.6 |
| X6 | 96 ± 7 | 35 ± 4 | 2.7 ± 0.5 |
| A2 | 0.074 ± 0.003 | 0.062 ± 0.005 | 1.2 ± 0.1 |

[a]Reactions contained variable concentrations of substrate in 100 mM succinate-NaOH, pH 5.3 at 25° C. Initial-rate data were fitted to Eq. 1. Standard errors are indicated.

Example 2

Materials and General Methods

The gene encoding β-xylosidase from *S. ruminantium* GA192 was cloned and expressed in *Escherichia coli* as described (Whitehead and Cotta, 2001, ibid). SXA, produced in *E. coli*, was purified to homogeneity, as judged from SDS-PAGE analysis, by using reverse phase and anionic exchange chromatography steps. Concentrations of homogeneous SXA monomers (active sites) were determined by using an extinction coefficient at 280 nm of 129600 M$^{-1}$ cm$^{-1}$, calculated from amino acid composition (Gill and von Hippel, 1989, ibid). N-terminal Edman sequencing was conducted by the Wistar Proteomics Facility (Philadelphia, Pa.). Buffers and 4-nitrophenyl-β-D-xylopyranoside (4NPX) were obtained from Sigma-Aldrich (St. Louis, Mo.). All other reagents were reagent grade and high purity. A Cary 50 Bio UV-Visible spectrophotometer (Varian; Palo Alto, Calif.), equipped with a thermostatted holder for cuvettes, was used for spectral and kinetic determinations. Delta extinction coefficients (product-substrate) at 400 nm were determined for each buffer condition by subtracting the molar absorbance of 4NPX from that of 4-nitrophenol (4NP). The concentration of 4NP was determined by using the published extinction coefficient of 18.3 mM$^{-1}$ cm$^{-1}$ at 400 nm for 4NP in NaOH (Kezdy and Bender, 1962, ibid). The concentration of 4NPX was determined by incubating the substrate with excess enzyme until an end point was reached, adding an aliquot (0.01 to 0.1 mL) to 0.1 M NaOH, recording the absorbance at 400 nm and using the extinction coefficient of 18.3 mM$^{-1}$ cm$^{-1}$ for 4NP. Data were fitted to linear and nonlinear equations by using the computer program Grafit (Erithacus Software; Surrey, UK). Manipulations of X-ray structure coordinates (overlays, distance measurements, etc.) were through Swiss-PDB Viewer 3.7 (Guex, N. and Peitsch, M. C. (1997), *Electrophoresis* 18:2714-2723). The Stokes radius was calculated from X-ray coordinates by using the computer program HYDROPRO, Version 7.C (García de la Torre, J., Huertas, M. L., and Carrasco, B. (2000), *Biophysical J.* 78:719-730).

The equation numbers referred to in this Example refer to the equations shown hereinbelow, and may not correspond to those equation numbers referred to in Examples 1 and 3).

Molecular Mass, Quaternary Structure, and Isoelectric Point of SXA

SDS-PAGE analysis was conducted by using a Criterion gel system, Criterion Tris-HCl 8-16% polyacrylamide gels, Bio-Safe stain, and protein molecular weight standards (all from Bio-Rad Laboratories; Hercules, Calif.). The Stokes radius of SXA was determined by using a gel filtration method: the column (2.6×62 cm) was packed with Toyapearl 55F resin (Tosoh Bioscience; Montgomeryville, Pa.) and equilibrated with 100 mM sodium phosphate, pH 7.0 at 24-26° C. (room temperature) with a flow rate of 2.0 mL/min. Post-column eluate was monitored continuously for absorbance at 260, 280, and 405 nm. Elution volumes ($V_e$) were recorded and transformed to $K_{av}$ values by using equation 1, where $V_e$ is the recorded elution volume, $V_0$ is the void volume of the column, and $V_t$ is the total volume of the column plus tubing to the absorbance monitor. The value for $V_0$ was determined as 112 mL by using blue dextran 2000. The value of $V_t$ was determined as 330 mL. Protein standards of known Stokes radius ($R_S$) and molecular weight (MW) were obtained from GE Healthcare Life Sciences (Piscataway, N.J.): ferritin ($R_S$=61.0 Å, MW=440 kDa), catalase ($R_S$=52.2 Å, MW=232 kDa), and aldolase ($R_S$=48.1 Å, MW=158 kDa). The Stokes radius of SXA was determined from the linear regression of protein standards fitted to equation 2 where $K_{av}$ is the transformed value of $V_e$, $R_S$ is the Stokes radius, m is the slope and C is the constant of the standard line.

$$K_{av} = \frac{V_e - V_0}{V_t - V_0} \quad (1)$$

$$(-\log K_{av})^{1/2} = m * Rs + C \quad (2)$$

Isoelectric focusing (IEF) was conducted by using a Criterion electrophoresis system, Criterion pH 3-10 gels, IEF standards, and Coomasie R-250/Crocein Scarlet IEF gel stain (Bio-Rad; Hercules, Calif.).

pH Stability of SXA

Buffers of constant ionic strength (I=0.3 M), adjusted with NaCl, were used as indicated: 100 mM succinate-NaOH (pH 3.5-6), 100 mM sodium phosphate (pH 6-8), 30 mM sodium pyrophosphate (pH 8-9), and 100 mM glycine-NaOH (pH 9-10). For preincubation, an aliquot (7 µL) of SXA (168 µM with respect to monomer concentration in 50 mM Tris-HCl, pH 7.5) was added to 100 µL of buffered solutions at varied pH and 25° C. For ligand protection studies, varied concentrations of D-xylose or D-glucose were included in or omitted from the 100-µL preincubation mixtures containing 100 mM succinate-NaOH, pH 4.0, adjusted with NaCl to I=0.3 M. At varied times after enzyme addition, 7 µL of preincubation mixtures were added to 1-mL reaction mixtures containing 100 mM sodium phosphate, pH 7.0, adjusted with NaCl to I=0.3 M (Buffer A), and 1.95 mM 4NPX at 25° C. Initial rates were determined by monitoring reactions continuously at 400 nM for 0.3 min. For determination of the expression, "relative activity remaining", initial rates were divided by the rate of enzyme preincubated in Buffer A at 0° C. and assayed in 1-mL reaction mixtures containing the concentration of monosaccharide (corresponding to the carryover from enzyme preincubated in monosaccharide), the concentration of preincubation buffer (corresponding to the carryover from preincubated enzyme), and 1.95 mM 4NPX in Buffer A at 25° C. Relative activity remaining data were fitted to equation 3, which describes a first order decay: A is the relative activity remaining at varied times of preincubation, $A_0$ is the relative activity remaining at time zero of the preincubation, $k_{obs}$ is the first order rate constant, and t is the time of preincubation. Apparent affinities for D-xylose and D-glucose were determined by fitting $k_{obs}$ values from the monosaccharide protection studies to equation 4 where $k_{obs}$ is the observed first order rate constant for the decay, $k_0$ is the first order rate constant in the absence of ligand (e.g., D-xylose), I is the ligand concentration in the preincubation mixture, and $K_i$ is the dissociation constant of ligand from the enzyme-ligand complex.

$$A = A_0 * e^{-k_{obs}*t} \quad (3)$$

$$k_{obs} = \frac{k_0}{1 + I/Ki} \quad (4)$$

To determine the effect on steady-state kinetic parameters caused by low pH treatment, SXA was preincubated in 100 mM succinate-NaOH, pH 4.0 (adjusted with NaCl to I=0.3 M) at 25° C. until ~50% of its catalytic activity was degraded (assessed from reactions containing 1.95 mM 4NPX in Buffer A at 25° C.), the pH of the preincubation mixture was raised by adding an equal volume of Buffer A at 0° C., 7 µL of the neutralized mixture were added to 1-mL reactions containing varied concentrations of 4NPX (0.2-5.0 mM) in Buffer A at 25° C., and the reactions were monitored continuously at 400 nm for 0.3 min to determine initial rates. Initial rates of catalysis were fitted to equation 5 where v is the initial rate at a specified concentration of 4NPX, $k_{cat}$ is the rate of catalysis when enzyme is saturated with substrate, S is the substrate concentration, and $K_m$ is the Michaelis constant. The parameter, $k_{cat}$, is expressed in moles of substrate hydrolyzed per second per mole of enzyme active sites (monomers), calculated using the delta extinction coefficient for 4NP-4NPX at 400 nm and the extinction coefficient for SXA at 280 nm.

$$v = \frac{k_{cat} * S}{K_m + S} \quad (5)$$

Thermal Stability of SXA

For preincubation, 7 µL of SXA (168 µM with respect to monomer concentration in 50 mM Tris-HCl, pH 7.5) were added to 100 mL of 100 mM succinate-NaOH, pH 5.3 (adjusted with NaCl to I=0.3 M) at varied temperatures. Ligand protection studies contained varied concentrations of D-xylose or D-glucose in the pH 5.3 preincubation buffer at 55° C. At varied times after enzyme addition, 15 µL of the preincubation mixtures were added to 15 µL of Buffer A at 0° C., 7 µL of the enzyme mixture at 0° C. were added to 1-mL reaction mixtures containing 1.95 mM 4NPX in Buffer A at 25° C., and initial rates were determined by monitoring reactions continuously at 400 nM for 0.3 min. The expression, "relative activity remaining", $k_{obs}$, and $K_i$ were determined from the initial rate data as described above in the pH Stability of SXA section.

To determine the effect on steady-state kinetic parameters caused by heat treatment, SXA was preincubated in 100 mM succinate-NaOH, pH 5.3 (I=0.3 M) at 55° C. until ~50% of its catalytic activity was degraded (assessed from reactions containing 1.95 mM 4NPX in Buffer A at 25° C.), the temperature of the preincubation mixture was lowered by adding an equal volume of Buffer A at 0° C., 7 µL of the cooled enzyme mixture were added to 1-mL reactions containing varied concentrations of 4NPX (0.2-5.0 mM) in Buffer A at 25° C., and the reactions were monitored continuously at 400 nm for 0.3 min to determine initial rates of catalysis. Steady-state kinetic parameters were determined by fitting initial-rate data to equation 5 as described above in the pH Stability of SXA section.

Inhibition of SXA-Catalyzed Hydrolysis of 4NPX by D-Glucose and D-Xylose

The 1-mL reaction mixtures at 25° C. contained varied concentrations of 4NPX and varied concentrations of D-glucose or D-xylose in buffers of constant ionic strength (I=0.3 M, adjusted with NaCl) as indicated above in the pH Stability of SXA section. Reactions were initiated by addition of 7 µL of SXA, preincubated in 10 mM sodium phosphate, pH 7.0 and 0° C. Reactions were monitored continuously for 0.3 min at 400 nm to determine initial rates. Initial-rate data were fitted to equation 6, where v is the initial rate, $k_{cat}$ is the rate of the reaction when saturated with substrate, S is the substrate concentration, $K_m$ is the Michaelis constant, I is the inhibitor concentration (e.g., D-glucose), and $K_i$ is the dissociation constant of inhibitor from the enzyme-inhibitor complex.

$$v = \frac{k_{cat} * S}{K_m * \left(1 + \frac{I}{K_i}\right) + S} \quad (6)$$

Results and Discussion

The gene encoding for SXA predicts a protein of 538 amino acids and a molecular mass of 61140 Da. Edman sequencing of the first 10 residues starting at the N terminus of SXA indicated the sequence, MNIQNPVLKG, which agrees with the sequence predicted from the gene and indicates that SXA is produced by E. coli with an intact N terminus. SDS-PAGE analysis shows that the purified SXA is homogeneous with a molecular mass of ~60 kDa (FIG. 11A).

We chose the structure of β-xylosidase from C. acetobutylicum (PDB ID: 1YI7) for modeling of SXA because of its 72% protein sequence identity to SXA; as well, within a 9 Å sphere of the active site of 1YI7, all 21 residues are identical in the sequence of SXA. The X-ray coordinates of β-xylosidase from C. acetobutylicum contain 534 amino acid residues per subunit of the homotetramer, four fewer residues per subunit than the sequence of SXA. The longest axis of the homotetramer of β-xylosidase from C. acetobutylicum is calculated as 123 Å by using the computer program HYDROPRO, and the longest distance, perpendicular to this axis, is ~90 Å as measured from the coordinates of the tetramer. We determined the Stokes radius of SXA by using a gel filtration method (FIG. 11B). The determined value of 55.4±0.5 Å for the Stokes radius of SXA is similar to the value of 52 Å, calculated by using HYDROPRO and the X-ray structure coordinates of homotetrameric β-xylosidase from C. acetobutylicum; consistent with SXA occurring as a homotetramer in solution.

The isoelectric point of native SXA (estimated as ~4.4) is slightly lower than the lowest isoelectric point (4.5) of the protein standards, but clearly well above the lowest pH (pH=3) of the gel (FIG. 12A). SXA is inactivated by conditions of low pH and high temperature, with a sharp drop in activity between pH 4.0 and 4.3 (FIG. 12B) and a broad drop between 50 and 60° C. (FIG. 13). Loss of catalytic activity at low pH and high temperature was associated with cloudiness in the preincubation mixtures, suggesting that SXA denatures and precipitates. To determine the effect of partially inactivated SXA on steady-state kinetic parameters, the enzyme was preincubated at pH 4.0 and 25° C. or at pH 5.3 and 55° C. until ~50% of its catalytic activity remained in each sample. The preincubated samples of SXA were pH neutralized and cooled prior to determination of kinetic parameters by fitting initial-rate data to equation 5 for comparison with an untreated SXA control sample: partially pH-inactivated SXA ($k_{cat}$=6.36±0.041 s$^{-1}$, $K_m$=0.366±0.014 mM); partially temperature-inactivated SXA ($k_{cat}$=5.39±0.062 s$^{-1}$, $K_m$=0.386±0.084 mM); and untreated control SXA ($k_{cat}$=12.2±0.05 s$^{-1}$, $K_m$=0.380±0.005 mM). Thus, inactivation by low pH or high temperature is attributed to degradation of the $k_{cat}$ parameter without changing $K_m$, consistent with the view that, upon limited exposure to the extreme conditions, a portion of the protein denatures and does not contribute to the catalyzed hydrolysis of 4NPX. Complementary experiments have shown that inactivation of SXA by low pH or high temperature is not reversible by simply neutralizing the pH or cooling.

Figure 14A:
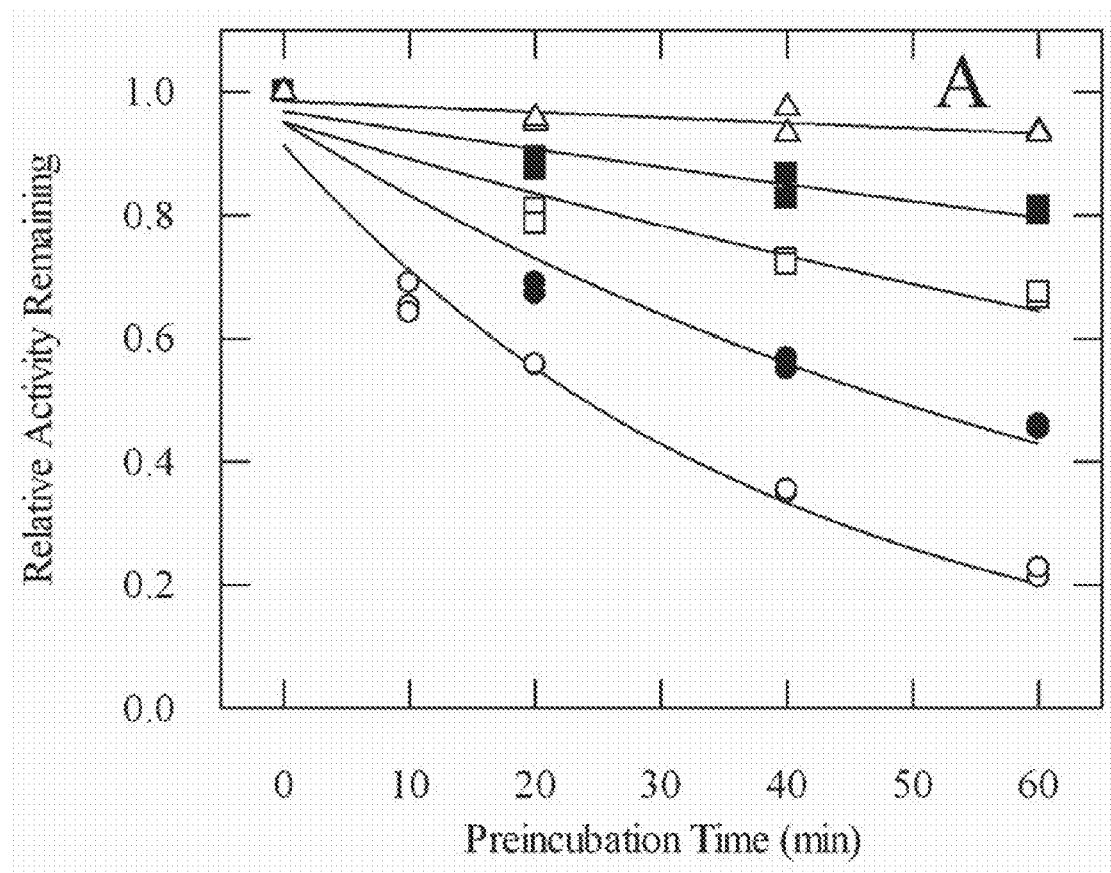
Figure 14B:
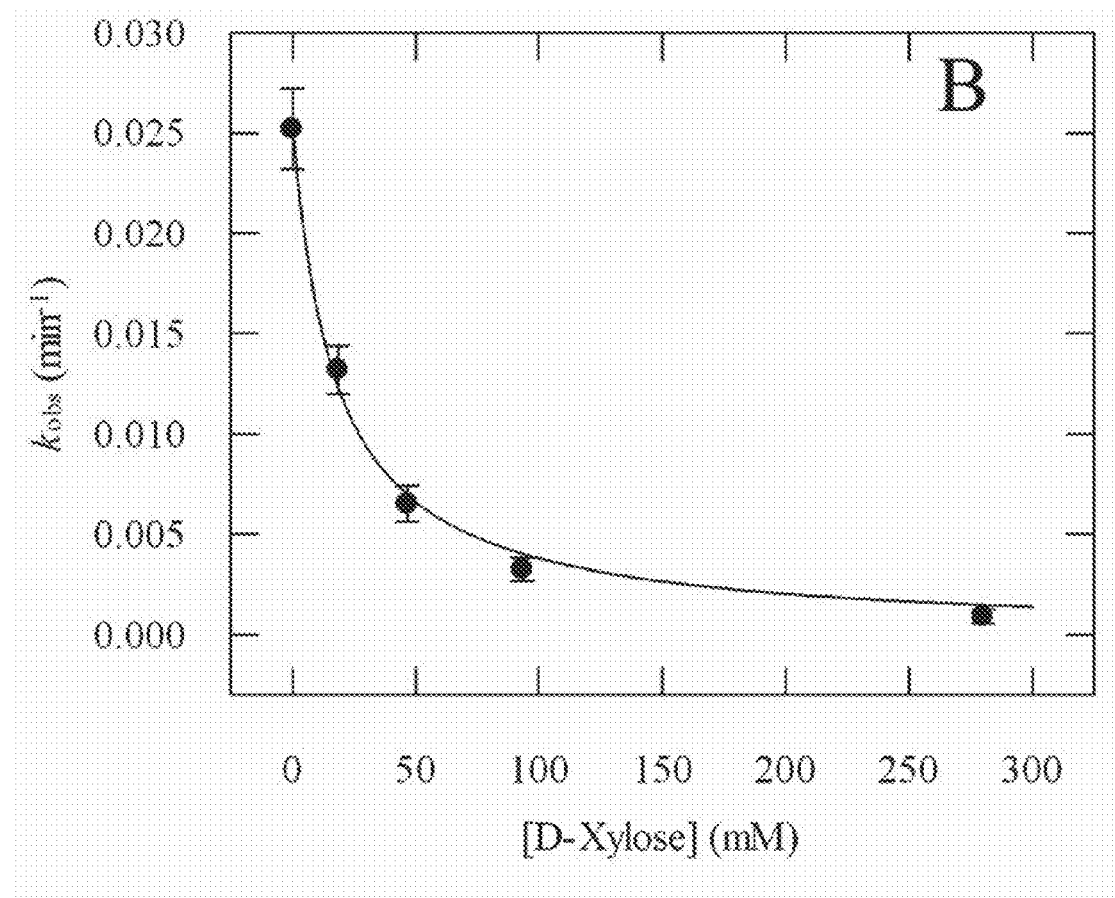
Figure 15A:
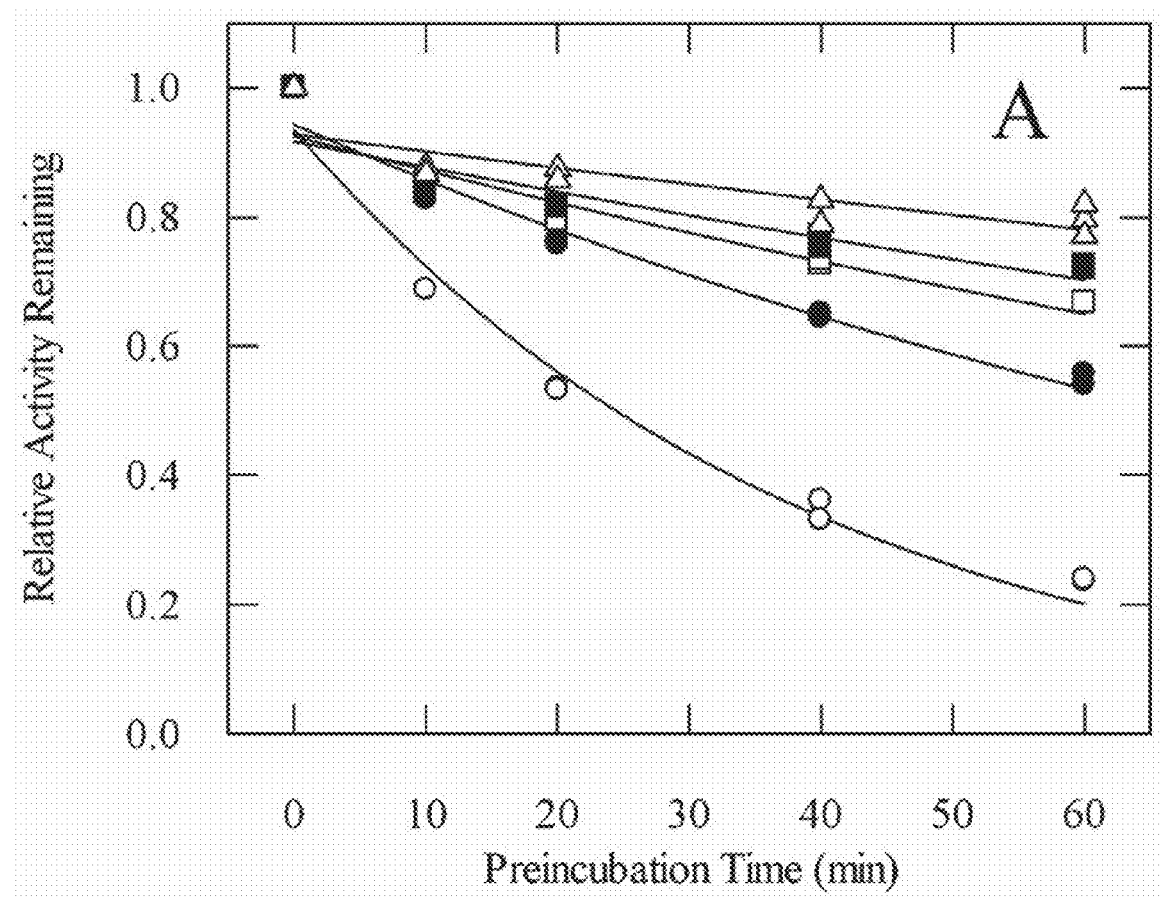
Figure 15B:
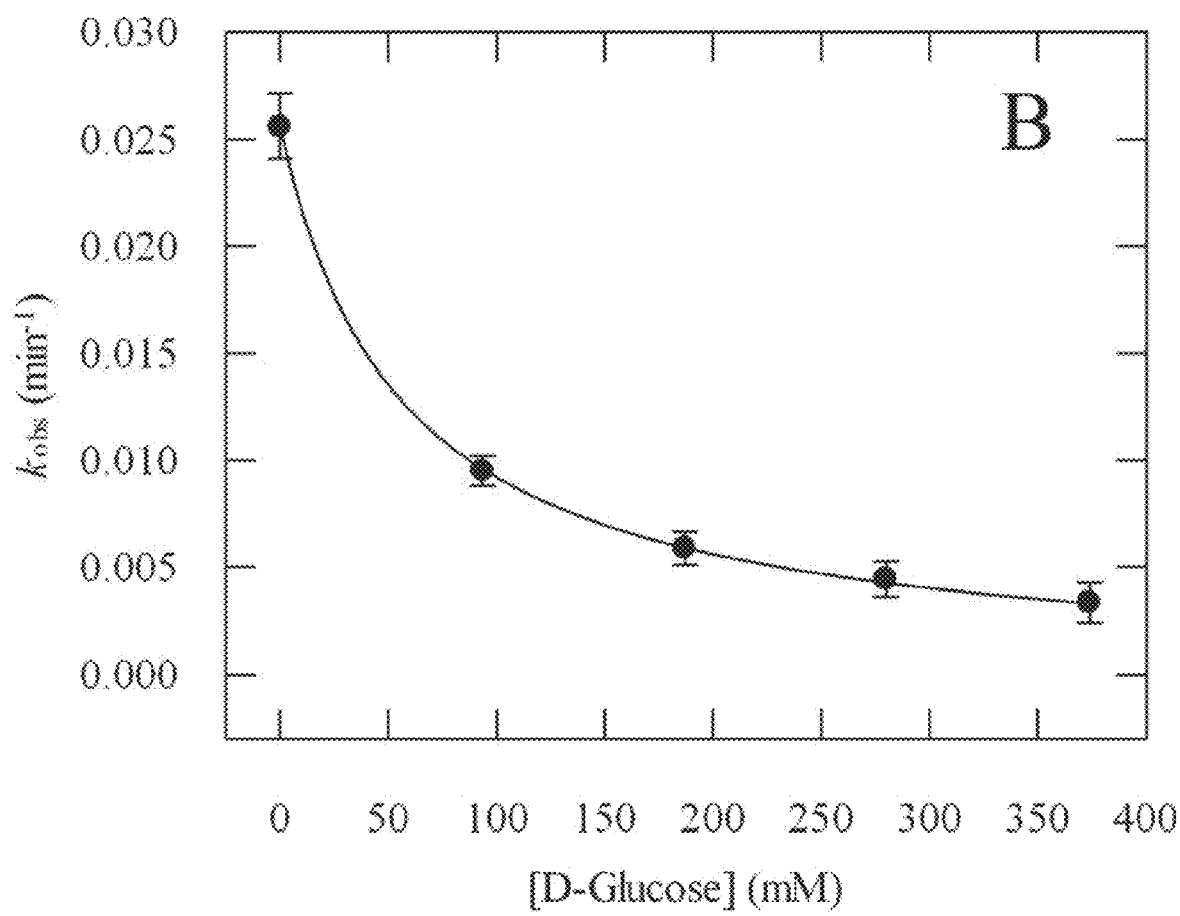

At pH 5.3 and 55° C., SXA is inactivated in a first-order process with a rate constant of 0.0252±0.0020 min$^{-1}$ (FIG. 14A). SXA was protected from thermal denaturation by including in the preincubation mixture varied concentrations of D-xylose. Protection from temperature denaturation was dependent on the concentration of D-xylose (FIG. 14A), and as the concentration of D-xylose approached saturation the decay rate approaches zero (FIG. 14B), in accordance with equation 4, which estimates a dissociation constant ($K_i$=17.6±1.8 mM) for D-xylose from the $k_{obs}$ values (FIG. 14B). This 55° C. value compares with a 25° C. value ($K_i$=7.62±0.26 mM) for inhibition of SXA-catalyzed hydrolysis of 4NPX at pH 5.3 and 25° C. by D-xylose. Similarly, SXA was protected from thermal denaturation by including in the preincubation mixture varied concentrations of D-glucose (FIG. 15A). A dissociation constant ($K_i$=56.1±0.8 mM) was estimated for D-glucose from fitting the $k_{obs}$ values to equation 4 (FIG. 15B). This 55° C. value compares with a 25° C. value ($K_i$=79.0±2.3 mM) for inhibition of SXA-catalyzed hydrolysis of 4NPX at pH 5.3 and 25° C. by D-glucose.

Figure 16A:
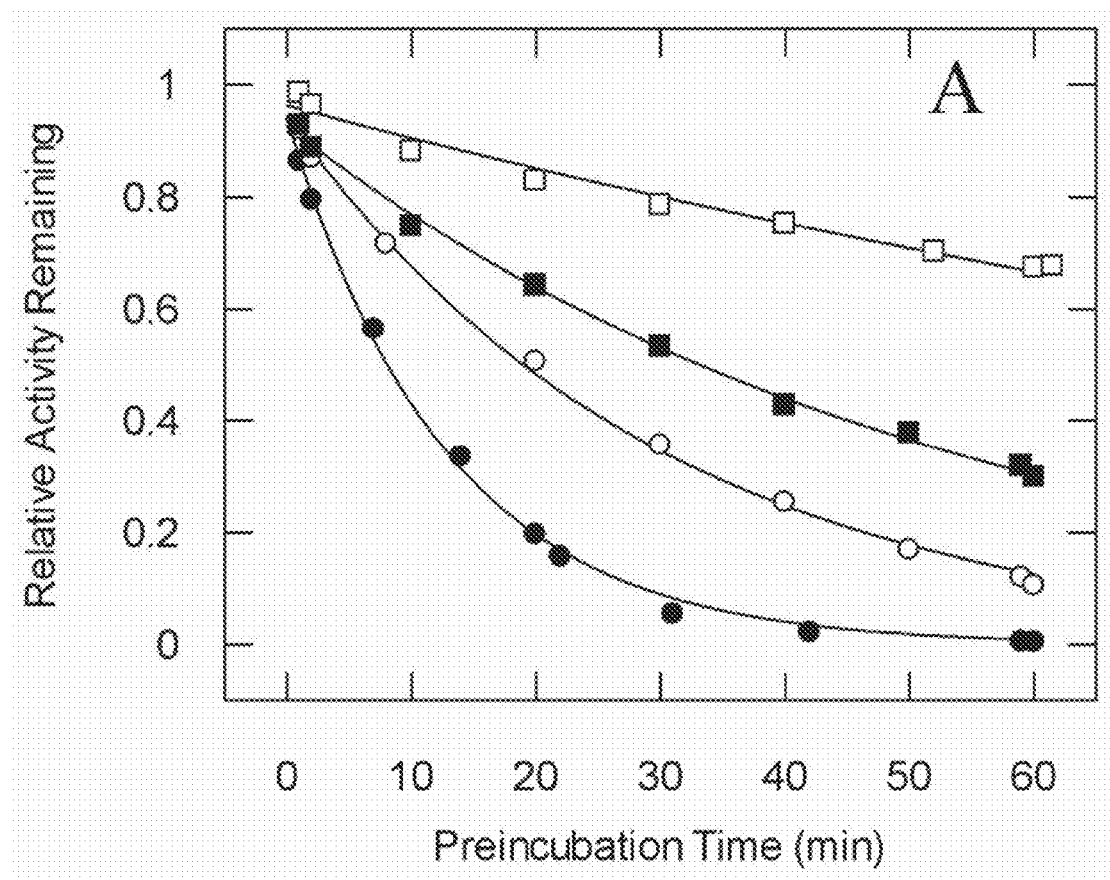
Figure 16B:
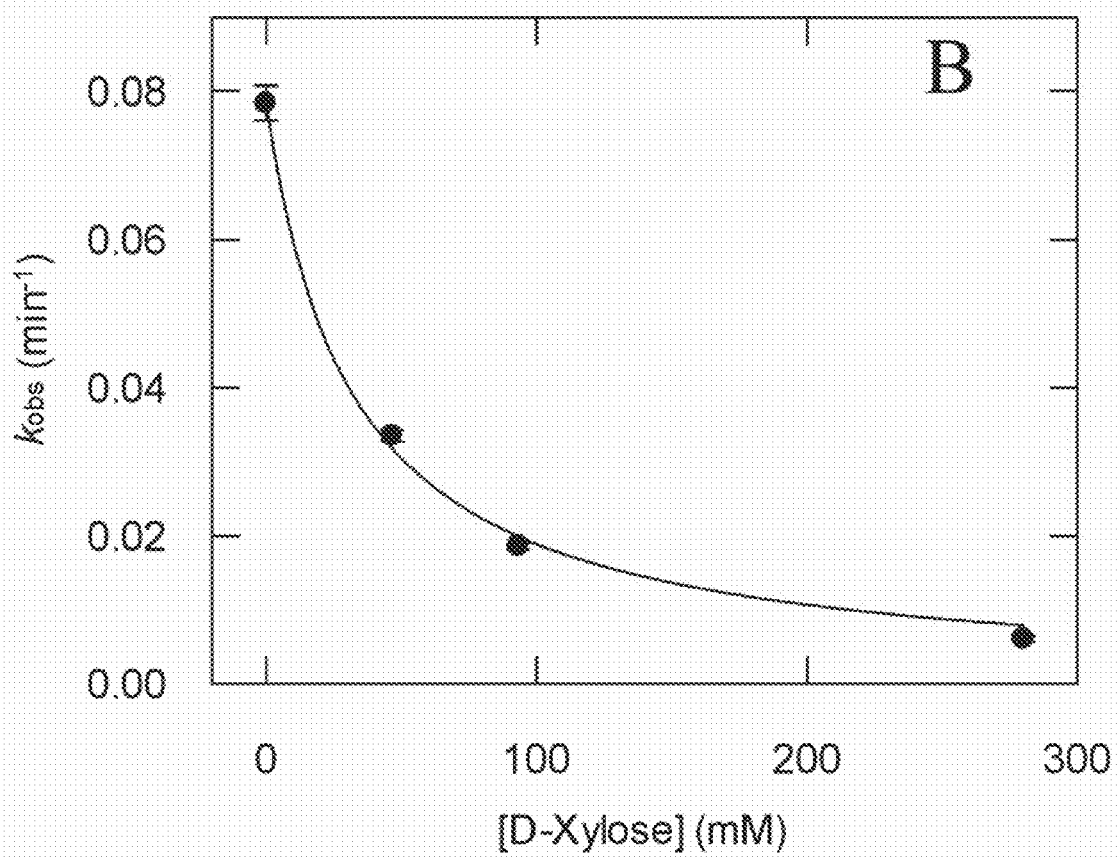
Figure 17A:
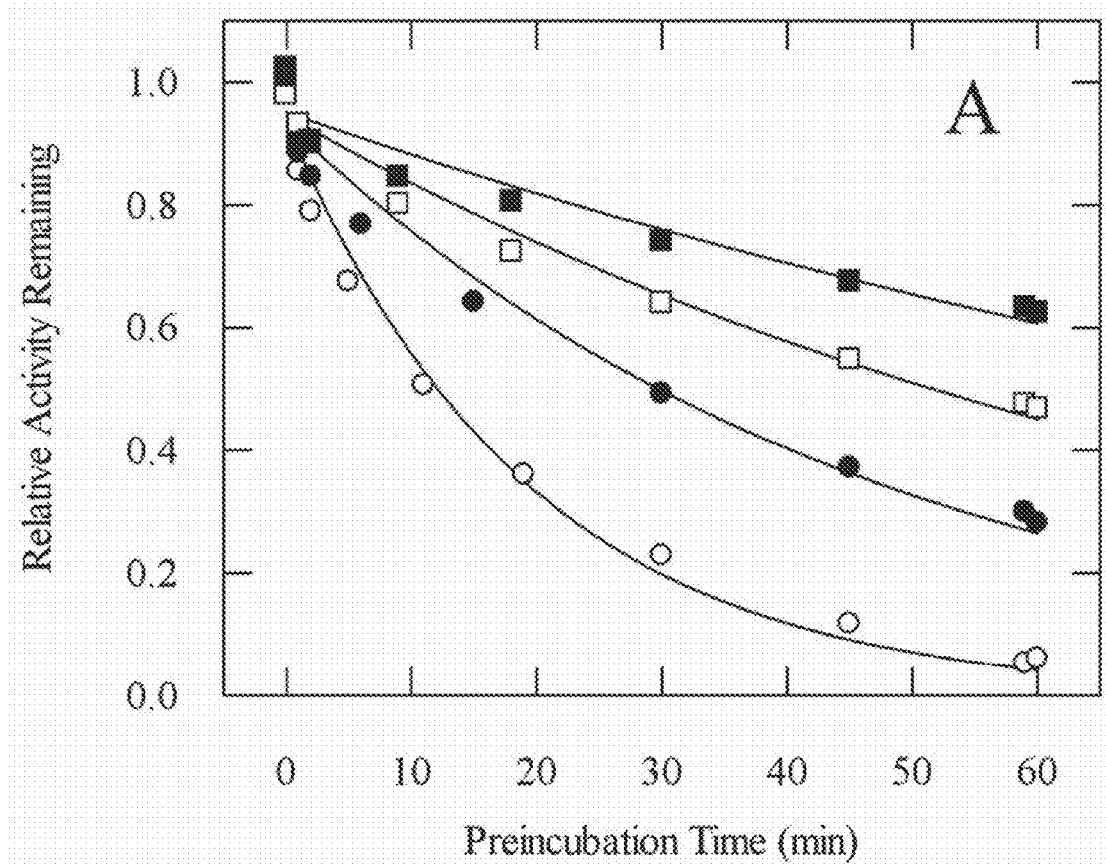
Figure 17B:
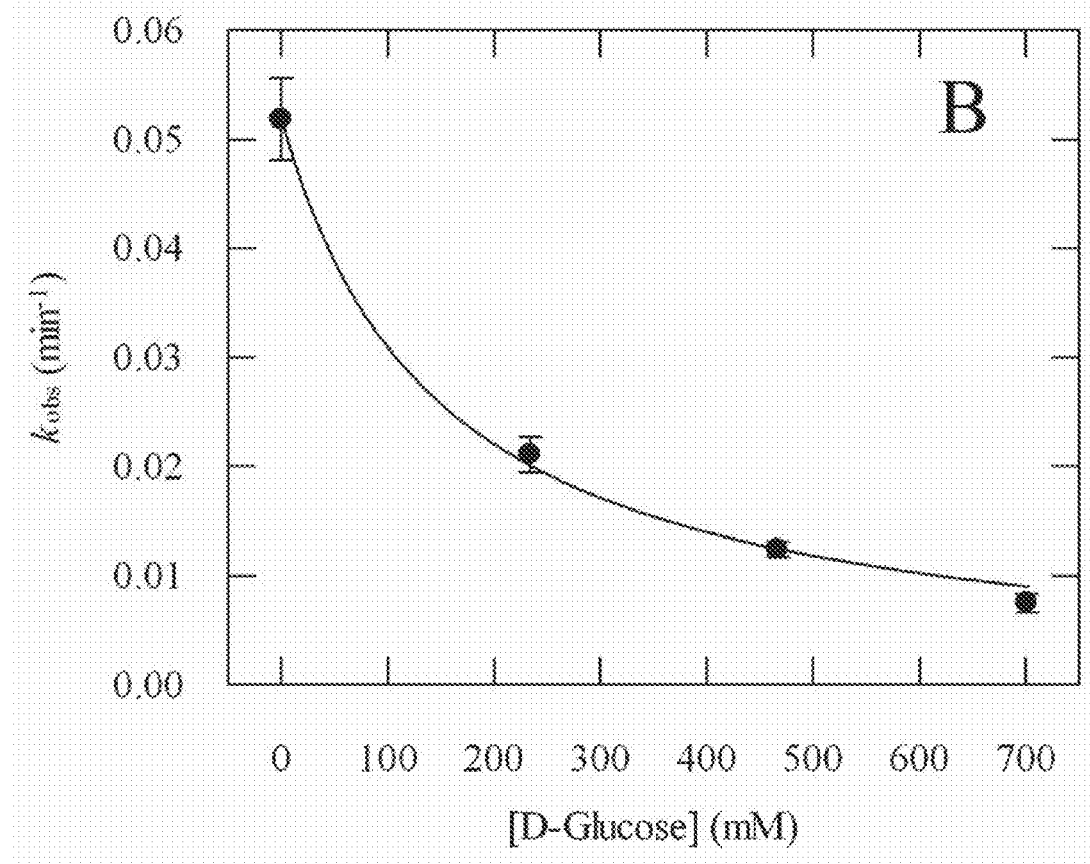

At pH 4.0 and 25° C., SXA is inactivated in a first-order process with a rate constant of 0.0784±0.0023 min$^{-1}$, and protection from denaturation at low pH is dependent on the concentration of D-xylose (FIG. 16A). Protection from pH denaturation by D-xylose is saturable with a first-order decay rate of zero at saturating D-xylose in accordance with equation 4, which estimates a dissociation constant ($K_i$=31.7±2.8 mM) for D-xylose (FIG. 16B). This pH 4.0 value compares with a pH 4.3 value ($K_i$=43.5±1.1 mM) for inhibition of SXA-catalyzed hydrolysis of 4NPX at pH 4.3 and 25° C. by D-xylose. Similarly, inactivation rates of SXA at pH 4.0 and 25° C. are slowed by D-glucose (FIG. 17A). A dissociation constant ($K_i$=147±12 mM) was estimated for D-glucose from fitting the $k_{obs}$ values to equation 4 (FIG. 17B). This pH 4.0 value compares with a pH 4.3 value ($K_i$=330±8 mM) for inhibition of SXA-catalyzed hydrolysis of 4NPX at pH 4.3 and 25° C. by D-glucose.

The influence of pH on inhibition of SXA-catalyzed hydrolysis of 4NPX by D-glucose and D-xylose was determined at 25° C. by using buffers of constant ionic strength (I=0.3 M). D-Glucose and D-xylose inhibited the catalyzed reaction competitively with respect to substrate 4NPX at all pH values examined in accordance with equation 6. $K_i$ values for glucose decrease with increasing pH as follows: pH 4.3 (330±8 mM), pH 5.3 (79.0±2.3 mM), pH 7.0 (34.5±0.7 mM), and pH 9.0 (18.7±0.6 mM). Similarly, affinities of SXA for D-xylose increase with increasing pH as seen in the progression of $K_i$ values: pH 4.3 (43.5±1.1 mM), pH 5.3 (7.62±0.26 mM), pH 7.0 (3.82±0.06 mM), and pH 9.0 (3.21±0.14 mM).

Temperature and pH profiles of SXA stability place certain constraints on its application to processes for saccharification of the hemicellulose component of herbaceous biomass, as do $K_i$ values for D-glucose and D-xylose inhibition of SXA catalysis. Potentially, if saccharification processes require higher temperatures or lower pH than the native SXA withstands, SXA could be modified to better accommodate such assaults on its stability. Similarly, inhibition of catalysis by D-glucose and D-xylose, which constitute two major constituents of herbaceous biomass, potentially could be alleviated by protein engineering approaches. Three-dimensional models of SXA could aid in the design of such modifications. Native SXA is an efficient catalyst for the hydrolysis of xylooligosaccharides, details of which will be reported soon. Owing to the nature of SXA, negative influences of temperature and pH on protein stability and negative influences of inhibition of catalysis by D-glucose and D-xylose are not additive. That is, under conditions of low pH and/or high temperature, the presence of D-glucose and D-xylose could serve to stabilize SXA to an extent similar to their inhibition of catalysis. It is likely that oligosaccharide substrates of SXA afford similar protection from inactivation by low pH and high temperature.

Example 3

Materials and Methods

Materials and General Methods

Buffers, 4-nitrophenol (4NP), 4-nitrophenyl-β-D-xylopyranoside (4NPX), 4-nitrophenyl-α-L-arabinofuranoside (4NPA), and D-xylose (X1) were obtained from Sigma-Aldrich (St. Louis, Mo.). 1,4-β-D-Xylobiose (X2), 1,4-β-D-xylotriose (X3), 1,4-β-D-xylotetraose (X4), 1,4-β-D-xylopentaose (X5), and 1,4-β-D-xylohexaose (X6) were from Megazyme (Wicklow, Ireland). Water was purified through a Milli-Q unit (Millipore; Billerica, Mass.). All other reagents were reagent grade and high purity. The gene encoding β-xylosidase from *S. ruminantium* GA192 was cloned and expressed in *Escherichia coli* as described (Whitehead and Cotta, 2001, ibid). SXA, produced in *E. coli*, was purified to homogeneity, as judged from SDS-PAGE analysis, by using reverse phase and anionic exchange chromatography steps as described (Example 1, also published as Jordan, D. B., Li, X-L., Dunlap, C. A., Whitehead, T. R., and Cotta, M. A. (2007), *Appl. Biochem. Biotechnol.* 141, 51-76, the contents of which are incorporated by reference herein) with the addition of a final desalting, gel filtration step employing a 2.6×30 cm column of Bio-Gel P-6 DG desalting gel (Bio-Rad; Hercules, Calif.), equilibrated and developed with 20 mM sodium phosphate, pH 7.0. Concentrations of homogeneous SXA protomers (active sites) were determined by using an extinction coefficient at 280 nm of 129600 $M^{-1}$ $cm^{-1}$, calculated from amino acid composition (Example 1; Gill and von Hippel, 1989, ibid). A Cary 50 Bio UV-Visible spectrophotometer (Varian; Palo Alto, Calif.), equipped with a thermostatted holder for cuvettes, was used for spectral and kinetic determinations. A model SX.18MV-R stopped-flow (Applied Physophysics; Leatherhead, UK) with a thermostatted compartment for syringes and reaction chamber and a 2 mm path length for absorbance measurements was used for rapid kinetic studies. Kinetic simulations were through the computer program KINSIM: Chemical Kinetics Simulation System, 32-bit DOS-Extended Version 4.0, March 1997 (Barshop et al., 1983, ibid). Delta extinction coefficients (product-substrate) at 360, 380 and 400 nm were determined for each buffer condition by subtracting the molar absorbance of 4NPX from that of 4-nitrophenol (4NP) (Example 1). The concentration of 4NP was determined by using the published extinction coefficient of 18.3 $mM^{-1}$ $cm^{-1}$ at 400 nm for 4NP in NaOH (Kezdy and Bender, 1962, ibid) Concentrations of 4NPX and 4NPA were determined by incubating substrate with excess enzyme until an end point was reached, adding an aliquot (10-100 μL) to 0.99-0.90 mL 0.1 M NaOH, recording the absorbance at 400 nm and using the extinction coefficient of 18.3 $mM^{-1}$ $cm^{-1}$ for 4NP in NaOH.

HPLC Analysis of Reactions

Products from SXA-catalyzed hydrolysis of substrates X2-X6 and 4NPX, were separated and quantified by using a DX500 HPLC system with an ED40 electrochemical detector (pulsed amperometry), AS3500 autosampler, PA-100 (4×250 mm) anion exchange column, and Chromeleon software (Dionex Corp.; Sunnyvale, Calif.). Samples (25 μL) were injected onto the column equilibrated with 0.1 M NaOH and developed with a 5-min linear gradient (0.1 M NaOH to 33 mM sodium acetate) at ~25° C. and a flow rate of 1 mL $min^{-1}$. Several concentrations of the products of interest (e.g., D-xylose and X2) were used to establish standard curves on the same day experimental samples were run. Substrate concentrations were determined by HPLC analysis of samples incubated with excess SXA for complete conversion to D-xylose.

Kinetics with Substrates X2-X6

For determination of steady-state kinetic parameters of X2-X6 substrates, 0.5-mL reaction mixtures contained varied substrate concentrations (0.9-13 mM) in 100 mM succinate-NaOH, pH 5.3 at 25° C. For pH studies of SXA-catalyzed hydrolysis of X2 and X3, buffers of constant ionic strength (I=0.3 M), adjusted with NaCl, were used as indicated (replacing 100 mM succinate-NaOH, pH 5.3): 100 mM succinate-NaOH (pH 4.3-6), 100 mM sodium phosphate (pH 6-8), and 30 mM sodium pyrophosphate (pH 8-9.2). Before (time=0 min) and after (time=0.5-2 min) initiating reactions with enzyme (7 μL SXA in 20 mM sodium phosphate, pH 7.0), 100-μL aliquots of reaction mixtures were removed and quenched with an equal volume of 0.2 M sodium phosphate pH 11.3 at 0° C. (so that quenched mixtures were pH 10.5-11), and diluted by adding 1 mM sodium phosphate, pH 10.5-11 at 0° C. as necessary (typically 200-800 μL added to 200 μL quenched samples) to adjust concentrations of reactants and products to fall within the linear range of standard curves. Samples were kept on wet ice or the HPLC autosampler at 5° C. until analyzed by HPLC. Initial rates, calculated from linear regressions of the [D-xylose] produced versus time, were fitted to Eq. 1 to determine steady-state kinetic parameters. Parameter, $k_{cat}$, is expressed in moles of substrate hydrolyzed per second per mole enzyme active sites (protomers); thus, for substrate X2, the [D-xylose] produced was divided by two to provide the [X2] hydrolyzed, whereas for X3-X6, the [D-xylose] produced was taken as the concentration of substrate hydrolyzed.

Reaction Progress Curves

For X2, 2-mL reactions contained 100 mM succinate-NaOH, pH 5.3 at 25° C. Concentrations of SXA (protomer) and X2 are indicated in the Brief Description of the Drawings, FIGS. 18-24. Before (time=0) and after initiating reactions with enzyme (7 μL SXA in 20 mM sodium phosphate, pH 7.0), 100-μL aliquots of reaction mixtures were removed, quenched with an equal volume of 0.2 M sodium phosphate pH 11.3 at 0° C., and diluted with 1 mM sodium phosphate, pH 10.5-11 (as above) prior to HPLC analysis.

For 4NPX, 1.5-mL reactions contained 100 mM succinate-NaOH, pH 5.3 at 25° C. and concentrations of 4NPX and SXA (protomer) as indicated in the Brief Description of the Drawings, FIGS. 18-24. Before (time=0) and after initiating reactions with enzyme (7 μL SXA in 20 mM sodium phosphate, pH 7.0), 10-100 μL aliquots of reaction mixtures were removed and added to cuvettes containing 900-990 μL 0.1 M NaOH (final volume=1000 μL); absorbencies at 400 nm were recorded and converted to molarities by using the extinction coefficient of 18.3 mM$^{-1}$ cm$^{-1}$ for 4NP in NaOH (Kezdy and Bender, 1962, ibid).

Determination of Inhibition Constants

For D-xylose inhibition of SXA-catalyzed hydrolysis of 4NPX, 1-mL reactions contained varied concentrations (0.2-7 mM) of 4NPX and varied concentrations (0, 20, 60, and 150 mM) of D-xylose in 100 mM succinate-NaOH, pH 5.3 at 25° C. Reactions were initiated by adding enzyme (7 μL SXA in 20 mM sodium phosphate, pH 7.0) and reaction progress was monitored continuously for 0.3 min at 380 nm to determine initial rates (fitted to lines). For determination of steady-state kinetic parameters, initial rates were fitted to Eq. 2 (competitive inhibition) and Eq. 3 (noncompetitive inhibition).

For inhibition of SXA-catalyzed hydrolysis of 4NPA by two D-xylose preparations having different ratios of α and β anomeric isomers, the stopped-flow instrument was used to allow rapid execution of 3-5 replicates for each reaction condition. The experiment relies on the experimentally determined production of α-D-xylose from SXA-catalyzed hydrolysis of 4NPX and 1,4-β-D-xylose (X2), the experimentally determined half life (~1 h) of α-D-xylose mutarotation to its equilibrium position α:β ratio of 1:2.5), and the experimentally-determined α:β ratio of 6:1 for D-xylose as the immediate product from the SXA-catalyzed hydrolysis of X2 (Example 1); from the latter it can be inferred that the reducing D-xylose moiety of X2 has an anomeric isomer ratio of 2.5:1 (α:β). Left syringe of the stopped-flow contained 0.951, 1.90, or 9.51 mM 4NPA in 100 mM succinate-NaOH, pH 5.3 at 25° C. When the α:β ratio of D-xylose was 6:1, the right syringe contained 5.07 μM SXA and 0, 8.6, or 17.2 mM X2 in 100 mM succinate-NaOH, pH 5.3 at 25° C. After 6 min preincubation to ensure complete conversion of X2 to D-xylose, reactions were initiated by injecting 50 μL from each syringe through the mixing cuvette and absorbance was recorded for 20 s at 360 nm to determine initial rates (fit to line). When the α:β ratio of D-xylose was 1:2.5, the right syringe contained 5.07 μM SXA and 0, 20, or 40 mM D-xylose in 100 mM succinate-NaOH, pH 5.3 at 25° C. After 6 min preincubation (to mimic those containing X2), reactions were initiated by injecting 50 μL from each syringe through the mixing cuvette and absorbance was recorded for 20 s at 360 nm to determine initial rates (fit to line). For determination of steady-state kinetic parameters, initial rates were fitted to Eq. 2 (competitive inhibition).

For inhibition of SXA-catalyzed hydrolysis of 4NPX by 4NP, 1-mL reactions contained varied concentrations of 4NPX, 0 or 9.4 mM 4NP and 7.09-33.8 nm SXA (protomer) in 100 mM succinate-NaOH, pH 5.3 at 25° C. Before (time=0) and after (up to 6 min) initiating reactions by adding enzyme (7 μL SXA in 20 mM sodium phosphate, pH 7.0), 100-μL aliquots of reaction mixtures were removed and quenched with an equal volume of 0.2 M sodium phosphate pH 11.3 at 0° C., and diluted with 1 mM sodium phosphate, pH 10.5-11 (as above) prior to HPLC analysis. Concentrations of D-xylose produced versus time were fitted to lines for determination of initial rates. For determination of steady-state kinetic parameters, initial rates were fitted to Eq. 2 (competitive inhibition).

Equations

Data were fitted to equations by using the computer program Grafit (Erithacus Software; Horley, UK) [Leatherbarrow, R. J. (2001), Grafit Version 5, Erithacus Software Ltd., Horley, U.K.]. Equation numbers referred to throughout this Example refer to the equations shown hereinbelow, and may not correspond to those equation numbers referred to in Examples 1 and 2. Symbol definitions for equations 1-3: ν is the observed initial (steady-state) rate of catalysis, $k_{cat}$ is the maximum rate of catalysis, S is the substrate concentration, $K_m$ is the Michaelis constant, I is the inhibitor concentration, $K_i$ is the dissociation constant for I from the EI complex, and $K_{is}$ is the substrate dissociation constant from the EIS complex. For equations 4-7, p is the determined parameter at a single pH, P is the pH-independent value of the parameter, $K_a$ is the acid dissociation constant of the group affecting P, H$^+$ is the proton concentration, $K_{a1}$ is the acid dissociation constant of the first group affecting P, $K_{a2}$ is the acid dissociation constant of the second group affecting P, $P_1$ is the limit of p associated with $K_{a1}$, and $P_2$ is the limit of p associated with $K_{a2}$.

$$v = \frac{k_{cat} * S}{K_m + S} \quad (1)$$

$$v = \frac{k_{cat} * S}{K_m * \left(1 + \frac{I}{K_i}\right) + S} \quad (2)$$

$$v = \frac{k_{cat} * S}{K_m \left(1 + \frac{I}{K_i}\right) + S\left(1 + \frac{K_m * I}{K_{is} * K_i}\right)} \quad (3)$$

$$p = \frac{P}{1 + \frac{H^+}{K_a}} \quad (4)$$

$$p = \frac{P}{1 + \frac{K_a}{H^+}} \quad (5)$$

$$p = \frac{P}{1 + \frac{H^+}{K_{a1}} + \frac{K_{a2}}{H^+}} \quad (6)$$

$$p = \frac{P_1}{1 + \frac{H^+}{K_{a1}}} + \frac{P_2 - P_1}{1 + \frac{H^+}{K_{a2}}} \quad (7)$$

Results and Discussion

An improved method for quenching SXA reactions was established for determination of steady-state kinetic parameters with xylooligosaccharide substrates X2-X6 (Table 7). The improved quenching method raises the pH of reaction mixtures to ~pH 11, where SXA is inactive (pK$_a$=7 for $k_{cat}/K_m$) and lowers the temperature; it produces much lower background concentrations, stemming from hydrolysis of oligosaccharide substrates off the enzyme to D-xylose and smaller xylooligosaccharides, than the acid quenching method employed previously (Example 1), thus allowing better estimations of rates, particularly at higher concentrations of substrate. In direct comparison to previous determinations at pH 5.3 and 25° C. (example 1), the respective $k_{cat}/K_m$ values for X2, X3, X4, X5 and X6 are lower by 9, 1, 12, 34, and 25% and the respective $k_{cat}$ values are lower by 55, 45, 39, 49, and 15%. The lower $k_{cat}$ values do not affect previous KINSIM simulations of reaction progressions for SXA-catalyzed hydrolysis of X4 and X6 (Example 1), because initial X4 and X6 substrate concentrations of the reactions were low (30% of $K_m$) where parameter $k_{cat}/K_m$ governs rates and, as indicated, there are relatively small differences between the new and previously determined $k_{cat}/K_m$ values. Also, SXA remains the most active β-xylosidase known for promoting hydrolysis of xylooligosaccharides with $k_{cat}$ and $k_{cat}/K_m$ values at pH 5.3 and 25° C. that are higher than those of the second most active β-xylosidase known from the literature, the enzyme from *Bacillus pumilus* (Van Doorslaer et al., 1985, ibid), determined at its pH optimum (pH 7.15) and 25° C., by factors of 10 (X2), 32 (X3), 31 (X4), 20 (X5), and 27 (X6) for $k_{cat}$ and factors of 14 (X2), 16 (X3), 15 (X4), 10 (X5), and 13 (X6) for $k_{cat}/K_m$. For comparison, $k_{cat}$ and $k_{cat}/K_m$ values of SXA with substrate 4NPX at pH 5.3 and 25° C. (Example 1) are higher than those determined for the *B. pumilus* enzyme at pH 7.15 and 25° C. (Van Doorslaer et al., 1985, ibid) by factors of 4 and 5, respectively.

pH dependencies of SXA-catalyzed hydrolysis of X2 and X3 were determined using buffers of constant ionic strength (I=0.3 M) from pH 4.3 to 9.2 (FIGS. 2 and 3); denaturation of SXA at lower pH values precludes their analysis (Example 2, also published as Jordan, D. B., Li, X-L., Dunlap, C. A., Whitehead, T. R., and Cotta, M. A. (2007), *Appl. Biochem. Biotechnol.*, 136-140, 93-104, the contents of which are incorporated by reference herein). pH dependencies of $k_{cat}$, $k_{cat}/K_m$, and $1/K_m$ are similar in shape for X2 and X3 and similar $pK_a$ values were determined (see the Brief Description of the Drawings for FIGS. 19 and 20). A small difference between the two substrates is that $pK_a$ can be determined for the acidic limb of $k_{cat}$ with X3 ($pK_{a1}$ 3.21), but no acidic limb is seen for $k_{cat}$ with X2; the inability to determine the $pK_a$ for X2 stems from the inability to analyze SXA kinetics below pH 4.3. Extension by 2 pH units of the $pK_a$ for $k_{cat}$ over that of $k_{cat}/K_m$ ($pK_{a1}$ 4.8) would not be unusual (Cleland, 1982, ibid). Lower $pK_a$ values for $k_{cat}$ ($pK_{a1}$~3.6) than $k_{cat}/K_m$ ($pK_{a1}$~5.0) for the acidic limbs are also seen with substrates 4NPX and 4NPA (Example 1). pH dependencies of $1/K_m$ indicate that catalytically-inactive, dianionic SXA (D14⁻E186⁻) has 2.9-fold and 3.1-fold lower affinity than catalytically-active, monoanionic SXA (D14⁻E186$^H$) for X2 and X3, respectively. In contrast, D14⁻E186⁻ has 1.9-fold higher affinity than catalytically-active, monoanionic SXA (D14⁻E186$^H$) for 4NPX, and D14⁻E186⁻ has no affinity for 4NPA (Example 1).

Figure 22A:
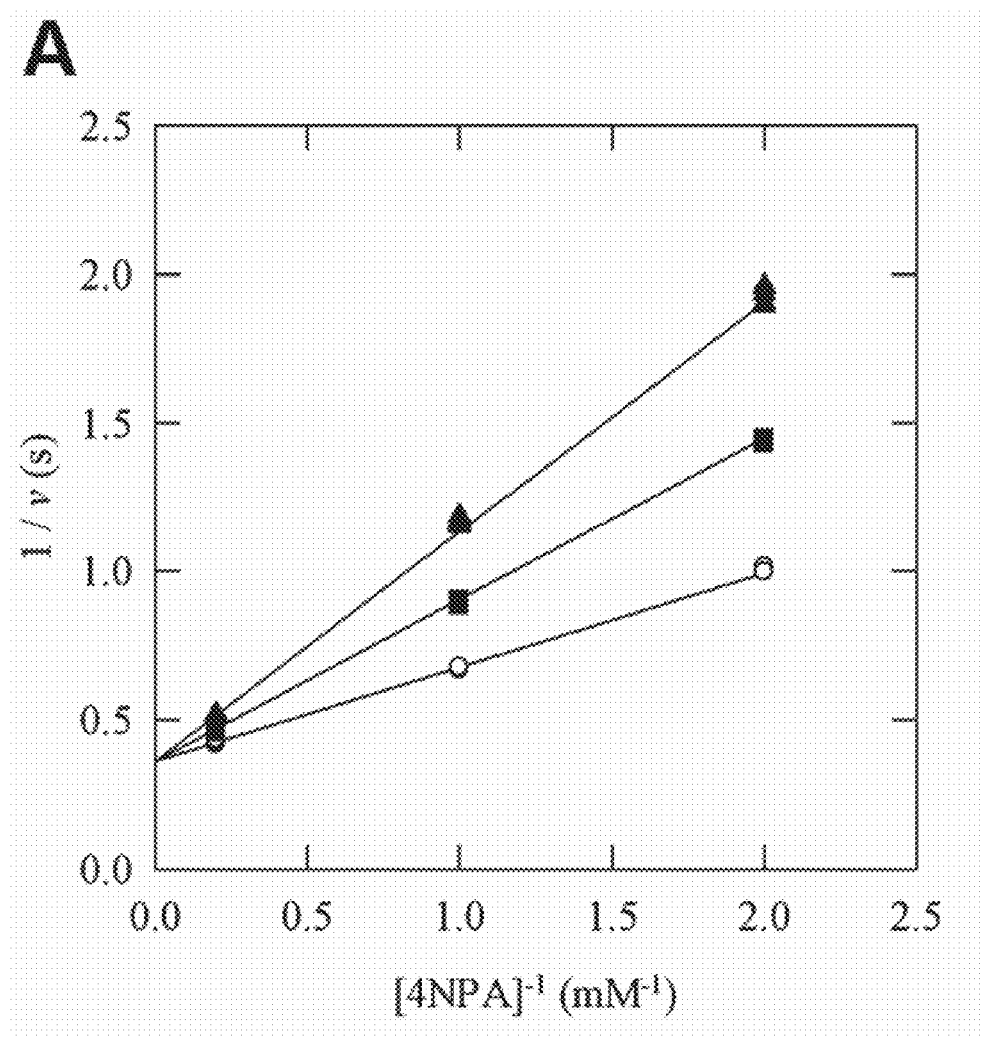
Figure 22B:
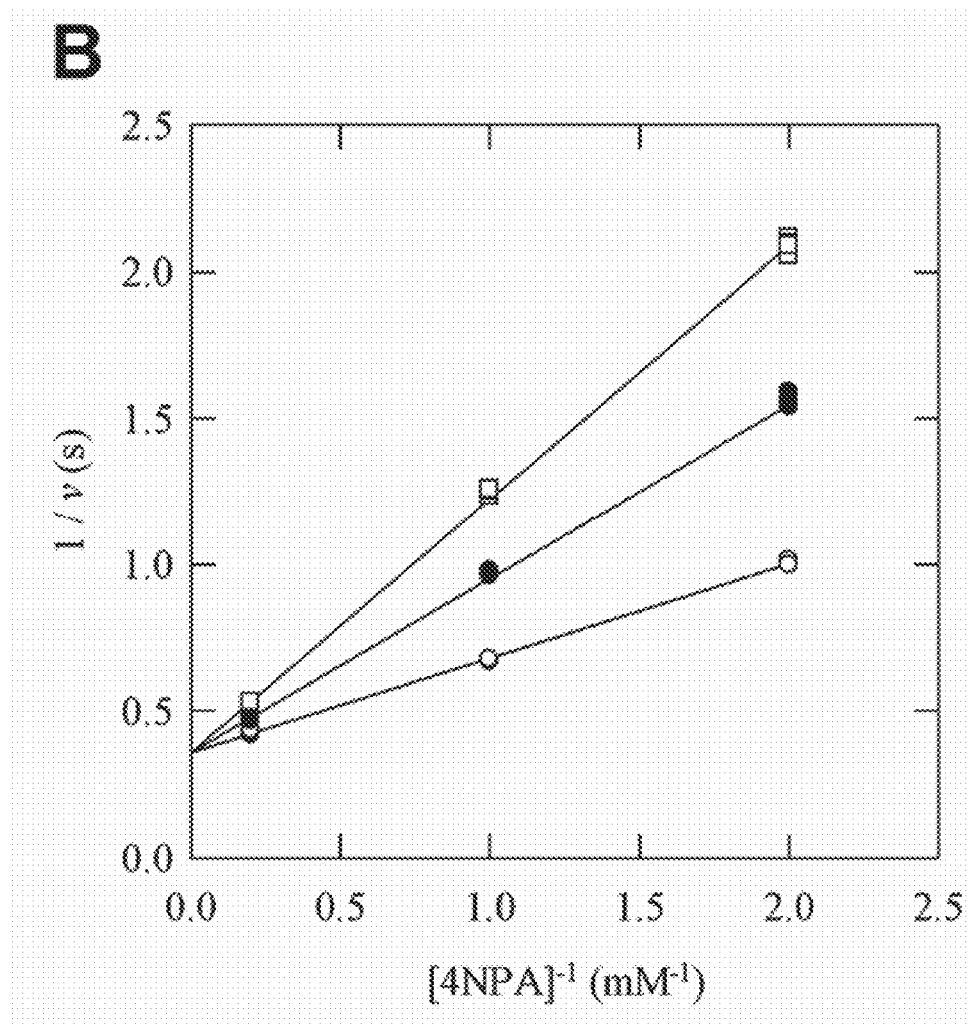

Inhibition of SXA-catalyzed hydrolysis of 4NPX by D-xylose was determined at pH 5.3 and 25° C. by using a continuous spectrophotometric method: $K_i^{4NPX}$ of 9.63±0.30 mM and $K_{is}^{D\text{-}xylose\cdot 4NPX}$ of 15.9±2.1 mM were determined by fitting the data to Eq. 3, describing noncompetitive (or "mixed") inhibition. For comparison with actual reaction progression data acquired by following production of 4NP spectroscopically, values of $k_{cat}^{4NPX}$ (32.1±0.5), $K_m^{4NPX}$ (0.716±0.032), $K_i^{D\text{-}xylose}$ (9.63±0.30 mM), and $K_{is}^{D\text{-}xylose\cdot 4NPX}$ (15.9±2.1 mM) were used as inputs to KINSIM for simulations of four reaction progressions of SXA-catalyzed hydrolysis of 1 mM 4NPX and 5 mM 4NPX at pH 5.3 and 25° C. (FIG. 21). Whereas the simulations adequately describe the two progressions at 1 mM 4NPX, the simulations fail to account for the production of 4NP towards the end of 4NPX consumption of the two progressions containing 5 mM 4NPX. Two possibilities, which could rationalize the discrepancies, were addressed experimentally. The first of these is that the $K_i^{D\text{-}xylose}$ (9.63 mM) input of the simulation was determined from inhibition studies with D-xylose, predominantly in the β conformation (α:β ratio of 1:2.5 at equilibrium), whereas the product of SXA-catalyzed hydrolysis of 4NPX is temporally in the α conformation (half life ~1 h) before mutarotation establishes equilibrium favoring the β conformation (Example 1); potentially, α-D-xylose has greater affinity than β-D-xylose for SXA. To address this, X2 was preincubated with SXA for 6 min to fully convert to D-xylose with α:β ratio of 6:1 (Example 1) prior to initiating reactions with varied concentrations of 4NPA for determination of $K_i^{D\text{-}xylose}$ to compare with $K_i^{D\text{-}xylose}$, determined from reactions with SXA preincubated with D-xylose (α:β ratio of 1:2.5) prior to initiating reactions with varied concentrations of 4NPA. In contrast to 4NPX, SXA-catalyzed hydrolysis of 4NPA is competitively inhibited by D-xylose. From the data collected with D-xylose (α:β ratio of 6:1), $K_i^{D\text{-}xylose}$ of 11.9±0.3 was determined (FIG. 22A). From the data collected with D-xylose (α:β ratio of 1:2.5), $K_i^{D\text{-}xylose}$ of 11.8±0.3 was determined (FIG. 22B). If, for example, all inhibitory activity resided in the α anomeric isomer and β-D-xylose had no affinity for SXA, then $K_i^{D\text{-}xylose}$ for D-xylose with α:β ratio of 1:2.5 would be 3-fold that for D-xylose with α:β ratio of 6:1. Therefore, the two anomeric isomers of D-xylose possess similar affinities for SXA and corrections, on the basis of α and β content, cannot account for the overestimation of reaction progress by the simulations in comparison to the actual progressions of FIG. 21. Similarly, from stopped-flow reactions at pH 7.0 (100 mM sodium phosphate, adjusted with NaCl to ionic strength of 0.3 M) and 25° C., $K_i^{D\text{-}xylose}$ values for inhibition of SXA-catalyzed hydrolysis of 4NPA were similar when the D-xylose solutions contained α:β anomeric isomer ratios of 1:2.5 ($K_i^{D\text{-}xylose}$=5.15±0.08 mM) or 6:1 ($K_i^{D\text{-}xylose}$=4.97±0.05 mM).

The second possible cause for discrepancies between the simulated and actual progressions, is the unaccounted for potential of product 4NP to inhibit the SXA-catalyzed hydrolysis of 4NPX. To address this, $K_i^{4NP}$ for inhibition of SXA-catalyzed hydrolysis of 4NPX was determined at pH 5.3 and 25° C. by using HPLC analysis of D-xylose produced from 4NPX to determine catalyzed rates in the absence and presence of 4NP and fitting the rate data to Eq. 2, describing competitive inhibition (FIG. 23). By including the determined value of $K_i^{4NP}$ (6.28±0.55 mM) in the simulations of SXA-catalyzed hydrolysis of 4NPX, better agreement with actual reaction progressions is generated (FIG. 21).

For comparison with actual reaction progress data acquired by HPLC quantification of D-xylose and 1,4-β-D-xylobiose (X2) concentrations, steady-state values for $k_{cat}^{X2}$ (185±3 s$^{-1}$), $K_m^{X2}$ (2.06±0.08 mM) and $K_i^{D\text{-}xylose}$ (9.63±0.30 mM) were used for KINSIM inputs for simulations of SXA-catalyzed reactions containing 0.922 mM X2 and 7.31 mM X2 (FIG. 24). The simulations adequately describe reaction progress at both high and low X2 concentrations, conditions where the $K_i^{D\text{-}xylose}$ term is more and less important, respectively, to the calculations. Thus, the xylobiose reactions substantiate that α and β anomeric conformations of D-xylose have similar affinities for SXA.

Conclusions

The small discrepancies between the actual and simulated (when not including $K_i^{4NP}$ in the calculations) progress curves for SXA-catalyzed hydrolysis of 4NPX (FIG. 21) prompted experiments to determine $K_i$ values for 4NP and the two preparations of D-xylose with different anomeric isomer ratios. Determinations that the two anomeric isomers of D-xylose have similar $K_i$ values and that 4NP binds to SXA and inhibits catalysis allow more accurate predictions of SXA-catalyzed reactions (FIGS. 21 and 24). Of course the absence of complicating factors, such as subunit cooperativity (SXA is a homotetramer) and transglycosylation back reactions, simplify the parameters needed for kinetic simulations. The ability to simulate reaction progress could have utility in engineering saccharification processes. Undoubtedly, the lack of complicating factors (cooperativity, transglycosylation), which lower rates of hydrolysis, favors the effectiveness of SXA in saccharification processes.

Based on the 2-fold tighter binding of 4NPX by the catalytically-inactive, dianionic SXA (D14⁻E186⁻) than by the catalytically-active, monoanionic SXA (D14⁻E186$^H$), it might have been projected that X2 and X3 would share this property of forming relatively high-affinity, dead-end complexes, which would be detrimental to the usefulness of SXA at higher pH. Determination of 3-fold weaker binding of X2 and X3 by D14⁻E186⁻ than by D14⁻E186$^H$ favors the effectiveness of SXA as a catalyst.

TABLE 7

Steady-State Kinetic Parameters of
SXA Acting on Xylooligosaccharides[a]

| Substrate | $k_{cat}$ (s$^{-1}$) | $k_{cat}/K_m$ (mM$^{-1}$s$^{-1}$) | $K_m$ (mM) |
|---|---|---|---|
| 1,4-β-D-xylobiose (X2) | 185 ± 3 | 90.2 ± 2.5 | 2.06 ± 0.08 |
| 1,4-β-D-xylotriose (X3) | 95.1 ± 1.5 | 44.8 ± 1.5 | 2.12 ± 0.10 |
| 1,4-β-D-xylotetraose (X4) | 91.6 ± 2.3 | 33.3 ± 2.0 | 2.75 ± 0.23 |
| 1,4-β-D-xylopentaose (X5) | 77.2 ± 3.6 | 27.0 ± 2.4 | 2.86 ± 0.38 |
| 1,4-β-D-xylohexaose (X6) | 81.5 ± 2.0 | 26.1 ± 1.2 | 3.12 ± 0.21 |

[a]Reactions contained varied concentrations of substrate in 100 mM succinate-NaOH, pH 5.3 at 25° C. Initial-rate data were fitted to Eq. 1; standard errors (±) are indicated.

It is understood that the foregoing detailed description is given merely by way of illustration and that modifications and variations may be made therein without departing from the spirit and scope of the invention.

We claim:

1. A method for producing xylose comprising contacting xylose-containing plant material with a β-D-xylosidase in an amount and under conditions effective for hydrolyzing oligosaccharides to produce xylose, wherein said β-D-xylosidase comprises the amino acid sequence of Sequence ID No. 2, and further wherein said conditions comprise a pH between about 4.5 and about 7.7.

2. The method of claim 1 wherein said plant material comprises xylooligosaccharides.

3. The method of claim 2 wherein said plant material comprises a plant material hydrolysate.

4. The method of claim 2 wherein said plant material hydrolysate has been produced by hydrolysis of plant material with an acid, base or an enzyme preparation comprising a xylanase, galactosidase, arabinofuranosidase, ferulic acid esterase, coumaric acid esterase, acetic acid esterase, α-glucuronidase, and combinations thereof.

5. The method of claim 2 wherein said substrate comprises sugarcane bagasse, wheat, wheat straw, maize, corn stover, corn cobs, and switchgrass.

6. The method of claim 1 wherein said pH is between about 4.5 and about 7.7.

7. The method of claim 1 wherein said pH is between about 4.5 and about 6.0.

8. The method of claim 1 wherein said β-D-xylosidase is substantially pure.

9. The method of claim 8 further comprising converting said xylose to a secondary product selected from the group consisting of ethanol, butanol, lactic acid, and acetic acid.

10. The method of claim 9 wherein said converting comprises fermenting said xylose to said secondary product.

11. The method of claim 10 wherein said secondary product is ethanol.

12. The method of claim 1 further comprising contacting said plant material with an acid, base or an additional enzyme effective to hydrolyze said plant material.

13. The method of claim 12 wherein said additional enzyme comprises xylanase, galactosidase, arabinofuranosidase, ferulic acid esterase, coumaric acid esterase, acetic acid esterase, α-glucuronidase, and combinations thereof.

* * * * *